United States Patent
Koehnlein

(10) Patent No.: US 12,208,142 B2
(45) Date of Patent: Jan. 28, 2025

(54) PROCESS FOR PROVIDING PEGYLATED PROTEIN COMPOSITION

(71) Applicant: Hoffmann-La Roche Inc., Little Falls, NJ (US)

(72) Inventor: Wolfgang Koehnlein, Penzberg (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 515 days.

(21) Appl. No.: 16/957,462

(22) PCT Filed: Dec. 28, 2018

(86) PCT No.: PCT/EP2018/097122
§ 371 (c)(1),
(2) Date: Jun. 24, 2020

(87) PCT Pub. No.: WO2019/129876
PCT Pub. Date: Jul. 4, 2019

(65) Prior Publication Data
US 2020/0323993 A1 Oct. 15, 2020

(30) Foreign Application Priority Data
Dec. 29, 2017 (EP) .................... 17211124

(51) Int. Cl.
B01D 15/36 (2006.01)
A61K 47/60 (2017.01)
C07K 1/107 (2006.01)
C07K 1/18 (2006.01)
C07K 1/20 (2006.01)
C07K 14/505 (2006.01)

(52) U.S. Cl.
CPC ............ *A61K 47/60* (2017.08); *C07K 1/18* (2013.01); *C07K 1/20* (2013.01); *C07K 14/505* (2013.01)

(58) Field of Classification Search
None
See application file for complete search history.

(56) References Cited

U.S. PATENT DOCUMENTS

| | | | |
|---|---|---|---|
| 5,378,808 A | 1/1995 | D'Andrea et al. | |
| 5,641,670 A | 6/1997 | Treco et al. | |
| 5,733,761 A | 3/1998 | Treco et al. | |
| 5,886,155 A | 3/1999 | Armah et al. | |
| 5,932,462 A | 8/1999 | Harris et al. | |
| 6,583,272 B1 | 6/2003 | Bailon | |
| 8,969,532 B2 | 3/2015 | DeFrees et al. | |
| 11,518,781 B2 | 12/2022 | Koehnlein | |
| 2006/0052291 A1* | 3/2006 | Siegal | A61P 7/06 435/372 |
| 2008/0253992 A1* | 10/2008 | DeFrees | A61P 7/06 435/68.1 |
| 2012/0197007 A1* | 8/2012 | Falkenstein | A61K 38/1816 530/380 |
| 2016/0022828 A1* | 1/2016 | Bossard | A61K 47/60 514/21.3 |
| 2018/0327446 A1 | 11/2018 | Fong et al. | |

FOREIGN PATENT DOCUMENTS

| | | |
|---|---|---|
| CN | 102453087 A | 5/2012 |
| CN | 104513306 B | 8/2016 |
| EP | 0473084 B1 | 11/1995 |
| EP | 1064951 B1 | 8/2007 |
| JP | 2001-112469 A | 4/2001 |
| WO | 9011354 A1 | 10/1990 |
| WO | 9106667 A1 | 5/1991 |
| WO | 9109955 A1 | 7/1991 |
| WO | 9309222 A2 | 5/1993 |
| WO | 9401451 A2 | 1/1994 |
| WO | 9412650 A2 | 6/1994 |
| WO | 9531560 A1 | 11/1995 |
| WO | 0044785 A1 | 8/2000 |
| WO | 2004056852 A2 | 7/2004 |
| WO | 2006024953 A2 | 3/2006 |
| WO | 2007010552 A2 | 1/2007 |
| WO | 2008057683 A2 | 5/2008 |
| WO | 2009010270 A2 | 1/2009 |
| WO | 2011064247 A1 | 6/2011 |
| WO | 2011098526 A1 | 8/2011 |
| WO | 2012035037 A1 | 3/2012 |
| WO | 2013138730 A1 | 9/2013 |

OTHER PUBLICATIONS

US 5,733,746 A, 03/1998, Treco et al. (withdrawn)
The English translation of the Japanese Office Action, mailed on Aug. 11, 2021, in the related Japanese Appl. No. 2020-536096.
The English translation of the Japanese Office Action, mailed on Sep. 13, 2021, in the related Japanese Appl. No. 2020-536134.
The English translation of the Japanese Office Action, mailed on Aug. 25, 2021, in the related Japanese Appl. No. 2020-536191.

(Continued)

Primary Examiner — Elizabeth C. Kemmerer
Assistant Examiner — Regina M DeBerry

(57) ABSTRACT

Processes for providing a PEGylated protein composition comprising mono-PEGylated protein and oligo-PEGylated protein, and processes for providing mono-PEGylated protein compositions with high yield and productivity are provided. The processes are particularly suitable for providing mono-PEGylated erythropoietin composition. The processes comprise reacting a non-PEGylated protein with a PEGylation reagent to produce a mixture comprising non-PEGylated, mono-PEGylated and oligo-PEGylated protein, subjecting the mixture to a step of anion exchange chromatography, and recycling non-PEGylated protein into further PEGylation reactions.

18 Claims, 14 Drawing Sheets
Specification includes a Sequence Listing.

(56) References Cited

OTHER PUBLICATIONS

Snider et al., "Characterization of the heterogeneity of polyethylene glycol-modified superoxide dismutase by chromatographic and electrophoretic techniques," Journal of Chromatography, vol. 599, Issues 1-2, May 22, 1992, pp. 141-155.
European Search Report on Priority Application EP 17211122.1 dated Jun. 12, 2018.
European Search Report on Priority Application EP 17211124.7 dated Jun. 12, 2018.
European Search Report on Priority Application EP 17211103.1 dated Jun. 13, 2018.
International Search Report and Written Opinion on PCT/EP2018/097124 dated Apr. 11, 2019.
International Search Report and Written Opinion on PCT/EP2018/097125 dated Apr. 11, 2019.
International Search Report and Written Opinion on PCT/EP2018/097122 dated Jun. 14, 2019.
Delgado, C., et al., "The Uses and Properties of PEG-Linked Proteins," Crit. Rev. Ther. Drug Carrier 30 Systems 9 (1992) 249-304).
Francis, G.E., et al., "PEGylation of cytokines and other therapeutic proteins and peptides: the importance of biological optimisation of coupling techniques," Int. J. Hematol. 68 (1998) 1-18.
Huang., et al., "Purifying monosubstitutive polyethylene glycol erythropoietin (PEG-EP0) from mixture (EP0, PEG, monosubstitutive PEG-EP0, disubstitutive PEG-EPO and polysubstitutive PEG-EP0, comprises purifying the mixture", WPI / 2017 Clarivate Analytics, vol. 2012, No. 41, May 16, 2012.
Hydrophobic Interaction and Reversed Phase Chromatography, Principles and Methods, GE Handbook, 2006.
Ingold et al, "A reactive continuous chromatographic process for protein PEGylation," React. Chem. Eng., 2016, 1,218.
Lu, Y., et al., "Pegylated peptides III. Solid-phase synthesis with pegylating reagents of varying molecular weight: synthesis of multiply pegylated peptides," Reactive Polymers 22 (1994) 221-229.
Mayolo-Deloisa K, et al., "PEGylated protein separation using different hydrophobic interaction supports: Conventional and monolithic supports," Biotechnology Progress (2016), 32(3), 702-707.

Morpurgo, M., et al., "Preparation and Characterization of Poly-(ethylene glycol) Vinyl Sulfone," J. Bioconjug. Chem. 7 (1996) 363-368.
Muller, E, et al., "Solubility and binding properties of PEGylated lysozyme derivatives with increasing molecular weight on hydrophobic—interaction chromatographic resins," J. Chromatography, (2010), 217(28), 4696-4703.
Pfister et al, "Model-based development of an on-column PEGylation process," Reac React. Chem. Eng., 2016, 1,204.
Pfister et al. "Integrated Process for High Conversion and High Yield Protein PEGylation," Biotechnology and Bioengineering, 2016, 113, 1711-1718.
Shang, X et al., "Purification and analysis of mono-PEGylated HSA by hydrophobic interaction membrane chromatography," J. Separation Science (2013), 36(23), 3673-3681.
Veronese, F.M., "Peptide and protein PEGylation: a review of problems and solutions," Biomaterials 22 (2001) 405-417.
Vickova, "Pharmaceutical applications of isoelectric focusing on microchip with imaged UV detection," J. Chromatography A (2008) 145-152.
Yu, D et al., "Fractionation of different PEGylated forms of a protein by chromatography using environment-responsive membranes," J. Chromatography, (2010), 1217(35) 5595-5601.
Pabst et al., "Comparison of strong anion-exchangers for the purification of a PEGylated protein," Journal of Chromatography A, 1147, pp. 172-182, Feb. 21, 2007.
Bristow, "III. Collaborative Study for the Establishment of a Biological Reference Preparation for Erythropoietin," Pharmeuropa Spec. Issue Biologicals BRP Erythropoietin Bio 97-2 (1997) 31-48.
Huang H et al: "Purifying monosubstitutive polyethylene glycol erythropoietin (PEG-EPO) from mixture of EPO, PEG, monosubstitutive PEG-EPO, disubstitutive PEG-EPO and polysubstitutive PEG-EPO, comprises purifying the mixture", WPI / 2017 Clarivate Analytics,, vol. 2012, No. 41, May 16, 2012, XP002781638.
Fee et al., "PEG-Proteins: Reaction Engineering and Separation Issues," Chemical Engineering Science, 2016, 61, pp. 924-939.
Arthur M. Felix, "Chapter 16 Site-Specific Poly(ethylene glycol)ylation of Peptides," ACS Symposium Series, 680: pp. 218-238, (1997).
US office actions, mailed on Sep. 6, 2022, Dec. 30, 2022 and Jul. 5, 2023, in related U.S Appl. No. 16/958,114.

* cited by examiner

PROCESS FOR PROVIDING PEGYLATED PROTEIN COMPOSITION

CROSS-REFERENCE TO RELATED APPLICATIONS

This application is a National Stage Application of PCT/EP2018/097122 filed Dec. 28, 2018, which claims priority from European Patent Application No. 17211124.7, filed on Dec. 29, 2017. The priority of said PCT and European Patent Application are claimed. Each of prior mentioned applications is hereby incorporated by reference herein in its entirety.

FIELD OF THE INVENTION

The present invention relates to processes for providing PEGylated protein compositions, particularly processes for providing PEGylated protein compositions comprising mono-PEGylated protein and oligo-PEGylated protein and processes for providing mono-PEGylated protein compositions. In particular the present invention relates to processes for providing PEGylated erythropoietin (EPO) compositions comprising mono-PEGylated EPO and oligo-PEGylated EPO and processes for providing mono-PEGylated erythropoietin (EPO) compositions.

BACKGROUND

PEGylation, or pegylation, of proteins refers to the addition of one or more PEG (polyethylene glycol) groups to a protein. PEGylation is particularly useful for therapeutic proteins, for example because it increases in vivo circulation half-life. However, PEGylation may also reduce the biological activity of therapeutic proteins, thereby reducing their effectiveness. There is therefore a balance to be struck between increased circulation time and reduced therapeutic efficacy.

For certain therapeutic proteins, mono-PEGylation is particularly desirable because it provides improved stability without significantly compromising therapeutic efficacy. Mono-PEGylated therapeutic proteins include Mircera®, PegIntron® and Pegasys®. Micera® is a mono-PEGylated form of erythropoietin (EPO) and is used to treat anaemia.

PEGylation reactions tend to produce mixtures comprising non-PEGylated protein (unreacted protein), mono-PEGylated protein, and oligo-PEGylated protein. Reaction conditions that favour a high degree of PEGylation (such as long reaction times, high PEG/protein molar ratio) tend to produce mixture with high a proportion of oligo-PEGylated protein, which results in low yields when mono-PEGylated protein is the desired product. Reaction conditions that favour a low degree of PEGylation (such as short reaction times, low PEG/protein molar ratio) tend to produce mixtures with a high proportion of unreacted (non-PEGylated) protein, which also results in low yields when mono-PEGylated protein is the desired product.

Therapeutic proteins are often expensive to manufacture and therefore processes that provide good yields of mono-PEGylated therapeutic protein (minimal waste of therapeutic protein as unreacted and/or oligo-PEGylated) are economically favourable and therefore are particularly desirable.

Methods of PEGylating a protein of interest while it is bound to an ion exchange chromatography column have been developed in attempts to manipulate the specificity of PEGylation and thereby improve yields of proteins with a desired degree of PEGylation (so-called "on column" methods). Such methods are technically complex and time consuming and consequently have low productivity. Such methods may also consume relatively large amounts of PEGylation reagent, making them economically unfavourable. Various "on column" PEGylation methods are discussed in Pfister (Reac React. Chem. Eng., 2016, 1,204), Ingold (2016) and Fee & Van Alstine (2006).

Methods of providing mono-PEGylated proteins may comprise performing a PEGylation reaction to provide a mixture comprising non-PEGylated protein (unreacted protein), mono-PEGylated protein, and oligo-PEGylated protein, and then performing a purification step to purify the mono-PEGylated protein.

WO 2009/010270 and WO 2012/035037 relate to methods for purifying mono-PEGylated EPO from a mixture comprising non-PEGylated protein, mono-PEGylated protein, and oligo-PEGylated protein. The purification methods involve subjecting the mixture that results from a PEGylation reaction to at least one cation exchange chromatography (CEC) step. The CEC step is performed in bind and elute mode and different elution factions comprise mostly non-PEGylated, mono-PEGylated or oligo-PEGylated EPO. Such CEC methods must be carried out below the isoelectric point of the protein, which in the case of EPO (isoelectric point in the range 4.0 to 5.5) involves CEC at a pH of around 3.0.

Methods for producing mono-PEGylated proteins by performing a PEGylation reaction and then purifying the mono-PEGylated protein from the resultant mixture may involve recycling unreacted (non-PEGylated) protein. These methods involve recovering unreacted protein and adding it to a subsequent PEGylation reaction. Such recycling improves the overall yield of mono-PEGylated protein.

Pfister (Biotech and Bioeng, 2016) describes a process in which a PEGylation reaction is performed followed by purification of mono-PEGylated protein from a mixture comprising unreacted (non-PEGylated), mono-PEGylated, and oligo-PEGylated protein. In the process unreacted protein is recovered and used in a subsequent PEGylation reaction. The purification process comprises cation exchange chromatography (CEC) in bind and elute mode, wherein unreacted protein, mono-PEGylated protein and oligo-PEGylated protein are separated in sequential elution. Unreacted protein is eluted last, using a high salt elution buffer. Recycling of unreacted protein therefore requires removal of salt by diafiltration before it can be subject to a further PEGylation reaction. The requirement for removal of salt reduces productivity and increases complexity of the process.

The present invention has been devised in light of the above considerations.

SUMMARY OF THE INVENTION

The present invention relates to processes for providing PEGylated protein compositions comprising mono-PEGylated protein and oligo-PEGylated protein and processes for providing mono-PEGylated protein compositions. The processes of the invention are particularly suitable for providing PEGylated EPO compositions comprising mono-PEGylated EPO and oligo-PEGylated EPO, as well as mono-PEGylated EPO compositions. Advantages of the process described herein include high yield and productivity.

In a first aspect, the present invention provides a process for producing a PEGylated protein mixture, the process comprising: (a) reacting a non-PEGylated protein with a PEGylation reagent to produce a mixture of reaction products comprising non-PEGylated protein and PEGylated protein, wherein the PEGylated protein comprises mono-PEGylated protein and oligo-PEGylated protein; (b) subjecting the mixture of reaction products to an ion exchange chromatography (IEC) step to provide an IEC flow-through solution in which the fraction of PEGylated protein is increased relative to the mixture of reaction products; the IEC step comprising applying the mixture of reaction products to an IEC material under conditions suitable for binding non-PEGylated protein; and (c) collecting the IEC flow-through solution from step b) to provide a PEGylated protein mixture comprising mono-PEGylated protein and oligo-PEGylated protein, wherein non-PEGylated protein is recovered in step b) by eluting an IEC eluate from the IEC material and the eluted non-PEGylated protein is used in a subsequent PEGylation reaction.

The non-PEGylated protein may be recovered in step b) by elution and used in a subsequent PEGylation reaction. That is, step b) may further comprise eluting non-PEGylated protein in an IEC eluate. The IEC eluate comprises non-PEGylated protein.

The processes may involve two or more cycles of steps (a), (b) and (c), in which non-PEGylated protein is recovered in step b) by eluting an IEC eluate from the IEC material and the eluted non-PEGylated protein is used in a subsequent PEGylation reaction.

The IEC step may be an anion exchange chromatography (AEC) step, or a cation exchange chromatography (CEC) step.

The present invention provides a process for producing a PEGylated protein mixture, the process comprising: (a) reacting a non-PEGylated protein with a PEGylation reagent to produce a mixture of reaction products comprising non-PEGylated protein and PEGylated protein, wherein the PEGylated protein comprises mono-PEGylated protein and oligo-PEGylated protein; (b) subjecting the mixture of reaction products to an anion exchange chromatography (AEC) step to provide an AEC flow-through solution in which the fraction of PEGylated protein is increased relative to the mixture of reaction products; the AEC step comprising applying the mixture of reaction products to an AEC material under conditions suitable for binding non-PEGylated protein; and (c) collecting the AEC flow-through solution from step b) to provide a PEGylated protein mixture comprising mono-PEGylated protein and oligo-PEGylated protein, wherein non-PEGylated protein is recovered in step b) by eluting an AEC eluate from the AEC material and the eluted non-PEGylated protein is used in a subsequent PEGylation reaction.

The processes may involve two or more cycles of steps (a), (b) and (c), in which non-PEGylated protein is recovered in step b) by eluting an AEC eluate from the AEC material and the eluted non-PEGylated protein is used in a subsequent PEGylation reaction.

The mixture of reaction products may contain a relatively low proportion of oligo-PEGylated protein. For example, the mixture of reaction products may comprise less than 25%, 20%, 15%, 10% or 5% oligo-PEGylated protein.

The mixture of reaction products may comprise at least about 20%, 30%, 40%, 45%, 50%, 55%, 60% or 70% of non-PEGylated protein.

The IEC flow-through solution (AEC or CEC flow-through solution) may contain a relatively high proportion of PEGylated protein. For example, the IEC flow-through solution may comprise at least about 90%, 95%, 98%, 99% or at least about 99.9% PEGylated protein. The AEC flow-through solution may contain a relatively high proportion of PEGylated protein. For example, the AEC flow-through solution may comprise at least about 90%, 95%, 98%, 99% or at least about 99.9% PEGylated protein.

The protein may be erythropoietin (EPO). The protein may be a hormone. The protein may be a hormone, a cytokine, an enzyme or an antibody.

The processes of the invention involve performing a PEGylation reaction and recycling non PEGylated protein. Such processes are advantageous because they enable relatively high yield.

The processes of the invention may involve performing a PEGylation reaction at about pH 7.0 to 9.0, which may be performed, for example, using an N-Hydroxysuccinimide (NHS) activated PEG reagent. The PEGylation reaction may be performed at about pH 7.5 to 8.5, or at about pH 8.0, and may be performed using an NHS activated PEG reagent. This provides a relatively rapid PEGylation step, which contributes to the overall rapidity of and high productivity of the processes described herein. The protein to by PEGylated may be erythropoietin.

The processes involve performing a PEGylation reaction to provide the mixture of reaction products, and recycling the non-PEGylated protein (unreacted protein) from that PEGylation reaction. The non PEGylated protein is recovered from the mixture of reaction products as part of an IEC step. The IEC step involves contacting the mixture of reaction products with an ion exchange material. The IEC flow-through comprises a relatively high proportion of PEGylated protein (mono-PEGylated and oligo-PEGylated protein) because most of the non-PEGylated protein binds to the anion exchange material. Thus non-PEGylated protein may be recovered from the mixture of reaction products by eluting it from the IEC material. The recovered non-PEGylated protein is added to a subsequent PEGylation reaction, thereby recycling the non-PEGylated protein.

The processes involve performing a PEGylation reaction to provide the mixture of reaction products, and recycling the non-PEGylated protein (unreacted protein) from that PEGylation reaction. The non PEGylated protein is recovered from the mixture of reaction products as part of an AEC step. The AEC step involves contacting the mixture of reaction products with an anion exchange material. The AEC flow-through comprises a relatively high proportion of PEGylated protein (mono-PEGylated and oligo-PEGylated protein) because most of the non-PEGylated protein binds to the anion exchange material. Thus non-PEGylated protein may be recovered from the mixture of reaction products by eluting it from the AEC material. The recovered non-PEGylated protein is added to a subsequent PEGylation reaction, thereby recycling the non-PEGylated protein.

The recycling of non-PEGylated protein in the processes disclosed herein is achieved by eluting non-PEGylated protein in the IEC step. The recycling of non-PEGylated protein in the processes disclosed herein is achieved by eluting non-PEGylated protein in the AEC step. Elution of non-PEGylated protein from an anion exchange material is relatively straightforward and fast, thereby enabling simple and rapid recovery of unreacted protein for recycling. The rapidity of the elution for non-PEGylated protein recycling contributes to the overall rapidity and productivity of the processes disclosed herein.

The processes are performed using a mixture of reaction products that contains non-PEGylated, mono-PEGylated and oligo-PEGylated protein. The proportion of oligo-PEGylated protein in the mixture of reaction products may be relatively low. The processes involve an ion exchange chromatography (IEC) step that provides an IEC flow through solution in which the fraction of PEGylated protein is increased relative to the mixture of reaction products. The processes involve an ion exchange chromatography (IEC) step that provides an IEC flow through solution in which the fraction of non-PEGylated protein is decreased relative to the mixture of reaction products. The IEC flow-through solution may contain a high proportion of PEGylated protein, wherein the PEGylated protein consists of mono-PEGylated protein and oligo-PEGylated protein. That is, the processes of the invention involve an IEC step that is performed in flow through mode. The IEC step in flow though mode is relatively rapid. The relatively fast IEC step of the invention contributes to the relatively overall high productivity of the processes of the invention. The IEC step may be an AEC step or a CEC step.

The IEC flow-through solution has an increased fraction of PEGylated protein relative to the mixture of reaction products. The AEC flow-through solution has a decreased fraction of non-PEGylated protein relative to the mixture of reaction products The processes may involve an anion exchange chromatography (AEC) step that provides an AEC flow through solution in which the fraction of PEGylated protein is increased relative to the mixture of reaction products. The processes involve an anion exchange chromatography (AEC) step that provides an AEC flow through solution in which the fraction of non-PEGylated protein is decreased relative to the mixture of reaction products. The AEC flow-through solution may contain a high proportion of PEGylated protein, wherein the PEGylated protein consists of mono-PEGylated protein and oligo-PEGylated protein. That is, the processes of the invention involve an AEC step that is performed in flow through mode. The AEC step in flow though mode is relatively rapid. The relatively fast AEC step of the invention contributes to the relatively overall high productivity of the processes of the invention.

An AEC flow-through solution has an increased fraction of PEGylated protein relative to the mixture of reaction products. The AEC flow-through solution has a decreased fraction of non-PEGylated protein relative to the mixture of reaction products.

An AEC step comprises applying the mixture of reaction products to an anion exchange material. The anion exchange material may be a strong anion exchange material. Suitable materials are well known in the art and include Toyopearl SuperQ 650M, which is a strong anion exchange material. The anion exchange material may have a low binding capacity for the PEGylated form of the protein.

The IEC material may have a binding capacity for PEGylated protein of less than about 1.5 g/L. The IEC material may have a binding capacity for PEGylated protein of less than about 1.0 g/L, 0.75 g/L, 0.5 g/L, 0.25 g/L, 0.10 g/L, or 0.05 g/L. The binding capacity may be the dynamic binding capacity. The anion exchange material may have a binding capacity for PEGylated protein of less than about 1.5 g/L, less than about 1.0 g/L, less than about 0.75 g/L, less than about 0.5 g/L, less than about 0.1 g/L, less than about 0.05 g/L, less than about 0.01 g/L or less than about 0.001 g/L. The anion exchange material may have a binding capacity for PEGylated protein of close to 0 g/L (i.e. close to 0 g of PEGylated protein/L AEC resin). In particular, the anion exchange material may have a binding capacity for PEGylated EPO of less than about 0.5 g/L, less than about 0.05 g/L, less than about 0.01 g/L or less than about 0.001 g/L. The anion exchange material may have a binding capacity for PEGylated EPO of close to 0 g/L (i.e. close to 0 g of PEGylated EPO/L AEC resin). The IEC material may be an AEC material and the PEGylated protein may be PEGylated erythropoietin.

The IEC material may have a relatively high binding capacity for non-PEGylated protein (e.g. non-PEGylated EPO) of 20-50 g/L, 30-40 g/L, or about 35 g/L. The IEC material may have a binding capacity for non-PEGylated protein (e.g. non-PEGylated EPO) of at least about 20 g/L, 25 g/L, 30 g/L or about 35 g/L. The binding capacity may be the dynamic binding capacity. The IEC material may be an AEC material and the non-PEGylated protein may be non-PEGylated erythropoietin. The protein may be erythropoietin (EPO). The protein may be a hormone. The protein may be a hormone, a cytokine, an enzyme or an antibody.

The process may comprise an anion exchange chromatography (AEC) step and the protein may be erythropoietin.

The use of an ion exchange material with a low binding capacity for the PEGylated form of the protein is advantageous because it facilitates rapid separation of non-PEGylated protein from PEGylated protein. The IEC step can be performed in flow through mode to rapidly provide an IEC flow-through solution from which most, or almost all, of the unreacted (non-PEGylated) protein has been removed. Hence the flow through solution from the IEC step comprises a relatively high proportion of PEGylated protein. It may comprise at least about 80%, 85%, 90% or 95% PEGylated protein, or 80-95% PEGylated protein. It may comprise at least about 90% PEGylated protein. It may comprise at least about 95% PEGylated protein. It may comprise a low proportion, close to zero, or zero non-PEGylated protein. It may comprise less than about 20%, 15%, 10% or 5% non-PEGylated protein, or about 20-5% non-PEGylated protein. It may comprise less than 10% non-PEGylated protein. It may comprise less than 5% non-PEGylated protein.

A further advantage of using an ion exchange material with a low binding capacity for the PEGylated form of the protein is that it facilitates rapid recovery of unreacted (non-PEGylated) protein from the ion exchange material. The non PEGylated protein may be recovered rapidly by step elution, which may provide an eluate comprising the non-PEGylated protein in a relatively concentrated form which may be suitable for direct addition to a PEGylation reaction. The non PEGylated protein may be eluted from the anion exchange material in an elution step performed at a relatively low conductivity, or low salt concentration, which facilitates recycling of non-PEGylated protein for example because removal of high salt concentrations (for example by diafiltration, reconcentration or buffer exchange) is not required before the eluate is added to a subsequent PEGylation reaction. The use of an ion exchange material with a low binding capacity for the PEGylated form of the protein is thus advantageous because it provides for rapid recovery of unreacted (non-PEGylated) protein in a form that is particularly suitable for recycling in a subsequent PEGylation reaction.

The use of an anion exchange material with a low binding capacity for the PEGylated form of the protein is advantageous because it facilitates rapid separation of non-PEGylated protein from PEGylated protein. The AEC step can be performed in flow through mode to rapidly provide an AEC flow-through solution from which most, or almost all, of the unreacted (non-PEGylated) protein has been removed. Hence the flow through solution from the AEC step comprises a relatively high proportion of PEGylated protein. It may comprise at least about 80%, 85%, 90% or 95% PEGylated protein, or 80-95% PEGylated protein. It may comprise at least about 90% PEGylated protein. It may comprise at least about 95% PEGylated protein. It may comprise a low proportion, close to zero, or zero non-PEGylated protein. It may comprise less than about 20%, 15%, 10% or 5% non-PEGylated protein, or about 20-5% non-PEGylated protein. It may comprise less than 10% non-PEGylated protein. It may comprise less than 5% non-PEGylated protein.

A further advantage of using an anion exchange material with a low binding capacity for the PEGylated form of the protein is that it facilitates rapid recovery of unreacted (non-PEGylated) protein from the anion exchange material. The non PEGylated protein may be recovered rapidly by step elution, which may provide an eluate comprising the non-PEGylated protein in a relatively concentrated form which may be suitable for direct addition to a PEGylation reaction. The non PEGylated protein may be eluted from the anion exchange material in an elution step performed at a relatively low conductivity, or low salt concentration, which facilitates recycling of non-PEGylated protein for example because removal of high salt concentrations (for example by diafiltration, reconcentration or buffer exchange) is not required before the eluate is added to a subsequent PEGylation reaction. The use of an anion exchange material with a low binding capacity for the PEGylated form of the protein is thus advantageous because it provides for rapid recovery of unreacted (non-PEGylated) protein in a form that is particularly suitable for recycling in a subsequent PEGylation reaction.

The processes of the invention involve providing a PEGylated protein mixture comprising mono-PEGylated protein and oligo-PEGylated protein, which comprises collecting the flow-through solution from the IEC step. Collecting the IEC flow-through solution may comprise collecting batches of IEC flow-through solution from separate IEC cycles, in this way a PEGylated protein mixture is provided which is a pooled PEGylated protein mixture. The IEC step may be an AEC step or a CEC step.

The processes of the invention involve providing a PEGylated protein mixture comprising mono-PEGylated protein and oligo-PEGylated protein, which comprises collecting the flow-through solution from the AEC step. Collecting the AEC flow-through solution may comprise collecting batches of AEC flow-through solution from separate AEC cycles, in this way a PEGylated protein mixture is provided which is a pooled PEGylated protein mixture. In a second aspect, the present invention provides processes for producing a mono-PEGylated protein composition comprising at least about 90% mono-PEGylated protein, the process comprising: subjecting the PEGylated protein mixture comprising mono-PEGylated protein and oligo-PEGylated protein produced by a process according to the first aspect of the invention to a purification process separating mono-PEGylated protein and oligo-PEGylated protein; and recovering a mono-PEGylated protein composition in which the fraction of mono-PEGylated protein is increased relative to the PEGylated protein mixture, wherein the mono-PEGylated protein composition comprises at least about 90% mono-PEGylated protein.

The mono-PEGylated protein composition may contain a relatively high proportion of mono-PEGylated protein. For example, the protein composition may comprise at least about 95%, 98%, 99%, or 99.9% mono-PEGylated protein.

PEGylation reactions tend to produce mixtures comprising non-PEGylated protein (unreacted protein), mono-PEGylated protein, and oligo-PEGylated protein. Mono-PEGylated proteins may be desirable because they provide a balance between increased half-life and comparable biological activity relative to non-PEGylated and oligo-PEGylated versions of the protein. Proteins, especially therapeutic proteins, are often expensive to manufacture and therefore processes that provide good yields of mono-PEGylated therapeutic protein are particularly desirable. Processes that provide good yields of mono-PEGylated EPO (Mircera®) are particularly desirable.

The processes disclosed herein are advantageous because they are relatively rapid, and therefore enable relatively high productivity. The processes disclosed herein also enable high yield, in that a high proportion of the starting protein becomes PEGylated, and in particular mono-PEGylated. The processes disclosed herein also provide mono-PEGylated protein compositions of relatively high purity.

The flow-through solution from the IEC step is used to provide a PEGylated protein mixture comprising mono-PEGylated protein and oligo-PEGylated protein For example the flow-through solution from an AEC step is used to provide a PEGylated protein mixture comprising mono-PEGylated protein and oligo-PEGylated protein. This mixture is subjected to a purification process to separate the mono-PEGylated protein from the oligo-PEGylated protein and thereby provide a composition comprising a relatively high proportion of mono-PEGylated protein. The purification process may comprise subjecting the PEGylated protein mixture to a hydrophobic interaction chromatography (HIC) step. Both the anion exchange step and HIC step are relatively rapid, thereby providing a relatively rapid process for producing a mono-PEGylated protein composition. The HIC step may be performed in flow through mode, which is particularly rapid, to provide a rapid process for producing a mono-PEGylated protein composition.

The processes of the invention involve collecting the flow-through solution from the IEC step (which may be an AEC or a CEC step). For example the processes of the invention may involve collecting an IEC flow-through solution. Collecting the IEC (AEC or CEC) flow-through solution may comprise collecting batches or fractions of IEC (AEC or CEC) flow-through solution from separate IEC (AEC or CEC) cycles, in this way a PEGylated protein mixture is provided which is a pooled PEGylated protein mixture. Collecting the IEC (AEC or CEC) flow-through solution may comprise delivering the IEC (AEC or CEC) flow-through solution to a HIC material via an in-line connection, in an "in-line conditioning" operation. Collecting the IEC (AEC or CEC) flow-through solution may comprise delivering the IEC (AEC or CEC) flow-through solution to a vessel for conditioning the IEC (AEC or CEC) flow-through solution. Collecting the IEC (AEC or CEC) flow-through solution may comprise delivering the IEC (AEC or CEC) flow-through solution directly to the HIC material. When the IEC (AEC or CEC) flow-through solution is delivered directly to the HIC material the IEC (AEC or CEC) flow-through solution may be conditioned for example by in-line conditioning. There may be a continuous flow of IEC (AEC or CEC) flow-through solution (PEGylated protein mixture) from the IEC (AEC or CEC) material to the HIC material which is in-line conditioned to provide a continuous low of flow-through solution to the HIC material. The IEC (AEC or CEC) flow-through solution may comprise a low proportion of non-PEGylated protein and a high proportion of PEGylated protein (mono-PEGylated and oligo-PEGylated protein). The processes of the invention may further involve separating the mono-PEGylated protein from the oligo-PEGylated protein in the PEGylated protein mixture by performing a hydrophobic interaction chromatography (HIC) step.

The processes of the invention are particularly suitable for producing mono-PEGylated EPO compositions. In processes for producing mono-PEGylated EPO, the AEC step is performed at a pH of about 7.0 to 10.0, about 7.0 to 9.0, about 7.5 to 8.5, or about 8.0. This is advantageous over processes involving cation exchange chromatography (CEC) which is generally performed at a pH of 3.0 or lower. Acid conditions of about pH 3.0 or lower may have adverse effects on EPO quality, such adverse effects are reduced in the processes of the present invention, which do not require CEC and thus do not require the low pH conditions necessary for CEC-based purification of EPO.

Furthermore, acidic forms (acidic variants) of EPO may have higher therapeutic activity, making them particularly useful. However, recovery of mono-PEGylated acidic forms of EPO by CEC may be poor because their elution conditions in CEC are similar to those of di-PEGylated non-acidic forms of EPO. Acidic conditions result in the oxidation of the side chains of amino acids in a protein molecule. As CEC separates protein molecules according to their charge, basic variants of a species will elute later than acidic variants. For this reason, the CEC elution profile of di-pegylated non-acidic forms of EPO tends to overlap with mono-PEGylated acidic forms of EPO. The poor recovery of these useful mono-PEGylated acidic EPO forms by CEC is reduced in the processes disclosed herein, which do not rely on CEC to separate mono-PEGylated from oligo-PEGylated EPO.

The advantages associated with the invention to provide mono-PEGylated EPO may apply to other proteins, particularly other therapeutic proteins. That is, avoidance of low pH conditions and recovery of acidic variants may render the invention useful for providing mono-PEGylated proteins other than mono-PEGylated EPO. The processes may comprise carrying out the IEC and HIC steps at substantially the same pH. The processes may comprise carrying out the PEGylation reaction, IEC and HIC steps at substantially the same pH. The processes may comprise carrying out the AEC step and purification process at substantially the same pH. The processes may comprise carrying out the AEC and HIC steps at substantially the same pH. The processes may comprise carrying out the PEGylation reaction, AEC and HIC steps at substantially the same pH. The pH may be about 7.0 to 9.0, or about 7.5 to 8.5, or about 8.0. Substantially the same pH may refer to ±0.5 pH units. Performing steps of the process at substantially the same pH is advantageous because it avoids the need for pH adjustments between steps, which pH adjustments may be time-consuming and therefore productivity-reducing. The process may comprise carrying out a PEGylation reaction to provide a mixture of reaction products and applying the mixture of reaction products directly to the IEC material. That is, the process may comprise carrying out a PEGylation reaction and applying the resultant mixture to the IEC material without adjusting the pH of the mixture.

The processes of the invention involve providing a PEGylated protein mixture comprising mono-PEGylated protein and oligo-PEGylated protein, which comprises collecting the flow-through solution from the IEC step. Collecting the IEC flow-through solution may comprise collecting batches of IEC flow-through solution from separate IEC cycles, in this way a PEGylated protein mixture is provided which is a pooled PEGylated protein mixture. The processes of the invention involve providing a PEGylated protein mixture comprising mono-PEGylated protein and oligo-PEGylated protein, which comprises collecting the flow-through solution from the AEC step. Collecting the AEC flow-through solution may comprise collecting batches of AEC flow-through solution from separate AEC cycles, in this way a PEGylated protein mixture is provided which is a pooled PEGylated protein mixture.

The processes of the invention involve subjecting a PEGylated protein mixture to a purification process. This may involve subjecting a pooled PEGylated protein mixture to a purification process. Collecting the IEC flow-through solution may comprise delivering the IEC flow-through solution to a HIC material via an in-line connection, in an "in-line conditioning operation". Collecting the IEC flow-through solution may comprise delivering the IEC flow-through solution to a vessel for conditioning the IEC flow-through solution to provide a PEGylated protein mixture. The IEC flow-through solution may comprise a low proportion of non-PEGylated protein and a high proportion of PEGylated protein (mono-PEGylated and oligo-PEGylated protein). The purification process may comprise subjecting the PEGylated protein mixture to a hydrophobic interaction chromatography (HIC) step. The HIC step may be performed in flow through mode. The HIC step in flow through mode may comprise contacting the PEGylated protein mixture with a hydrophobic interaction material, and collecting the flow-through. The flow-through comprises a relatively high proportion of mono-PEGylated protein. Performing the HIC step in flow through mode is advantageous because it can be performed relatively rapidly, thereby contributing to the overall rapidity and productivity of the process. Performing the HIC step in flow through mode, rather than bind and elute mode, is advantageous because it can be performed using a column of relatively small size.

The step of providing the PEGylated protein mixture may comprise pooling the flow-through solution from two IEC steps, or three IEC steps, or more than three IEC steps, or four IEC steps, or five IEC steps. Such pooling of IEC flow-through solution enables the HIC step to produce a mono-PEGylated protein composition from the products of multiple PEGylation reactions, which is relatively efficient. The IEC steps may be a series of AEC steps, or a series of CEC steps. The processes of the invention involve subjecting a PEGylated protein mixture to a purification process. This may involve subjecting a pooled PEGylated protein mixture to a purification process. Collecting the AEC flow-through solution may comprise delivering the AEC flow-through solution to a HIC material via an in-line connection, in an "in-line conditioning operation". Collecting the AEC flow-through solution may comprise delivering the AEC flow-through solution to a vessel for conditioning the AEC flow-through solution to provide a PEGylated protein mixture. Collecting the AEC flow-through solution may comprise delivering the AEC flow-through solution directly to the HIC material. When the AEC flow-through solution is delivered directly to the HIC material the AEC flow-through solution may be conditioned for example by in-line conditioning. There may be a continuous flow of AEC flow-through solution from the AEC material to the HIC material which is in-line conditioned to provide a continuous flow of conditioned flow-through solution to the HIC material. The AEC flow-through solution may comprise a low proportion of non-PEGylated protein and a high proportion of PEGylated protein (mono-PEGylated and oligo-PEGylated protein). The purification process may comprise subjecting the PEGylated protein mixture to a hydrophobic interaction chromatography (HIC) step.

Conditioning the IEC flow-through solution may be referred to as providing a conditioned second mixture. Conditioned second mixtures are described in more detail below. Conditioning an IEC flow-through solution (or providing a conditioned second mixture) may comprise the addition of salt. Conditioning an IEC flow-through solution the addition of bicine. Conditioning an IEC flow-through solution (or providing a conditioned second mixture) may comprise the addition of salt and bicine. Conditioning an IEC flow-through solution (or providing a conditioned second mixture) may comprise the addition of salt and/or bicine to provide a conditioned second mixture as described below.

The HIC step may be performed in flow through mode. The HIC step in flow through mode may comprise contacting the PEGylated protein mixture with a hydrophobic interaction material, and collecting the flow-through. The flow-through comprises a relatively high proportion of mono-PEGylated protein. Performing the HIC step in flow through mode is advantageous because it can be performed relatively rapidly, thereby contributing to the overall rapidity and productivity of the process. Performing the HIC step in flow through mode, rather than bind and elute mode, is advantageous because it can be performed using a column of relatively small size.

The step of providing the PEGylated protein mixture may comprise pooling the flow-through solution from two IEC steps, or three IEC steps, or more than three IEC steps, or four IEC steps, or five IEC steps. Such pooling of IEC flow-through solution enables the HIC step to produce a mono-PEGylated protein composition from the products of multiple PEGylation reactions, which is relatively efficient. For example the step of providing the PEGylated protein mixture may comprise pooling the flow-through solution from two AEC steps, or three AEC steps, or more than three AEC steps, or four AEC steps, or five AEC steps. Such pooling of AEC flow-through solution enables the HIC step to produce a mono-PEGylated protein composition from the products of multiple PEGylation reactions, which is relatively efficient.

SUMMARY OF THE FIGURES

In the figures "EPO" refers to un-reacted EPO (non-PEGylated EPO), "mono" refers to mono-PEGylated EPO, "oligo" refers to oligo-PEGylated EPO. "F/T" refers to flow-through solution.

FIG. 8.

DETAILED DESCRIPTION OF THE INVENTION

Figure 1:
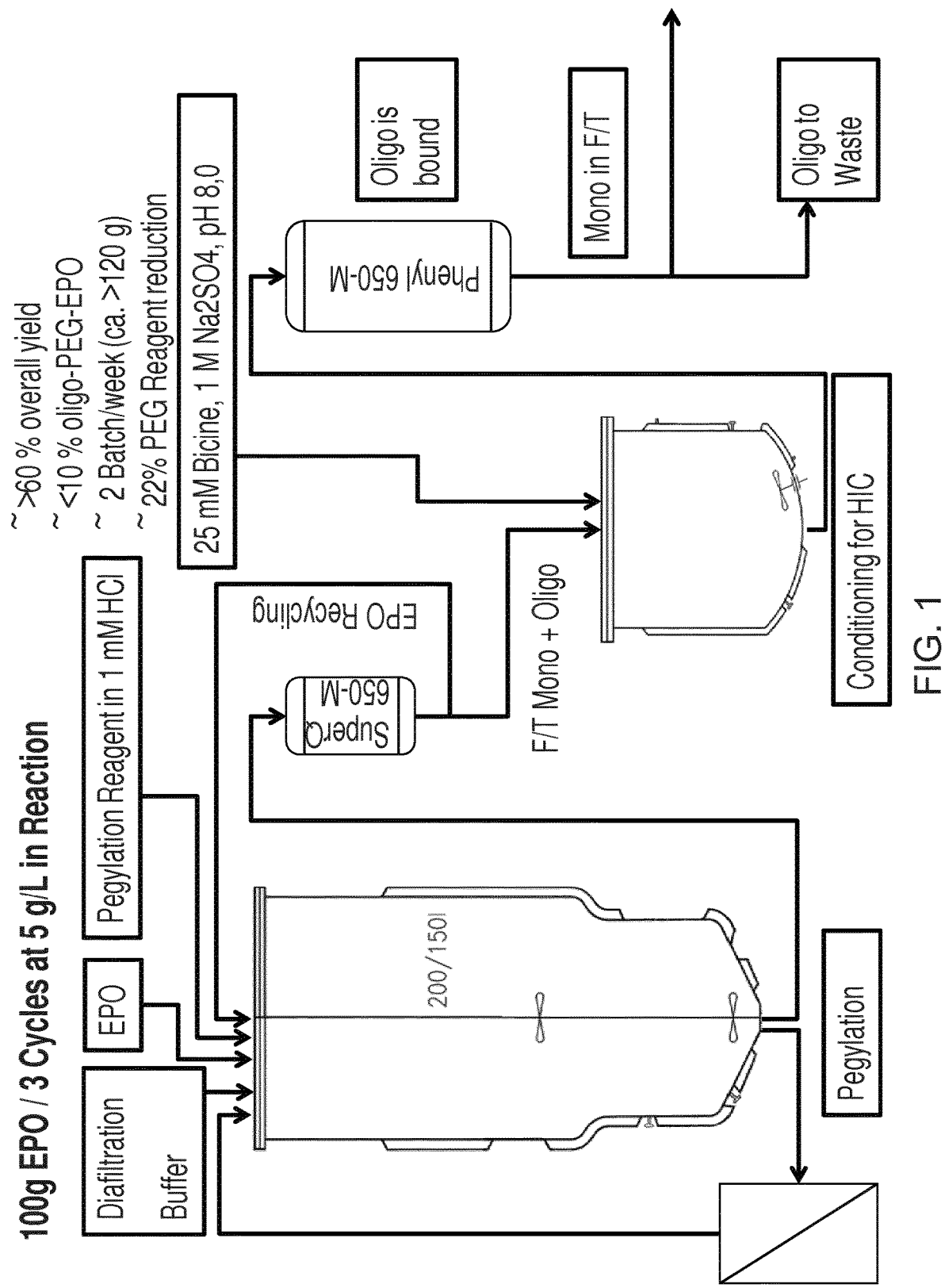
FIG. 1: Schematic sequence and key data of an embodiment of a process in accordance with the present invention. Non-PEGylated starting material is used in two further cycles without supplementing with fresh EPO. Productivity is calculated to be increased relative to a known production process for mono-PEGylated EPO (Mircera®) disclosed in WO 2009/010270, in which two CEC chromatographic columns are used. The dynamic binding capacity of the AEC material is 35 g/L (35 g of non-PEGylated protein/L resin) (a factor of 30 higher than the CEC material of the process of WO 2009/010270. The HIC column can be loaded in flow through mode with dynamic binding capacity 5 g/L (5 g of oligo-PEGylated protein/L resin) (a factor of ~4 higher than the CEC material used in the process of WO 2009/010270). Compared with the process disclosed in WO 2009/010270, the first column can be made smaller, and the combined fractions (flow-through) from the 3 cycles can be processed in one run on a second column of equal size.

Embodiments and experiments illustrating the principles of the invention will now be discussed with reference to the accompanying figures.

Mono-PEGylated Protein Compositions

The present invention relates to processes for providing mono-PEGylated protein compositions. The present invention relates to processes for providing a protein composition comprising at least 90% mono-PEGylated protein. In particular, the present invention provides processes for providing an EPO composition comprising at least 90% mono-PEGylated EPO.

In the present context, a mono-PEGylated protein composition is a composition comprising a protein, wherein a relatively high proportion of the protein present in the composition is present as mono-PEGylated protein. A mono-PEGylated protein composition may comprises at least about 90%, 95%, 96%, 97%, 98%, 99%, 99.5%, 99.9% or 99.99% mono-PEGylated protein A protein composition comprising at least x % mono-PEGylated protein refers to a protein composition in which at least x % of the protein present in that composition is mono-PEGylated. For example, a protein composition comprising at least 99% mono-PEGylated protein is a protein composition in which at least 99% of that protein present in the composition is mono-PEGylated. Protein compositions produced by the processes of the invention may comprise at least about 90%, at least about 95%, 96%, 97%, 98%, 99%, 99.5%, 99.9% or 99.99% mono-PEGylated protein.

In particular, in the present context, a mono-PEGylated EPO composition is a composition comprising EPO, wherein a relatively high proportion of the EPO present in the composition is present as mono-PEGylated EPO. An EPO composition comprising at least "x %" mono-PEGylated EPO refers to an EPO composition in which at least "x %" of the EPO present in that composition is mono-PEGylated. For example, an EPO composition comprising at least 99% mono-PEGylated EPO is an EPO composition in which at least 99% of the EPO present in the composition is mono-PEGylated. EPO compositions produced by the processes of the invention may comprise at least about 90%, at least about 95%, 96%, 97%, 98%, 99%, 99.5%, 99.9%, or 99.99% mono-PEGylated EPO. EPO compositions produced by the processes of the invention may comprise at least about 98% mono-PEGylated EPO. EPO compositions produced by the processes of the invention may comprise at least about 99% mono-PEGylated EPO.

Methods for the determination of purity are known to those of skill in the art. Purity of a non-PEGylated, mono-PEGylated or oligo-PEGylated protein may be determined by any suitable method of analysis (e.g. band intensity on gel, ELISA, HPLC and the like). Determination of purity may involve using a standard curve generated using a reference material of known purity. Purity may also be determined on a weight-by-weight basis. The purity of a non-PEGylated or PEGylated protein expressed herein in percentage terms (%) may be determined for example using relative "area under the curve" values, which can typically be obtained for peaks in a chromatogram, such as an HPLC chromatogram. Methods of determining purity include RP-HPLC and size exclusion chromatography (SEC).

Chromatography

The "isoelectric point" or "pI" of a protein is the pH at which the protein has zero net overall charge. That is, the pI of a protein is the pH at which the protein has an equal number of positive and negative charges. Determination of the pI for any given protein can be done according to well-established techniques, such as isoelectric focusing. The pI of EPO is in the range 4.0 to 5.5. Alternative methods of measuring pI may give slightly different values, for example microchip isoelectric focusing gives an apparent pI of about 3.5-4.0 (VIckova 2008). The precise pI of EPO may depend for example on the degree of glycosylation and sialic acid residues, or the existence of charge variants, which may in turn depend on the means by which it has been produced (e.g. host cells used for recombinant expression).

Ion exchange chromatography separates molecules on the basis of differences in their net surface charge. It can be used to separate protein molecules. In ion exchange chromatography a mixture including a protein of interest may be passed over an ion exchange material, which carries a charge. When the ion exchange material has a negative charge the process is termed cation exchange chromatography (CEC), and when it has a positive charge the process is termed anion exchange chromatography (AEC). The protein of interest may be separated from the remainder of the mixture by manipulating charge-based interactions between the protein and the ion exchange material. This is typically done by manipulating the ionic strength, or conductivity, of the mixture and or of buffers passed over the ion exchange material.

The term ion exchange chromatography (IEC) used herein may refer to cation exchange chromatography (CEC), or anion exchange chromatography (AEC). Where a process involves multiple IEC steps, they are either all AEC steps or all CEC steps. Likewise reference to an IEC flow-through solution or an IEC material may refer to either CEC or an AEC flow-through solution, and to a CEC or an AEC material. Where a process involves an IEC step which is an AEC step, all IEC steps are AEC steps, the IEC materials is an AEC materials, the IEC flow-through solution is an AEC flow-through solution, any IEC eluate is an AEC eluate. Where a process involves an IEC step which is a CEC step, the IEC step is a CEC step, the IEC materials is a CEC material, the IEC flow-through solution is a CEC flow-through solution, and any IEC eluate is a CEC eluate.

For example, a mixture containing a protein of interest may be loaded onto an ion exchange material. The loading conditions (and wash conditions, if used) are selected to promote binding of only certain components of the mixture to the ion exchange material.

For example the loading conditions may promote binding of the protein of interest to the ion exchange material, and ion exchange material may then be washed with a wash buffer, to remove unwanted components of the mixture (e.g. contaminants), and finally the protein of interest may be eluted (removed from the ion exchange material) by increasing the ionic strength (conductivity) of the buffer. This type of procedure is known as "bind and elute" mode, because the protein of interest is bound to ion exchange material and then eluted. The solution that comes off the matrix in the elution step and contains the protein of interest may be known as the eluant or eluate.

Alternatively, the loading conditions may promote binding of unwanted components of the mixture (e.g. contaminants). In this mode, the protein of interest may flow through a matrix of the ion exchange material and be collected. This type of procedure is known as "flow through" mode. The composition that is collected after flowing through a matrix of ion exchange material is the "flow-through" or "flow-through solution". The flow-through solution that comes off the matrix and contains the protein of interest may also be termed "effluent". Unlike "bind and elute" mode, which involves a change in conductivity and/or pH to elute the protein of interest from the column, "flow through" mode is carried out under isocratic conditions. The flow-through solution may be collected as fractions, which may be pooled to provide a flow-through pool. Proteins, such as EPO, are comprised of amino acids which include acidic and basic residues. At low pH (high H$^+$ concentration) the carboxylic acid groups of proteins tend to be uncharged (—COOH) and their nitrogen-containing basic groups fully charged (—NH$_3^+$) giving most proteins a net positive charge. At high pH the carboxylic acid groups are negatively charged (—COO—) and the basic groups tend to be uncharged (—NH2), giving most proteins a net negative charge.

The isoelectric point (pI) of a protein is the pH at which that protein has no net charge because the positive and negative charges balance.

Ion exchange chromatography takes advantage of the fact that the relationship between net surface charge and pH is unique for a particular protein. At a pH below its isoelectric point a protein will have an overall positive charge and will therefore bind to a negatively charged material (i.e. in CEC). At a pH above its isoelectric point a protein will have an overall negative charge and therefore will bind to a positively charged material (i.e. in AEC).

This is why in AEC protein mixtures (load compositions) and wash buffers of a relatively high pH are generally used, in order that the protein of interest (or contaminant, e.g. unwanted protein) has a net negative charge and therefore binds to the positively charged anion exchange material. When a protein of interest is bound to the anion exchange material, it may optionally be washed to remove contaminants, and can then be eluted. When a contaminant (such as unwanted protein) is bound to the anion exchange material it is removed from the mixture, thereby purifying one or more proteins of interest in the flow-through.

Hydrophobic interaction chromatography (HIC) separates molecules on the basis of differences in their surface hydrophobicity. It can be used to separate protein molecules. In HIC a mixture including a protein of interest may be passed over an HIC material. The interaction between proteins and a HIC material is altered by the presence of certain salts. Increasing the salt concentration increases the interaction and reducing the salt concentration reduces the interaction. For selective elution, the salt concentration may be lowered and the components of the mixture elute in order of hydrophobicity, the most hydrophobic components eluting last. HIC may be performed in flow through mode or in bind and elute mode as described for ion exchange chromatography above.

A chromatography "material" in the present context, such as an anion exchange material or a HIC material, refers to the stationary phase or solid phase. This may also be referred to as a resin or matrix. The "material" in this context provides a matrix to which a component of a mixture, such as protein of interest, may bind. The material may be or may comprise a column, for example an expanded bed or packed bed column. The material may be in the form of discrete particles or beads. The material may in the form of a membrane. In the present context the mobile phase flows through the stationary phase and carries the substances to be separated by chromatography with it. The mobile phase is a mixture, such as a first or second mixture, or a solution such as a flow through solution. A buffer, such as an elution buffer or wash buffer, is also a mobile phase.

In the present context the term "loading" refers to a step of contacting a mixture or composition onto chromatography material. The chromatography material may be equilibrated before the loading step.

Equilibration involves applying an equilibration buffer to the chromatography material. The pH, ionic strength, conductivity, and/or salt concentration of the equilibration buffer are selected to ensure that when a protein mixture is loaded onto the chromatography matrix, the desired binding and/or flow through or specific proteins or contaminants is achieved.

Elution from a chromatography material, such an anion exchange material or a cation exchange material or a hydrophobic interaction material, may be achieved by changing the ionic strength, pH, conductivity, or salt concentration of a buffer using gradient elution or step elution. Gradient elution, or linear gradient elution, may be used when many components of individual interest are bound to the material and may be eluted differently, and for high resolution separation. Step elution is useful for removing a single component (or removing a specific group of components together) from a chromatography material. Step elution is relatively fast, and consumes less buffer. Step elution may be used to elute a protein of interest from a chromatography material in a relatively concentrated form. A rising gradient of ionic strength is commonly used for elution in AEC. A falling gradient of salt concentration is commonly used for elution in HIC.

Producing a Mono-PEGylated Protein Composition

The present invention provides a process for producing a mono-PEGylated protein composition.

Compared with prior art processes using CEC to provide a mono-PEGylated protein composition, the processes disclosed herein are more productive. A prior art process for production of mono-PEGylated EPO is described in WO 2009/010270.

The present invention provides a process for producing a PEGylated protein mixture, the process comprising: a) reacting a non-PEGylated protein with a PEGylation reagent to produce a mixture of reaction products comprising non-PEGylated protein and PEGylated protein, wherein the PEGylated protein comprises mono-PEGylated protein and oligo-PEGylated protein; (b) subjecting the mixture of reaction products to an anion exchange chromatography (AEC) step to provide an AEC flow-through solution in which the fraction of PEGylated protein is increased relative to the mixture of reaction products; the AEC step comprising applying the mixture of reaction products to an AEC material under conditions suitable for binding non-PEGylated protein; and (c) collecting the AEC flow-through solution from step b) to provide a PEGylated protein mixture comprising mono-PEGylated protein and oligo-PEGylated protein, wherein non-PEGylated protein is recovered in step b) by eluting an AEC eluate from the AEC material and the eluted non-PEGylated protein is used in a subsequent PEGylation reaction.

The mixture of reaction products comprising non-PEGylated protein and PEGylated protein produced by reacting a non-PEGylated protein with a PEGylation reagent may also be referred to herein as a "first mixture". The PEGylated protein mixture comprising mono-PEGylated protein and oligo-PEGylated protein produced by this method may also be referred to herein as a "second mixture".

The present invention also provides a process for producing a mono-PEGylated protein composition comprising at least about 90% mono-PEGylated protein, the process comprising: subjecting the PEGylated protein mixture comprising mono-PEGylated protein and oligo-PEGylated protein produced by the process described above to a purification process separating mono-PEGylated protein and oligo-PEGylated protein; and recovering a mono-PEGylated protein composition in which the fraction of mono-PEGylated protein is increased relative to the PEGylated protein mixture, wherein the mono-PEGylated protein composition comprises at least about 90% mono-PEGylated protein.

The present invention provides a process for producing a protein composition comprising at least about 90% mono-PEGylated protein, the process comprising: (a) providing a first mixture comprising non-PEGylated protein and PEGylated protein, wherein the PEGylated protein comprises mono-PEGylated protein and oligo-PEGylated protein (b) subjecting the first mixture to an anion exchange chromatography (AEC) step to provide an AEC flow-through solution in which the fraction of PEGylated protein is increased relative to the first mixture; the AEC step comprising applying the first mixture to an AEC material under conditions suitable for binding non-PEGylated protein; (c) collecting the AEC flow-through solution from step b) to provide a second mixture comprising mono-PEGylated protein and oligo-PEGylated protein; and (d) subjecting the second mixture to a hydrophobic interaction chromatography (HIC) step to provide a protein composition in which the fraction of mono-PEGylated protein is increased relative to the second mixture, wherein the protein composition comprises at least about 90% mono-PEGylated protein.

Figure 2:
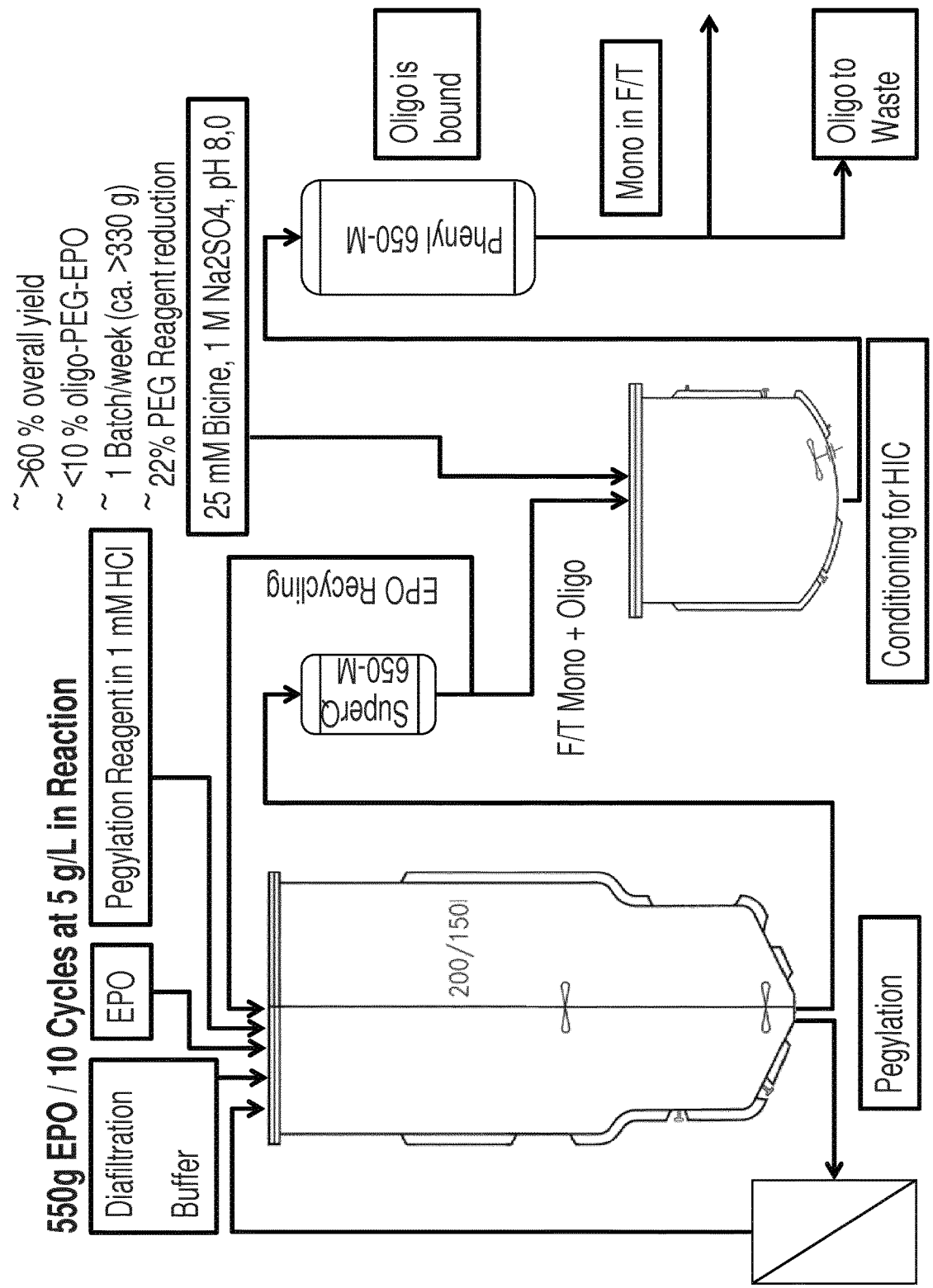
FIG. 2: Schematic sequence and key data of an embodiment of a process in accordance with the present invention. The batch size is increased by replacing the reacted EPO with an identical quantity of fresh EPO for the subsequent cycle. The number of cycles can be varied here as desired. Here the batch size was selected such that it can be completed in one week. The calculated productivity is increased by a factor of 10 relative to a known production process for mono-PEGylated EPO disclosed in WO 2009/010270.
Figure 3:
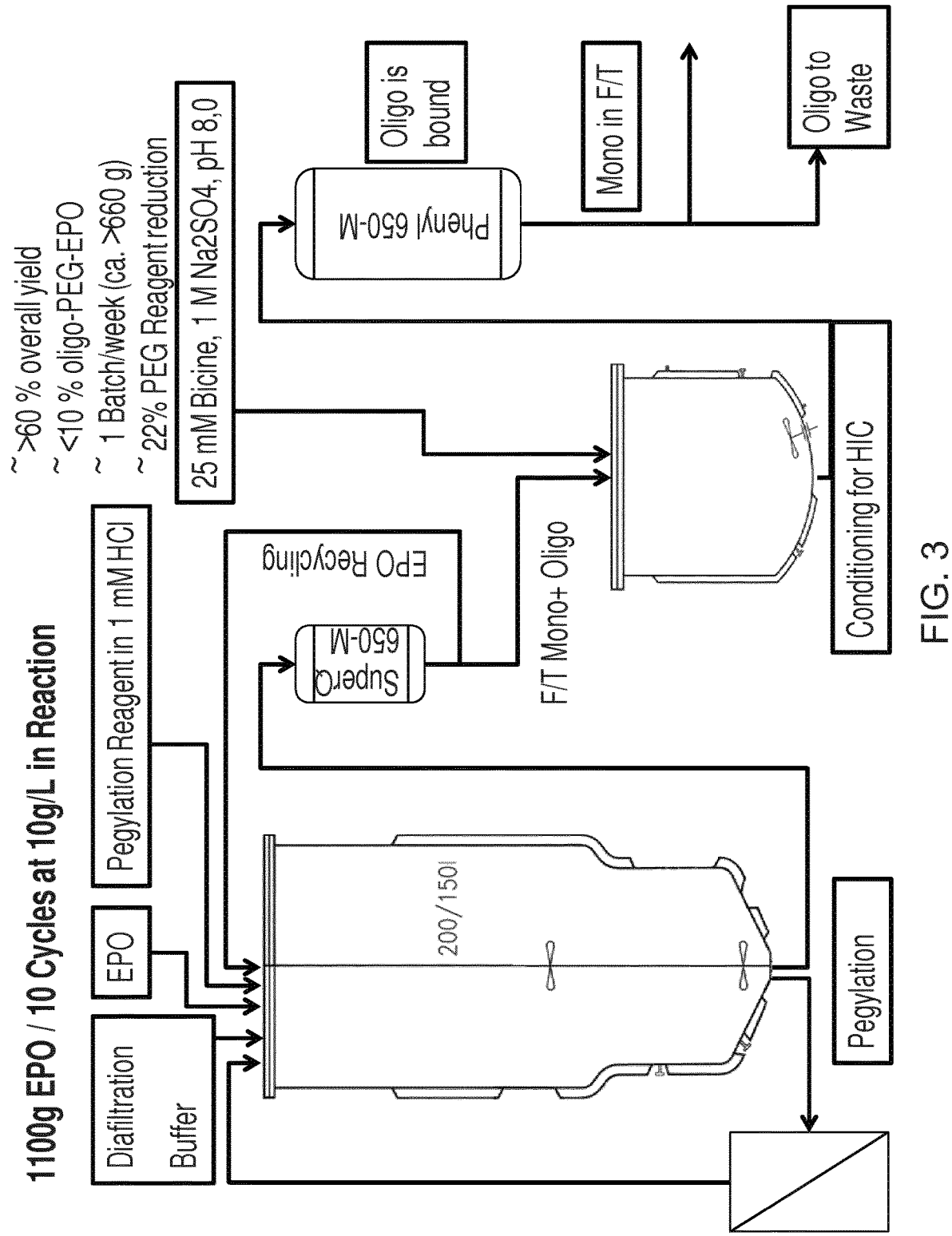
FIG. 3: Schematic sequence and key data of an embodiment of a process in accordance with the present invention. The batch size is increased because the EPO consumed in the PEGylation reaction is replaced with an identical quantity of fresh EPO in the next cycle. In addition, the concentration of the EPO for the PEGylation reaction was increased to 10 g/L. In this way, twice the quantity can be processed at the same reaction volume. The number of cycles can be varied as desired in this case. Here the batch size was selected such that it can be completed in one week. Productivity is calculated to be increased by a factor of 20 relative to a known production process for mono-PEGylated EPO disclosed in WO 2009/010270.

FIGS. 1 to 3 show embodiments of processes in accordance with the present disclosure.

Producing a Mixture of Reaction Products

The processes of the invention comprise providing a mixture of reaction products (step a). The processes of the invention are performed using a mixture of reaction products (or "first mixture") that comprises non-PEGylated, mono-PEGylated and oligo-PEGylated protein. The mixture of reaction products comprises non-PEGylated protein and PEGylated protein, wherein the PEGylated protein comprises mono-PEGylated protein and oligo-PEGylated protein. The protein may be EPO.

The processes of the invention are performed using a mixture of reaction products (or "first mixture") that comprises non-PEGylated, mono-PEGylated and oligo-PEGylated protein, wherein the proportion of oligo-PEGylated protein is relatively low. The mixture of reaction products may comprise less than about 25%, 20%, 15%, 10%, 5%, 4%, 3%, 2%, or 1% oligo-PEGylated protein, the oligo-PEGylated protein may be oligo-PEGylated EPO. The mixture of reaction products may comprise less than about 10% oligo-PEGylated protein. The mixture of reaction products may comprise less than about 10% oligo-PEGylated EPO.

The mixture of reaction products (or "first mixture") may comprise at least about 20%, 30%, 40%, 45%, 50%, 55%, 60% or 70% non-PEGylated protein. The mixture of reaction products may comprise about 20-70%, 40-60%, 45-55% non-PEGylated protein.

The mixture of reaction products (or "first mixture") may comprise at least about 30%, 40%, 45%, 50%, 55%, 60% or 70% mono-PEGylated protein. The mixture of reaction products may comprise about 30-70%, 40-60%, or 45-55% mono-PEGylated protein.

The mixture of reaction products (or "first mixture") may comprise (A) non-PEGylated protein in the range 40-60%, and (B) mono-PEGylated protein in the range 40-60%, and (C) oligo-PEGylated protein in the range 1-10%, wherein the total of (A), (B) and (C) is 100%. The mixture of reaction products may comprise (A) non-PEGylated protein in the range 45-55%, and (B) mono-PEGylated protein in the range 45-55%, and (C) oligo-PEGylated protein in the range 1-5%, wherein the total of (A), (B) and (C) is 100%.

The mixture of reaction products (or "first mixture") may comprise (A) non-PEGylated protein, and (B) mono-PEGylated protein, and (C) oligo-PEGylated protein. The non-PEGylated protein, mono-PEGylated protein, and oligo-PEGylated protein may be present in the ratio A:B:C, wherein A is about 40-60, B is about 30-50, and C is about 1-10; or wherein A is about 45-55, B is about 35-45, and C is about 1-10; or wherein A is about 35-55, B is about 35-45, and C is about 1-25. The non-PEGylated protein, mono-PEGylated protein, and oligo-PEGylated protein may be present in the ratio (A+B):C wherein (A+B):C is about 19:1; about 9:1 or about 9-19:1.

The ratio may be a weight or mass ratio. The ratio may be a molar ratio.

The mixture of reaction products (or "first mixture") is provided by performing a PEGylation reaction. Performing a PEGylation reaction involves reacting the protein (which may be the non-PEGylated protein) with a PEGylation reagent. The protein may be EPO. The PEGylation reaction may be performed as described above in relation to PEGylation of EPO. The PEGylation reaction may be performed at a pH of about 7.0 to 9.0, wherein the PEG/protein molar ration is about 0.6-1.0.

The PEGylation reaction may be performed at a pH of about 7.0 to 9.0, or about 7.5 to 8.5, or about 8.0. The PEGylation reaction may be performed at a pH of about 7.0 to 9.0, or about 7.5 to 8.5, or about 8.0 using (NHS) activated PEG reagent. The pH at which the PEGylation reaction is performed may depend on the PEG reagent used. The PEG reagent may be mPEG-NHS, mPEG-SPA, mPEG-SVA or mPEG-CI. The relationship between PEGylation reaction rates and pH is reviewed in Pfister 2016. Other reagents for PEGylation reactions are known in the art.

The molar ratio of PEG/protein in the PEGylation reaction may be $1.0. The molar ratio of PEG/protein in the PEGylation reaction may be about 0.8. The PEG/protein molar ratio may be about 0.25 to 1.0, 0.3 to 1.0, 0.4 to 1.0, 0.5 to 1.0, 0.6 to 1.0 or 0.7 to 1.0. The PEG/protein molar ratio may be about 0.25 to 1.2, 0.3 to 1.2, 0.4 to 1.2, 0.5 to 1.2, 0.6 to 1.2 or 0.7 to 1.2. The PEG/protein molar ration may be about 0.25 to 1.5, 0.3 to 1.5, 0.4 to 1.5, 0.5 to 1.5, 0.6 to 1.5 or 0.7 to 1.5. The PEG/protein molar ratio may have a lower limit of about 0.4, 0.5, 0.6 or 0.7 and may have an upper limit of 0.8. 0.9. 1.0. 1.1. 1.2. 1.3. 1.4. or 1.5.

Ion Exchange Chromatography

The first mixture is subjected to an ion exchange chromatography (AEC) step (step b). This provides an IEC flow-through solution in which the fraction of PEGylated protein is increased relative to the first mixture. This provides an IEC flow-through solution in which the fraction of non-PEGylated protein is decreased relative to the first mixture. The IEC step may be an AEC step or a CEC step.

Anion Exchange Chromatography

The mixture of reaction products (or "first mixture") may be subjected to an anion exchange chromatography (AEC) step (step b). This provides an AEC flow-through solution in which the fraction of PEGylated protein is increased relative to the mixture of reaction products. This provides an AEC flow-through solution in which the fraction of non-PEGylated protein is decreased relative to the mixture of reaction products.

In the context of the present disclosure a fraction which is increased may be increased by an amount of at least about 5%, 10%, 20%, 30%, 40%, 50%, 60%, 70%, 80%, 90% or 100%. A fraction which is increased may be increased by at least about 1.5-fold, 2-fold, 3-fold, 5-fold or 10-fold.

In the context of the present disclosure a fraction which is decreased may be decreased by an amount of at least about 5%, 10%, 20%, 30%, 40%, 50%, 60%, 70%, 80%, 90% or 100%. A fraction which is decreased may be increased by at least about 1.5-fold, 2-fold, 3-fold, 5-fold or 10-fold.

The AEC step comprises contacting the mixture of reaction products with an anion exchange material, or applying the mixture of reaction products to an anion exchange material. The AEC step may comprise loading the mixture of reaction products onto a column comprising an anion exchange material. The anion exchange material has a low binding capacity for PEGylated protein, such as PEGylated EPO. That is, the AEC material has a relatively low binding capacity for the PEGylated version of the protein species for which a mono-PEGylated composition is desired. AEC conditions are used which are suitable for binding of the non-PEGylated protein to the anion exchange material. The solution that flows through the anion exchange material is the AEC flow-through solution. The low binding capacity of the anion exchange material for PEGylated protein has the effect that most of the PEGylated protein flows through the anion exchange material and is therefore present in the AEC flow-through solution. The binding conditions suitable for binding of the non-PEGylated protein to the anion exchange material have the effect that most of the non-PEGylated protein is removed (by binding to the anion exchange material) and is not present in the flow-through solution.

The AEC material may be a material that does not significantly bind PEGylated protein. This may mean that the AEC material binds less than about 10%, 5%, 2%, 1%, 0.5%, 0.1% or 0.01% of the PEGylated protein that is applied to it. Binding of PEGylated protein to the anion exchange material can also be reduced by applying high amounts of non-PEGylated protein to the anion exchange material. In this way, bound PEGylated protein is displaced by non-PEGylated protein. The amount of non-PEGylated protein applied to the anion exchange material may be about 20%, 30%, 40%, 50%, 60%, 70%, 80%, 90%, 100%, 110% or 120% of the dynamic break through capacity of the anion exchange material. The amount of non-PEGylated protein applied to the anion exchange material may be in the range of about 70-110%, about 80-100%, or about 85-95% of the dynamic break through capacity of the anion exchange material. The amount of non-PEGylated protein applied to the anion exchange material may be in the range of about 80-95% of the dynamic break through capacity of the anion exchange material.

The AEC flow-through solution comprises mono-PEGylated and oligo-PEGylated protein. The AEC flow-through solution may also comprise non-PEGylated protein, wherein the proportion of non-PEGylated protein is relatively low or close to zero. The AEC flow-through solution may comprise zero non-PEGylated protein, or amounts of non-PEGylated protein below the limit of detection. The protein may be EPO. The flow-through solution may comprise less than about 20%, 15%, 10%, 5%, 4%, 3%, 2%, 1.5%, 1.0%, 0.5% or 0.1% non-PEGylated protein. The flow-through solution may comprise less than about 2% non-PEGylated protein. The flow-through solution may comprise less than about 2% non-PEGylated EPO.

The AEC flow-through solution may comprise at least about 80%, 85%, 90% 95%, 96%, 97%, 98%, 99% or at least about 99.9% PEGylated protein.

The AEC flow-through may comprise about 80% mono-PEGylated protein and about 20% oligo-PEGylated protein. The AEC flow-through solution may comprise at least about 60%, 65%, 70%, 75%, or 80% mono-PEGylated protein. The flow-through solution may comprise about 60-90%, 70-90%, or 75-85% mono-PEGylated protein. The AEC flow-through solution may comprise at least about 20%, 25%, 30%, 35%, or 40% oligo-PEGylated protein. The flow-through solution may comprise about 10-40%, 10-30%, or 15-25% oligo-PEGylated protein.

The AEC flow-through solution may comprise (A) non-PEGylated protein in the range 0.1-5%, and (B) mono-PEGylated protein in the range 60-90%, and (C) oligo-PEGylated protein in the range 10-40%, wherein the total of (A), (B) and (C) is 100%. The flow-through solution may comprise (A) non-PEGylated protein in the range 0.1-1.5%, and (B) mono-PEGylated protein in the range 75-85%, and (C) oligo-PEGylated protein in the range 15-25%, wherein the total of (A), (B) and (C) is 100%.

The AEC flow-through solution may comprise (A) non-PEGylated protein, and (B) mono-PEGylated protein, and (C) oligo-PEGylated protein. The non-PEGylated protein, mono-PEGylated protein, and oligo-PEGylated protein may be present in the ratio A:B:C, wherein A is about 1-5, B is about 10-20, and C is about 5-15; or wherein A is about 1-3, B is about 25-35 and C is about 5-10. The non-PEGylated protein, mono-PEGylated protein, and oligo-PEGylated protein may be present in the ratio A:(B+C) wherein A:(B+C) is about 1:25; 1:50; 1:100; about 1:150, about 1:200, or about 1:100-200. The ratio may be a weight or mass ratio. The ratio may be a molar ratio.

The AEC step is performed under conditions suitable for non-PEGylated protein to bind to the AEC material. Conditions suitable for non-PEGylated protein binding may be determined empirically by screening one or more of the AEC material, or the pH, conductivity, salt content or buffer content of the equilibration buffer.

The functional groups on an ion exchange material determine its charge. The terms "strong" and "weak" in this context refer to the extent that the ionisation state of the functional groups varies with varying pH. Strong ion exchangers show little or no variation in ion exchange capacity with change in pH. Strong ion exchangers remain fully charged over a broad pH range. Weak ion exchangers display pH-dependent function and deliver optimal performance over a narrower pH range.

Strong anionic exchange materials may include a quaternary ammonium group (Q), or a quaternary amino ethyl group (QAE). A weak anionic exchange material may include diethylaminoethyl residues (DEAE). An advantage of using strong anionic exchange materials is that the binding capacity is maintained at high or low pH since there is no loss of charge.

AEC materials may comprise a resin that has been functionalised with a positively charged ligand or functional group, that is, with a basic ligand or functional group.

The anion exchange material used in the processes of the invention may be a strong anion exchange material. The anion exchange material is preferably a strong anion exchange material. It may have a quaternary ammonium group (Q). It may be a hydroxylated polymethacrylic polymer bead functionalised with a Q groups. It may have a 50-150 nm, 70-120 nm, 70-100 nm or a 90-110 nm pore size. Pore size herein may refer to mean pore size. It may have a particle size of 40-150 μm, 40-120 μm, 40-100 μm, 40-80 μm, or about 60, 65, 70, 80, or 90 100 μm. Particle size (or bead size) may refer to mean particle size. It may have a 70-100 nm pore size and a 35-100 μm bead size. It may have a 100 nm pore size and a 65 μm bead size. It may be Toyopearl Super Q 650M (Tosoh Bioscience LLC; product number 43205). The anion exchange material used in the processes of the invention may be used in accordance with the manufacturer's instructions.

The anion exchange material used in the processes of the invention may be a weak anion exchange material. It may have tertiary and/or secondary amine functional groups. It may not have primary amine functional groups. It may have only one type of amine group or may have two or more types of amine group.

The anion exchange material may be or may comprise a column, for example an expanded bed or packed bed column. The anion exchange material may be or may comprise a continuous countercurrent tangential chromatography system. The anion exchange material may be in the form of discrete particles or beads. The anion exchange material may be in the form of a membrane. The anion exchange material may be in the form of a functionalised filter, or a functionalised fibre, fleece, or mesh. The anion exchange material may be in the form of any other solid support able to carry functional groups or exhibiting anion exchange properties.

Examples of anion exchangers include Toyopearl Super Q 650C, Toyopearl Super Q 650S, Toyopearl GigaCap Q 650M, GigaCap Q 650S, Toyopearl Q-600C AR, Toyopearl DEAE 650S, Toyopearl DEAE 650M and Toyopearl DEAE 650C, Toyopearl Super Q 650, Toyopearl Super Q 650 QAE, Toyopearl Super Q 550C, Macroprep High Q, Fractoprep TMAE, Q Hyper DF, Capto Q, Q-Sepharose FF, Q-Sepharose BB, Q-Sepharose XL, Q-Sepharose HP, MiniQ, MonoQ, MonoP, DEAE Sepharose FF, Source SQ, Source 30Q, ANX Sepharose 4 FF (high sub), Streamline DEAE, Streamline QXL, Poros HQ, Poros PI, Poros D, DEAEHyperD, Q Ceramic Hyper D, Fractogel DMAE.

The AEC material in the processes of the invention may be an anion exchange material having a low binding capacity for the PEGylated form of the protein. In particular, it may be an anion exchange material having low binding capacity for PEGylated EPO. The anion exchange material may be Toyopearl Super Q 650 M having low binding capacity for PEGylated EPO, for example a binding capacity of less than about 0.5 g/L, 0.05 g/L, 0.01 g/L or 0.001 g/L, or close to 0 g/L. The anion exchange material may be an anion exchange material having substantially the same binding capacity for PEGylated EPO as Toyopearl Super Q 650 M equilibrated with 25 mM bicine, 7.5 mM $Na_2SO_4$, at pH 8.0.

The AEC material may have a relatively high binding capacity for non-PEGylated protein, e.g. non-PEGylated EPO, of 20-50 g/L, 30-40 g/L, or about 35 g/L. The AEC material may have a binding capacity for non-PEGylated protein, e.g. non-PEGylated EPO, of at least about 35 g/L.

An anion exchange material may be equilibrated before the mixture of reaction products (or "first mixture") is applied to it. An AEC equilibration buffer may comprise a salt such as $Na_2SO_4$ and/or bicine. An AEC equilibration buffer may comprise a phosphate salt. An AEC equilibration buffer may not comprise compounds having primary amine groups, for example tris(hydroxymethyl)aminomethane (Tris). An AEC equilibration buffer may have a pH of about 6.5 to 9.5, 7.0 to 9.0, 7.5 to 8.5, or 8.0. An AEC equilibration buffer may comprise about 10-40 mM, 15-35 mM, 20-30 mM bicine or about 25 mM bicine. An AEC equilibration buffer may comprise may comprise about 1-20 mM, 1-10 mM, 2.5-10 mM, 5-10 mM salt or about 7.5 mM salt. An equilibration buffer for use in AEC may comprise about 25 mM bicine, about 7.5 mM $Na_2SO_4$, pH 8.0. An equilibration buffer may have a conductivity of about 1 to about 8 mS/cm, about 1 to about 5 mS/cm, about 1.5 to about 3.0 mS/cm, about 2.0 to about 3.0 mS/cm, or about 1.0 to 3.0 mS/cm. If the mixture of reaction products has a conductivity outside the conductivity range of the equilibration buffer, then it may be conditioned (for example by addition of salt and/or buffer) to provide a mixture of reaction products having a conductivity that is within the conductivity range of the equilibration buffer, or is within 0.5 mS/cm or 0.05 mS/cm of the equilibration buffer.

The mixture of reaction products (or "first mixture"), comprising non-PEGylated, mono-PEGylated and oligo-PEGylated protein may be conditioned to provide a mixture of reaction products which has the pH, buffer and salt values set out above for the equilibration buffer. A conditioned mixture of reaction products may also be referred to as an AEC load composition or load solution. An AEC load solution may be an aqueous solution of non-PEGylated, mono-PEGylated and oligo-PEGylated protein in about 10-30 mM bicine, about 5.0-10.0 mM $Na_2SO_4$, PH 7.0-9.0. An AEC load solution may be an aqueous solution of non-PEGylated, mono-PEGylated and oligo-PEGylated protein in about 25 mM bicine, about 7.5 mM $Na_2SO_4$, PH 8.0.

The AEC step may be performed at a pH at least 1.0 to 2.0 pH units above the pI of the protein. Many proteins have a pI in the range 5.5 to 7.5 and therefore the processes of the invention may be used for producing a mono-PEGylated protein wherein the AEC step is performed at pH of about 6.5 to 9.5, or 6.5 to 8.5, or 7.5 to 8.5.

The pI of EPO is in the range 4.0 to 5.5. Processes in which the protein is EPO are may be performed at least 2.0, 2.5, or 3.0 pH units above the pI of the protein. This enables efficient EPO binding to the AEC material. Processes for producing a mono-PEGylated EPO composition may involve an AEC step performed at a pH of at least about 7.0, or about pH 7.0 to 10.0, or pH 7.0 to 9.0. The pH may be about 7.5 to 8.5, or about 7.8 to 8.2, or about 8.0.

The AEC step may be performed at a conductivity of about 1.0-3.0 mS/cm, 1.5-2.5 mS/cm or about 2.2 mS/cm. The conductivity of the AEC step may be adjusted by adjusting the concentration of a salt, such as NaCl or $Na_2SO_4$ in the AEC equilibration buffer or AEC wash buffer. The AEC step may be performed at $Na_2SO_4$ concentration of about 5.0-15 mM, 5.0-10 mM, or about 7.5 mM. The AEC step may be performed using other salts, at concentrations that provide ionic strengths equivalent to those mentioned here for $Na_2SO_4$.

After the mixture of reaction products (or "first mixture"), or AEC load solution, has been applied to the AEC material, the AEC material may be washed. The AEC material may be washed with equilibration buffer. The AEC material may be washed with a wash buffer. A wash buffer may comprise about 10-40 mM, 15-35 mM, 20-30 mM bicine or about 25 mM bicine. A wash buffer may comprise may comprise about 1-20 mM, 1-10 mM, 2.5-10 mM, 5-10 mM salt or about 7.5 mM salt. It may comprise about 25 mM bicine, about 7.5 mM $Na_2SO_4$, pH 8.0. A wash buffer may have a conductivity of about 1 to about 8 mS/cm, about 1 to about 5 mS/cm, about 1.5 to about 3.0 mS/cm, about 2.0 to about 3.0 mS/cm. The AEC material may be washed with 1 to 10, 1 to 5, or about 1, 2, 3, 4, or 5 column volumes of equilibration buffer or wash buffer. The AEC material may be washed with a volume of equilibration buffer or wash buffer that is determined by monitoring protein content of the flow-through solution (e.g. by UV spectrometry) and stopping the wash process once the protein content is below a threshold value (e.g. when UV signal returns to baseline). The flow-through solution, or effluent, may be collected as fractions, and some or all of these flow-through fractions may be pooled.

Processes involving anion exchange chromatography are particularly preferred for production of mono-PEGylated EPO because they allow use of relatively high pH conditions under which EPO is relatively stable.

The process of the invention may comprise an AEC step wherein the AEC material is Toyopearl Super Q 650 M; the AEC step is performed at pH of about 7.0 to 9.0; the AEC step is performed at a conductivity of about 1.0 to 3.0 mS/cm; and the first mixture is applied to the AEC material as a AEC load solution comprising about 10-30 mM bicine and about 1-10 mM $Na_2SO_4$. The protein may be erythropoietin.

Cation Exchange Chromatography

The IEC step may be a CEC step. The first mixture may be subjected to a cation exchange chromatography (CEC) step (step b). This provides an CEC flow-through solution in which the fraction of PEGylated protein is increased relative to the first mixture. This provides an CEC flow-through solution in which the fraction of non-PEGylated protein is decreased relative to the first mixture.

In the context of the present disclosure a fraction which is increased may be increased by an amount of at least about 5%, 10%, 20%, 30%, 40%, 50%, 60%, 70%, 80%, 90% or 100%. A fraction which is increased may be increased by at least about 1.5-fold, 2-fold, 3-fold, 5-fold or 10-fold.

In the context of the present disclosure a fraction which is decreased may be decreased by an amount of at least about 5%, 10%, 20%, 30%, 40%, 50%, 60%, 70%, 80%, 90% or 100%. A fraction which is decreased may be increased by at least about 1.5-fold, 2-fold, 3-fold, 5-fold or 10-fold.

A CEC step comprises contacting the first mixture with a cation exchange material, or applying the first mixture to an cation exchange material. The CEC step may comprise loading the first mixture onto a column comprising a cation exchange material. The cation exchange material has a low binding capacity for PEGylated protein, such as PEGylated EPO. That is, the CEC material has a relatively low binding capacity for the PEGylated version of the protein species for which a mono-PEGylated composition is desired. CEC conditions are used which are suitable for binding of the non-PEGylated protein to the cation exchange material. The solution that flows through the cation exchange material is the CEC flow-through solution. The low binding capacity of the cation exchange material for PEGylated protein has the effect that most of the PEGylated protein flows through the cation exchange material and is therefore present in the CEC flow-through solution. The binding conditions suitable for binding of the non-PEGylated protein to the cation exchange material have the effect that most of the non-PEGylated protein is removed (by binding to the cation exchange material) and is not present in the flow-through solution.

The CEC material may be a material that does not significantly bind PEGylated protein. This may mean that the CEC material binds less than about 10%, 5%, 2%, 1%, 0.5%, 0.1% or 0.01% of the PEGylated protein that is applied to it. Binding of PEGylated protein to the cation exchange material can also be reduced by applying high amounts of non-PEGylated protein to the cation exchange material. In this way, bound PEGylated protein is displaced by non-PEGylated protein. The amount of non-PEGylated protein applied to the cation exchange material may be about 20%, 30%, 40%, 50%, 60%, 70%, 80%, 90%, 100%, 110% or 120% of the dynamic break through capacity of the cation exchange material. The amount of non-PEGylated protein applied to the cation exchange material may be in the range of about 70-110%, about 80-100%, or about 85-95% of the dynamic break through capacity of the cation exchange material. The amount of non-PEGylated protein applied to the cation exchange material may be in the range of about 80-95% of the dynamic break through capacity of the cation exchange material.

The CEC flow-through solution comprises mono-PEGylated and oligo-PEGylated protein. The CEC flow-through solution may also comprise non-PEGylated protein, wherein the proportion of non-PEGylated protein is relatively low or close to zero. The CEC flow-through solution may comprise zero non-PEGylated protein, or amounts of non-PEGylated protein below the limit of detection. The protein may be EPO. The flow-through solution may comprise less than about 20%, 15%, 10%, 5%, 4%, 3%, 2%, 1.5%, 1.0%, 0.5% or 0.1% non-PEGylated protein. The flow-through solution may comprise less than about 2% non-PEGylated protein. The flow-through solution may comprise less than about 2% non-PEGylated EPO.

The CEC flow-through solution may comprise at least about 80%, 85%, 90% 95%, 96%, 97%, 98%, 99% or at least about 99.9% PEGylated protein.

The CEC flow-through may comprise about 80% mono-PEGylated protein and about 20% oligo-PEGylated protein. The CEC flow-through solution may comprise at least about 60%, 65%, 70%, 75%, or 80% mono-PEGylated protein. The flow-through solution may comprise about 60-90%, 70-90%, or 75-85% mono-PEGylated protein. The CEC flow-through solution may comprise at least about 20%, 25%, 30%, 35%, or 40% oligo-PEGylated protein. The flow-through solution may comprise about 10-40%, 10-30%, or 15-25% oligo-PEGylated protein.

The CEC flow-through solution may comprise (A) non-PEGylated protein in the range 0.1-5%, and (B) mono-PEGylated protein in the range 60-90%, and (C) oligo-PEGylated protein in the range 10-40%, wherein the total of (A), (B) and (C) is 100%. The flow-through solution may comprise (A) non-PEGylated protein in the range 0.1-1.5%, and (B) mono-PEGylated protein in the range 75-85%, and (C) oligo-PEGylated protein in the range 15-25%, wherein the total of (A), (B) and (C) is 100%.

The CEC flow-through solution may comprise (A) non-PEGylated protein, and (B) mono-PEGylated protein, and (C) oligo-PEGylated protein. The non-PEGylated protein, mono-PEGylated protein, and oligo-PEGylated protein may be present in the ratio A:B:C, wherein A is about 1-5, B is about 10-20, and C is about 5-15; or wherein A is about 1-3, B is about 25-35 and C is about 5-10. The non-PEGylated protein, mono-PEGylated protein, and oligo-PEGylated protein may be present in the ratio A:(B+C) wherein A:(B+C) is about 1:25; 1:50; 1:100; about 1:150, about 1:200, or about 1:100-200. The ratio may be a weight or mass ratio. The ratio may be a molar ratio.

The CEC step is performed under conditions suitable for non-PEGylated protein to bind to the CEC material. Conditions suitable for non-PEGylated protein binding may be determined empirically by screening one or more of the CEC material, or the pH, conductivity, salt content or buffer content of the equilibration buffer.

The functional groups on an ion exchange material determine its charge. The terms "strong" and "weak" in this context refer to the extent that the ionisation state of the functional groups varies with varying pH. Strong ion exchangers show little or no variation in ion exchange capacity with change in pH. Strong ion exchangers remain fully charged over a broad pH range. Weak ion exchangers display pH-dependent function and deliver optimal performance over a narrower pH range.

Strong cation exchange materials may include a sulfonic acid group. A weak cationic exchange material may include caboxylic or phosphonic acid functional groups. An advantage of using strong cationic exchange materials is that the binding capacity is maintained at high or low pH since there is no loss of charge.

CEC materials may comprise a resin that has been functionalised with a negatively charged ligand or functional group, that is, with an acidic ligand or functional group.

CEC materials include POROS HS materials, Fractogel S materials, Fractogel EMD SO3-(S), Fractogel EMD SO3-(M), Fractogel SMD SE HiCap (M), Fractogel EMD COO-(M), and Capto S materials.

The cation exchange material used in the processes of the invention may be a strong cation exchange material. It may have a 50-150 nm, 70-120 nm, 70-100 nm or a 90-110 nm pore size. Pore size herein may refer to mean pore size. It may have a particle size of 40-150 µm, 40-120 µm, 40-100 µm, 40-80 µm, or about 60, 65, 70, 80, or 90 100 µm. Particle size (or bead size) may refer to mean particle size. It may have a 70-100 nm pore size and a 35-100 µm bead size. It may have a 100 nm pore size and a 65 µm bead size. It may be SP Toyopearl 650 M.

The cation exchange material may be or may comprise a column, for example an expanded bed or packed bed column. The cation exchange material may be or may comprise a continuous countercurrent tangential chromatography system. The cation exchange material may be in the form of discrete particles or beads. The cation exchange material may be in the form of a membrane. The cation exchange material may be in the form of a functionalised filter, or a functionalised fibre, fleece, or mesh. The anion exchange material may be in the form of any other solid support able to carry functional groups or exhibiting anion exchange properties.

The CEC material in the processes of the invention may be a cation exchange material having a low binding capacity for the PEGylated form of the protein. In particular, it may be a cation exchange material having low binding capacity for PEGylated EPO. The cation exchange material may be SP Toyopearl 650 M having low binding capacity for PEGylated EPO, for example a binding capacity of less than about 0.5 g/L, 0.05 g/L, 0.01 g/L or 0.001 g/L, or close to 0 g/L.

The CEC material may have a relatively high binding capacity for non-PEGylated protein, e.g. non-PEGylated EPO, of 20-50 g/L, 30-40 g/L, or about 35 g/L. The CEC material may have a binding capacity for non-PEGylated protein, e.g. non-PEGylated EPO, of at least about 35 g/L.

Providing a PEGylated Protein Mixture Comprising Mono-PEGylated Protein and Oligo-PEGylated Protein As described above, the processes of the invention involve subjecting a mixture of reaction products ("first mixture") to an ion exchange chromatography (IEC) step (step b). The flow-through from the ion exchange chromatography step is used to provide a PEGylated protein mixture (or "second mixture") (step c). For example, the PEGylated protein mixture may comprise the collected flow-through from one or more IEC steps. The step of providing a PEGylated protein mixture may comprise providing a batch of PEGylated protein mixture to an HIC apparatus (e.g. HIC column). Alternatively, the step of providing a PEGylated protein mixture may comprise providing the flow-through to an HIC apparatus (e.g. HIC column) via an in-line connection.

The step of providing a PEGylated protein mixture (or "second mixture") (step c) comprises collecting the flow-through solution from the IEC step. The step of providing a PEGylated protein mixture may comprise pooling the flow-through solution from two, three, four or five IEC steps, or more than three IEC steps. The step of providing a PEGylated protein mixture may comprise conditioning the second mixture. Conditioning the PEGylated protein mixture may provide a conditioned PEGylated protein mixture having improved suitability for separating the mono-PEGylated protein from the oligo-PEGylated protein contained therein. Conditioning the PEGylated protein mixture may provide a conditioned PEGylated protein mixture having improved suitability for separating the mono-PEGylated protein from the oligo-PEGylated protein contained therein by HIC. A conditioned PEGylated protein mixture may be referred to as a HIC load composition or load solution. Conditioning the PEGylated protein mixture may comprise addition of salt, and/or addition of bicine.

For example, as described above, the processes of the invention involve subjecting a mixture of reaction products ("first mixture") to an anion exchange chromatography (AEC) step (step b). The flow-through from the anion exchange chromatography step is used to provide a PEGylated protein mixture (or "second mixture") (step c). For example, the PEGylated protein mixture may comprise the collected flow-through from one or more AEC steps. The step of providing a PEGylated protein mixture may comprise providing a batch of PEGylated protein mixture to an HIC apparatus (e.g. HIC column). Alternatively, the step of providing a PEGylated protein mixture may comprise providing the flow-through to an HIC apparatus (e.g. HIC column) via an in-line connection.

The step of providing a PEGylated protein mixture (or "second mixture") (step c) comprises collecting the flow-through solution from the AEC step. The step of providing a PEGylated protein mixture may comprise pooling the flow-through solution from two, three, four or five AEC steps, or more than three AEC steps. The step of providing a PEGylated protein mixture may comprise conditioning the second mixture. Conditioning the PEGylated protein mixture may provide a conditioned PEGylated protein mixture having improved suitability for separating the mono-PEGylated protein from the oligo-PEGylated protein contained therein. Conditioning the PEGylated protein mixture may provide a conditioned PEGylated protein mixture having improved suitability for separating the mono-PEGylated protein from the oligo-PEGylated protein contained therein by HIC. A conditioned PEGylated protein mixture may be referred to as a HIC load composition or load solution. Conditioning the PEGylated protein mixture may comprise addition of salt, and/or addition of bicine.

Recycling Unreacted Protein

The processes involve performing a PEGylation reaction to provide a mixture of reaction products. The non-PEGylated (unreacted) protein is recycled by including it in a subsequent PEGylation reaction. Non-PEGylated protein is recovered in step b) by eluting an IEC eluate from the IEC material. The eluted non-PEGylated protein is then used in a subsequent PEGylation reaction. The eluted non-PEGylated protein may be used in a subsequent step a) PEGylation reaction.

The processes may involve performing two or more cycles of steps a), b) and c), in which non-PEGylated protein is recovered in step b) by eluting an IEC eluate from the IEC material. The eluted non-PEGylated protein is then used in a subsequent PEGylation reaction. The eluted non-PEGylated protein may be used in a subsequent step a) PEGylation reaction. The eluted non-PEGylated protein may be used in the PEGylation reaction of step a) of the next cycle. That is, further cycles of steps a), b) and c) may be performed in which non-PEGylated protein from a previous cycle is used in the PEGylation reaction of that further cycle. Alternatively, a cycle of steps a), b) and c) may be followed by a subsequent PEGylation reaction (which may be a step a) PEGylation reaction) and a processing step which provides a solution in which the fraction of PEGylated protein is increased relative to the mixture of reaction products and which allows recovery of non-PEGylated protein. That is, cycles of steps a), b) and c) may be followed by, or alternated with, a PEGylation reaction and a processing step different to but having similar effects as the step b) IEC step. Recovered non-PEGylated protein may be used in a subsequent PEGylation reaction. Recovered non-PEGylated protein may be used in a subsequent step a) PEGylation reaction. Recovered non-PEGylated protein may be used in a subsequent cycle of steps a), b) and c).

For example, the processes involve performing a PEGylation reaction to provide a mixture of reaction products. The non-PEGylated (unreacted) protein is recycled by including it in a subsequent PEGylation reaction. Non-PEGylated protein is recovered in step b) by eluting an AEC eluate from the AEC material. The eluted non-PEGylated protein is then used in a subsequent PEGylation reaction. The eluted non-PEGylated protein may be used in a subsequent step a) PEGylation reaction.

The processes may involve performing two or more cycles of steps a), b) and c), in which non-PEGylated protein is recovered in step b) by eluting an IEC eluate from the IEC material. The eluted non-PEGylated protein is then used in a subsequent PEGylation reaction. The eluted non-PEGylated protein may be used in a subsequent step a) PEGylation reaction. The eluted non-PEGylated protein may be used in the PEGylation reaction of step a) of the next cycle. That is, further cycles of steps a), b) and c) may be performed in which non-PEGylated protein from a previous cycle is used in the PEGylation reaction of that further cycle. Alternatively, a cycle of steps a), b) and c) may be followed by a subsequent PEGylation reaction (which may be a step a) PEGylation reaction) and a processing step which provides a solution in which the fraction of PEGylated protein is increased relative to the mixture of reaction products and which allows recovery of non-PEGylated protein. That is, cycles of steps a), b) and c) may be followed by, or alternated with, a PEGylation reaction and a processing step different to but having similar effects as the step b) IEC step. Recovered non-PEGylated protein may be used in a subsequent PEGylation reaction. Recovered non-PEGylated protein may be used in a subsequent step a) PEGylation reaction. Recovered non-PEGylated protein may be used in a subsequent cycle of steps a), b) and c).

Various processing steps suitable for providing a solution in which the fraction of PEGylated protein is increased relative to the mixture of reaction products and which allow recovery of non-PEGylated protein exist and will be known to the skilled person. These include, for example, chromatographic methods such as cation exchange chromatography, ion exchange chromatography, and hydrophobic interaction chromatography.

A "cycle" as used herein refers to a full cycle of steps a), b), and c).

The processes may comprise three, four or five cycles, wherein step b) of each cycle comprises eluting non-PEGylated protein from the IEC material to provide an IEC eluate, and wherein the non-PEGylated protein eluted in step b) is used in a subsequent PEGylation reaction. The non-PEGylated protein eluted in step b) may be added to the PEGylation reaction of step a) in a subsequent cycle.

The processes may comprise pooling the non-PEGylated protein recovered in step b) from multiple IEC steps before it is used in a subsequent PEGylation reaction. The processes may comprise pooling the non-PEGylated protein recovered in step b) from multiple IEC steps before it is used in a subsequent step a) PEGylation reaction. The processes may comprise pooling the non-PEGylated protein recovered from two, three, four or five step b) IEC steps, or more than five step b) IEC steps.

The processes may comprise adding the step b) IEC eluate directly to a subsequent PEGylation reaction. The processes may comprise adding the IEC eluate from step b) of a cycle directly to the PEGylation reaction of step a) of the next cycle. For example the process may comprise adding the IEC eluate from step b) of a first cycle directly to the PEGylation reaction of step a) of the second cycle. Adding directly in this context means that no intervening step of purifying or cleaning the non-PEGylated protein in the eluate (e.g. by diafiltration or ultrafiltration). Rather, the eluate from the IEC material that contains the non-PEGylated protein is added to a subsequent PEGylation reaction.

The non-PEGylated protein used in a subsequent PEGylation reaction may be supplemented with fresh protein. The process may comprise adding fresh protein to the PEGylation reaction in addition to the non-PEGylated protein recovered from the IEC material. The step of recycling non-PEGylated protein comprises adding non-PEGylated protein recovered from the IEC material to a subsequent PEGylation reaction, and this may further comprise adding fresh protein to the PEGylation reaction such that the starting concentration of protein in the PEGylation reactions is substantially constant. Substantially constant in this context may mean that the starting concentration of protein in the second and subsequent PEGylation reactions is substantially the same as that in the first PEGylation reaction. This may mean that the starting concentration of protein in the second and subsequent PEGylation reactions is substantially the same as that in the PEGylation reaction of the first cycle. Substantially the same may mean ±10%. Fresh protein refers to protein that has not previously been subject to a PEGylation reaction.

The processes may involve cycles of steps a), b) and c), such that a first and a second cycle are performed and the second cycle is the final cycle. Alternatively the processes of the invention may involve two further cycles of steps a), b), and c), such that a first, a second and a third cycle is performed, and the third cycle is the final cycle. The processes may involve more than two further cycles of steps a), b) and c). The processes may involve a total of one, two, three, four, or five cycles of steps a), b) and c).

The final cycle may comprise performing a PEGylation reaction wherein the PEG/protein molar ratio is from about 1.4 to 1 to about 2 to 1. The molar ratio of PEG/protein may be about 1.4 to 1.0, 1.5 to 1.0, 1.6 to 1.0, 1.7 to 1.0, 1.8 to 1.0, 1.9 to 1.0, 2.0 to 1.0, 2.1 to 1.0, 2.2 to 1.0, 2.3 to 1.0, 2.4 to 1.0 or 2.5 to 1.0. A relatively high PEG/protein ratio may be advantageous in the final cycle. After the final cycle there is no recycling of unreacted (non-PEGylated) protein and therefore it may be advantageous to minimise waste of protein by minimising unreacted protein. That is, in the final cycle it may be advantageous to maximise protein PEGylation, and in particular mono-PEGylation.

The final cycle may comprise performing a PEGylation reaction at about pH 7.0 to 9.0. The PEGylation reaction may be performed at about pH 7.5 to 8.5, or at about pH 8.0. The PEGylation reaction may be performed at about 15-25° C., or about 20° C. The PEGylation reaction may have a reaction time of 30-120 minutes or about 60 minutes. The PEGylation may use an NHS-activated PEG.

The non-PEGylated protein may be recovered in the IEC step by eluting it from the IEC material. Recovering the non-PEGylated protein may therefore involve providing an eluate comprising the non-PEGylated protein in a relatively concentrated form and/or a relatively pure form. The eluate may comprise at least about 95% non-PEGylated protein.

Eluting non-PEGylated protein from the IEC material may comprise contacting the IEC material with an elution buffer. The IEC elution buffer may comprise about 40-100 mM, 50-90 mM, 60-80 mM NaCl, or about 70 mM NaCl, or at least about 40 mM, 50 mM, 60 mM or 70 mM NaCl, or about 20-60 mM, 40-50 mM, or about 45 mM NaCl. The elution buffer may comprise less than or equal to about 45 mM NaCl. The elution buffer may comprise about 20-50 mM, 25-45 mM, 30-40 mM $Na_2SO_4$, or about 35 mM $Na_2SO_4$, or at least about 20 mM, 25 mM, 30 mM or 35 mM $Na_2SO_4$. Other salts may be suitable for use in the IEC elution buffer, which may provide the same amount of negatively charged ions as the concentration ranges indicated for NaCl and $Na_2SO_4$. For example the elution buffer may contain about 70 mM NaCl or about 35 mM $Na_2SO_4$. The elution buffer may comprise about 20-30 mM, or about 25 mM bicine. The elution buffer may have a pH of about 7.0 to 9.0, 7.5 to 8.5, or about 8.0. The elution buffer may comprise about 35 mM $Na_2SO_4$, about 25 mM bicine, pH about 8.0.

The elution buffer for the IEC material may contain salt in an amount of less than or equal to about 60 mM, 55 mM, 50 mM, 45 mM, 40 mM or 35 mM. The elution buffer may contain salt in an amount of less than about 60 mM, 55 mM, 50 mM, 45 mM, or 40 mM. The salt may be $Na_2SO_4$. The salt may be a mixture of salts comprising $Na_2SO_4$. The elution buffer for the IEC material may have a conductivity of about 5-20 mS/cm, 5-15 mS/cm, or 8-10 mS/cm. The elution buffer may have a conductivity of less than or equal to about 20 mS/cm, 15 mS/cm, or 10 mS/cm.

Alternatives to bicine, for use the IEC elution buffer (or in other buffer solutions discussed herein), include for example other "Good's buffers". Buffers having a $pK_a$ from about 6 to 10 may be used. Phosphate or HEPES may be used. Buffers that do not contain a primary amine are particularly suitable (because a primary amine may act as a partner for the PEG reagent resulting in some PEGylated buffer molecules).

Alternatives to $Na_2SO_4$, for use in the IEC elution buffer (or in other buffer solutions discussed herein) may include for example salts comprising an anion selected from: $PO_4^{3-}$, $SO_4^{2-}$; $CH_3COO^-$, $Cl^-$, $Br^-$, $NO_3^-$, $ClO_4^-$, $I^-$, $SCN^-$; and a cation selected from: $NH_4^+$, $Rb^+$, $K^+$, $Na^+$, $Cs^+$, $Li_2^+$, $Mg_2^+$, $Ca_2^+$, $Ba_2^+$. Alternative salts to $Na_2SO_4$ may include NaCl, KCl, $NaHPO_4$, LiCl, and KSCN.

For example, the processes may involve performing two or more cycles of steps a), b) and c), in which non-PEGylated protein is recovered in step b) by eluting an AEC eluate from the AEC material. The eluted non-PEGylated protein is then used in a subsequent PEGylation reaction. The eluted non-PEGylated protein may be used in a subsequent step a) PEGylation reaction. The eluted non-PEGylated protein may be used in the PEGylation reaction of step a) of the next cycle. That is, further cycles of steps a), b) and c) may be performed in which non-PEGylated protein from a previous cycle is used in the PEGylation reaction of that further cycle. Alternatively, a cycle of steps a), b) and c) may be followed by a subsequent PEGylation reaction (which may be a step a) PEGylation reaction) and a processing step which provides a solution in which the fraction of PEGylated protein is increased relative to the mixture of reaction products and which allows recovery of non-PEGylated protein. That is, cycles of steps a), b) and c) may be followed by, or alternated with, a PEGylation reaction and a processing step different to but having similar effects as the step b) AEC step. Recovered non-PEGylated protein may be used in a subsequent PEGylation reaction. Recovered non-PE-Gylated protein may be used in a subsequent step a) PEGylation reaction. Recovered non-PEGylated protein may be used in a subsequent cycle of steps a), b) and c).

Various processing steps suitable for providing a solution in which the fraction of PEGylated protein is increased relative to the mixture of reaction products and which allow recovery of non-PEGylated protein exist and will be known to the skilled person. These include, for example, chromatographic methods such as cation exchange chromatography, anion exchange chromatography, and hydrophobic interaction chromatography.

A "cycle" as used herein refers to a full cycle of steps a), b), and c).

The processes may comprise three, four or five cycles, wherein step b) of each cycle comprises eluting non-PEGylated protein from the AEC material to provide an AEC eluate, and wherein the non-PEGylated protein eluted in step b) is used in a subsequent PEGylation reaction. The non-PEGylated protein eluted in step b) may be added to the PEGylation reaction of step a) in a subsequent cycle.

The processes may comprise pooling the non-PEGylated protein recovered in step b) from multiple AEC steps before it is used in a subsequent PEGylation reaction. The processes may comprise pooling the non-PEGylated protein recovered in step b) from multiple AEC steps before it is used in a subsequent step a) PEGylation reaction. The processes may comprise pooling the non-PEGylated protein recovered from two, three, four or five step b) AEC steps, or more than five step b) AEC steps.

The processes may comprise adding the step b) AEC eluate directly to a subsequent PEGylation reaction. The processes may comprise adding the AEC eluate from step b) of a cycle directly to the PEGylation reaction of step a) of the next cycle. For example the process may comprise adding the AEC eluate from step b) of a first cycle directly to the PEGylation reaction of step a) of the second cycle. Adding directly in this context means that no intervening step of purifying or cleaning the non-PEGylated protein in the eluate (e.g. by diafiltration or ultrafiltration). Rather, the eluate from the AEC material that contains the non-PEGy-lated protein is added to a subsequent PEGylation reaction.

The non-PEGylated protein used in a subsequent PEGy-lation reaction may be supplemented with fresh protein. The process may comprise adding fresh protein to the PEGy-lation reaction in addition to the non-PEGylated protein recovered from the AEC material. The step of recycling non-PEGylated protein comprises adding non-PEGylated protein recovered from the AEC material to a subsequent PEGylation reaction, and this may further comprise adding fresh protein to the PEGylation reaction such that the starting concentration of protein in the PEGylation reactions is substantially constant. Substantially constant in this context may mean that the starting concentration of protein in the second and subsequent PEGylation reactions is substantially the same as that in the first PEGylation reaction. This may mean that the starting concentration of protein in the second and subsequent PEGylation reactions is substantially the same as that in the PEGylation reaction of the first cycle.

Substantially the same may mean ±10%. Fresh protein refers to protein that has not previously been subject to a PEGylation reaction.

The processes may involve cycles of steps a), b) and c), such that a first and a second cycle are performed and the second cycle is the final cycle. Alternatively the processes of the invention may involve two further cycles of steps a), b), and c), such that a first, a second and a third cycle is performed, and the third cycle is the final cycle. The processes may involve more than two further cycles of steps a), b) and c). The processes may involve a total of one, two, three, four, or five cycles of steps a), b) and c).

The final cycle may comprise performing a PEGylation reaction wherein the PEG/protein molar ratio is from about 1.4 to 1 to about 2 to 1. The molar ratio of PEG/protein may be about 1.4 to 1.0, 1.5 to 1.0, 1.6 to 1.0, 1.7 to 1.0, 1.8 to 1.0, 1.9 to 1.0, 2.0 to 1.0, 2.1 to 1.0, 2.2 to 1.0, 2.3 to 1.0, 2.4 to 1.0 or 2.5 to 1.0. A relatively high PEG/protein ratio may be advantageous in the final cycle. After the final cycle there is no recycling of unreacted (non-PEGylated) protein and therefore it may be advantageous to minimise waste of protein by minimising unreacted protein. That is, in the final cycle it may be advantageous to maximise protein PEGylation, and in particular mono-PEGylation.

The final cycle may comprise performing a PEGylation reaction at about pH 7.0 to 9.0. The PEGylation reaction may be performed at about pH 7.5 to 8.5, or at about pH 8.0. The PEGylation reaction may be performed at about 15-25° C., or about 20° C. The PEGylation reaction may have a reaction time of 30-120 minutes or about 60 minutes. The PEGylation may use an NHS-activated PEG.

The non-PEGylated protein may be recovered in the AEC step by eluting it from the AEC material. Recovering the non-PEGylated protein may therefore involve providing an eluate comprising the non-PEGylated protein in a relatively concentrated form and/or a relatively pure form. The eluate may comprise at least about 95% non-PEGylated protein.

Eluting non-PEGylated protein from the AEC material may comprise contacting the AEC material with an elution buffer. The AEC elution buffer may comprise about 40-100 mM, 50-90 mM, 60-80 mM NaCl, or about 70 mM NaCl, or at least about 40 mM, 50 mM, 60 mM or 70 mM NaCl. The elution buffer may comprise about 20-50 mM, 25-45 mM, 30-40 mM $Na_2SO_4$, or about 35 mM $Na_2SO_4$, or at least about 20 mM, 25 mM, 30 mM or 35 mM $Na_2SO_4$. Other salts may be suitable for use in the AEC elution buffer, which may provide the same amount of negatively charged ions as the concentration ranges indicated for NaCl and $Na_2SO_4$. For example the elution buffer may contain about 70 mM NaCl or about 35 mM $Na_2SO_4$. The elution buffer may comprise about 20-30 mM, or about 25 mM bicine. The elution buffer may have a pH of about 7.0 to 9.0, 7.5 to 8.5, or about 8.0. The elution buffer may comprise about 35 mM $Na_2SO_4$, about 25 mM bicine, pH about 8.0.

The elution buffer for the AEC material may contain salt in an amount of less than or equal to about 60 mM, 55 mM, 50 mM, 45 mM, 40 mM or 35 mM. The elution buffer may contain salt in an amount of less than about 60 mM, 55 mM, 50 mM, 45 mM, or 40 mM. The salt may be $Na_2SO_4$. The salt may be a mixture of salts comprising $Na_2SO_4$. The elution buffer for the AEC material may have a conductivity of about 5-20 mS/cm, 5-15 mS/cm, or 8-10 mS/cm. The elution buffer may have a conductivity of less than or equal to about 20 mS/cm, 15 mS/cm, or 10 mS/cm.

Alternatives to bicine, for use the AEC elution buffer (or in other buffer solutions discussed herein), include for example other "Good's buffers". Buffers having a $pK_a$ from about 6 to 10 may be used. Phosphate or HEPES may be used. Buffers that do not contain a primary amine are particularly suitable (because a primary amine may act as a partner for the PEG reagent resulting in some PEGylated buffer molecules).

Alternatives to $Na_2SO_4$, for use in the AEC elution buffer (or in other buffer solutions discussed herein) may include for example salts comprising an anion selected from: $PO_4^{3-}$, $SO_4^{2-}$; $CH_3COO^-$, $Cl^-$, $Br^-$, $NO_3^-$, $ClO_4^-$, $I^-$, $SCN^-$; and a cation selected from: $NH_4^+$, $Rb^+$, $K^+$, $Na^+$, $Cs^+$, $Li_2^+$, $Mg_2^+$, $Ca_2^+$, $Ba_2^+$. Alternative salts to $Na_2SO_4$ may include NaCl, KCl, $NaHPO_4$, LiCl, and KSCN.

Performance of AEC and HIC Steps

The IEC and HIC steps in the processes of the invention may be performed sequentially. For example the AEC and HIC steps in the processes of the invention may performed sequentially. That is the process may comprise sequential steps of a) providing a first mixture comprising non-PEGylated protein and PEGylated protein, wherein the PEGylated protein comprises mono-PEGylated protein and oligo-PEGylated protein b) subjecting the first mixture to an anion exchange chromatography (AEC) step to provide an AEC flow-through solution in which the fraction of PEGylated protein is increased relative to the first mixture; the AEC step comprising applying the first mixture to an AEC material under conditions suitable for binding non-PEGylated protein; c) collecting the AEC flow-through solution from step b) to provide a second mixture comprising mono-PEGylated protein and oligo-PEGylated protein; and d) subjecting the second mixture to a hydrophobic interaction chromatography (HIC) step to provide a mono-PEGylated protein composition in which the fraction of mono-PEGylated protein is increased relative to the second mixture, wherein the mono-PEGylated protein composition comprises at least about 90% mono-PEGylated protein.

The term "sequential" means that no intervening chromatography step occurs between any of steps a to d (no chromatography step between steps (a) and (b), (b) and (c), (c) and (d)). The term "sequential" means that no intervening chromatography step occurs between any of the steps recited in any one of the claims. The steps of the processes of the invention may be performed directly, meaning that each of steps (b) to (d) is performed directly following the previous step. The process may consist of steps (a) to (d). The process may consist of the steps recited in any one of the claims.

Steps (b) to (d) may be performed discontinuously or continuously. Steps (b) to (d) may be performed sequentially and discontinuously or sequentially and continuously. Continuously means that the AEC material and the HIC material are connected directly or there is some other mechanism which allows for continuous flow between the AEC material and the HIC material. Discontinuously means that there is no continuous flow between the AEC material and the HIC material, for example the AEC flow-through solution or effluent is collected and pooled to provide the second mixture. Performance of the steps continuously may mean that the same flow rate is used for the entire process.

The IEC flow-through solution may be applied directly to the HIC material. Preferably a conditioning step is performed to directly provide the HIC material with a conditioned second mixture. The IEC material and HIC material may be directly connected in series. For example the IEC material may be comprised in a IEC column and the HIC material may comprised in a HIC column, and the IEC column is directly connected to the HIC column. The IEC flow-through solution from the IEC column may be directly delivered to the HIC column. There may be an in-line connection between the IEC column and the HIC column. There may be a mechanism that permits continuous flow between the IEC column and the HIC column. The steps of the process may be performed continuously. The steps of the process may be performed in parallel, that is, step (d) may be begun before step (b) is completed, such that steps (b) and (d) run in parallel. That is HIC step and IEC step may be run in parallel. Performing the process continuously (or in parallel) is advantageous because it is relatively fast and efficient.

When the IEC step is a CEC step, the CEC and HIC steps can be performed sequentially, and/or can be performed continuously or discontinuously, as described for the AEC and HIC steps above.

Purification Processes Separating Mono-PEGylated Protein and Oligo-PEGylated Protein The processes of the invention use an IEC material with a relatively low binding capacity for the PEGylated form of the protein and a relatively high binding capacity for the non-PEGylated form of the protein. This is advantageous because it facilitates rapid separation of non-PEGylated protein from PEGylated protein. Much of the binding capacity of the column is used for binding to the non-PEGylated form of the protein which facilitates the processing of relatively large volumes of first mixture (the mixture comprising non-PEGylated mono-PEGylated and oligo-PEGylated protein) using a relatively small column. This is because the first mixture is generally relatively low in non-PEGylated protein (which the IEC binding material has a relatively high binding capacity for) and high in PEGylated protein (which the IEC binding material has a relatively low binding capacity for) —this means that in operation the processes disclosed herein can process relatively large volumes of first mixture in the IEC step. The relatively rapid separation of non-PEGylated protein from PEGylated protein facilitates rapid recycling of non-PEGylated protein and overall process efficiency.

As described above, the present invention provides processes for producing a mono-PEGylated protein composition comprising at least about 90% mono-PEGylated protein, the process comprising: subjecting the PEGylated protein mixture comprising mono-PEGylated protein and oligo-PEGylated protein produced as an IEC flow-through solution described above to a purification process separating mono-PEGylated protein and oligo-PEGylated protein. The IEC flow-through solution may be an AEC flow-through solution.

Various suitable purification processes exist and will be known to the skilled person, for example, precipitation, size dependent separation, and filtration methods, as well as chromatographic methods such as size exclusion chromatography, cation exchange chromatography, anion exchange chromatography, and hydrophobic interaction chromatography. In the processes described herein hydrophobic interaction chromatography may be a preferred purification process.

Hydrophobic Interaction Chromatography

HIC materials may comprise a resin that has been functionalised with a hydrophobic ligand. Hydrophobic ligands on HIC materials may interact with hydrophobic surfaces of proteins. The ligand and the degree of substitution (high or low substitution "sub") on a HIC material may contribute to its final hydrophobicity and thereby to its selectivity. The ligand may contain alkyl or aryl groups. The hydrophobicity of HIC materials increases through the ligand series: ether, polypropyleneglycol (PPG), phenyl, butyl and hexyl.

The HIC material used in the processes of the invention may comprise a phenyl ligand. It may comprise a methacrylic resin functionalised with a phenyl ligand. It may be a hydroxylated polymethacrylic polymer bead functionalised with a phenyl ligand. It may have a 50-150 nm, 70-120 nm, 70-100 nm, 90-110 nm pore size. It may have a particle size of 40-150 µm, 40-120 µm, 40-100 µm, 40-80 µm, or about 60, 65, 70, 80, or 90 100 µm. It may have a 70-100 nm pore size and a 30-65 µm bead size. It may have a 100 nm pore size and a 65 µm bead size. It may be Toyopearl Phenyl 650M (Tosoh Bioscience LLC; product number 14478). The HIC material used in the processes of the invention may be used in accordance with the manufacturer's instructions.

The HIC material may be or may comprise a column, for example an expanded bed or packed bed column. The HIC material may be in the form of a porous monolithic material. The HIC material may be in the form of a functionalised fibre, fleece, or mesh. The HIC material may be in the form of any other solid support able to carry functional groups or exhibiting HIC properties. HIC materials include Toyopearl Phenyl 650M, Toyopearl Phenyl 650S, Toyopearl PPG 600M, TSKgel Phenyl 5 PW, Butyl Sepharose 4 FF, Butyl-S Sepharose FF, Octyl Sepharose 4 FF, Phenyl Sepharose BB, Phenyl Sepharose HP, Phenyl Sepharose 6 FF High Sub, Phenyl Sepharose 6 FF Low Sub, Source I SETH, Source 151 SO, Source 1 SPHE, Phenyl Sepharose BB, Phenyl Sepharose HP, Phenyl Sepharose 6 FF High Sub, Phenyl Sepharose 6 FF Low Sub, Source I SETH, Source 151 SO, Source 1 SPHE, Cellufine Butyl, Cellufine Octyl, Cellufine Phenyl, WP HI-Propyl (C3), Macroprep t-Butyl, Macroprep methyl.

The processes of the invention may comprise a HIC step in flow through mode. In flow through mode the PEGylated protein mixture (or "second mixture") is applied to a HIC material under conditions suitable for mono-PEGylated protein to flow through the HIC material and is therefore present in the HIC flow-through solution. The conditions are suitable for oligo-PEGylated protein to bind to the HIC material.

The process of the invention may comprise a HIC step in bind and elute mode. In bind and elute mode the PEGylated protein mixture (or "second mixture") is applied to a HIC material under conditions suitable for mono-PEGylated protein and oligo-PEGylated protein to bind to the HIC material. The mono-PEGylated protein is eluted from the HIC material. A gradient of decreasing salt is used to elute the mono-PEGylated protein. The oligo-PEGylated protein is eluted at a lower salt concentration and therefore in a separate fraction from the mono-PEGylated protein.

A HIC material may be equilibrated before the PEGylated protein mixture (or "second mixture" or HIC load solution), is loaded on to it. An HIC equilibration buffer may comprise a salt such as $Na_2SO_4$ and/or bicine. An HIC equilibration buffer may have a pH of about 6.5 to 9.0, 7.5 to 8.5, or 8.0. An HIC equilibration buffer may comprise about 10-40 mM, 15-35 mM, 20-30 mM bicine or about 25 mM bicine. An HIC equilibration buffer may comprise about 10-40 mM, 15-35 mM, 20-30 mM bicine or about 25 mM $NaPO_4$.

Conditions suitable for mono-PEGylated protein to flow through the HIC material while oligo-PEGylated protein is bound to the HIC material can be readily determined. The pH, ionic strength, and composition of the equilibration buffer may be selected to ensure that when a protein mixture is loaded onto the chromatography matrix, the desired binding and/or flow through or specific proteins or contaminants is achieved. For example, the pH, ionic strength, and composition of the equilibration buffer may be selected to ensure that mono-PEGylated protein flows through the HIC material while oligo-PEGylated protein is bound to the HIC material.

For equilibration before a HIC step in flow through mode is carried out, an equilibration buffer may comprise about 200-500 mM, 250-450 mM, 300-450 mM, 300-400 mM, 350-400 mM salt, or about 390 mM salt or about 300 mM salt. An equilibration buffer for use in flow through mode HIC may comprise about 25 mM bicine, about 390 mM $Na_2SO_4$, PH 8.0. An equilibration buffer for use in flow through mode HIC may comprise about 25 mM bicine, about 300 mM $Na_2SO_4$, PH 8.0. An equilibration buffer for use in flow through mode HIC may comprise about 25 mM $NaPO_4$, about 300 mM $Na_2SO_4$, pH 8.0. An equilibration buffer for use in flow through mode HIC may have a conductivity of about 30-70 mS/cm, 40-60 mS/cm, or about 50 mS/cm.

When the process comprises a HIC step in flow through mode, the process may involve providing a conditioned PEGylated protein mixture (or "second mixture") comprising salt (such as $Na_2SO_4$) and bicine, which may be present as about 300 mM $Na_2SO_4$ and about 25 mM bicine, or which may be present as about 390 mM $Na_2SO_4$ and about 25 mM bicine. A conditioned PEGylated protein mixture may be referred to as a HIC load solution. A conditioned PEGylated protein mixture for use in HIC flow through mode may comprise about 200-500 mM, 250-450 mM, 250-350 mM salt, or about 300 mM salt, or about 350-450 mM salt, or about 390 mM salt. The salt may be $Na_2SO_4$. A conditioned PEGylated protein mixture may comprise about 10-40 mM, 15-35 mM, 20-30 mM bicine or about 25 mM bicine. A conditioned PEGylated protein mixture may comprise about 300 mM $Na_2SO_4$ and about 25 mM bicine.

In HIC flow through mode, after the PEGylated protein mixture has been applied to the HIC material the HIC material may be washed. The HIC material may be washed with equilibration buffer that is suitable for use in flow through mode. The HIC material may be washed with a HIC wash buffer, which may comprise about 200-500 mM, 250-450 mM, 300-450 mM, 300-400 mM, 350-400 mM salt, or about 390 mM salt, or about 300 mM salt. A wash buffer for use in flow through mode HIC may comprise about 25 mM bicine, about 390 mM $Na_2SO_4$, pH 8.0. A wash buffer for use in flow through mode HIC may comprise about 25 mM bicine, about 300 mM $Na_2SO_4$, PH 8.0. The HIC material may be washed with 1 to 10, 1 to 5, or about 1, 2, 3, 4, or 5 column volumes of buffer. The HIC material may be washed with a volume of equilibration buffer or wash buffer that is determined by monitoring protein content of the flow-through solution (e.g. by UV spectrometry) and stopping the wash process once the protein content is below a threshold value (e.g. when UV signal returns to baseline). The flow-through solution, or effluent, may be collected as fractions, and some or all of these flow-through fractions may be pooled.

The PEGylated protein mixture (or "second mixture") may comprise zero, or close to zero, non-PEGylated protein. The PEGylated protein mixture may comprise less than about 10%, 5%, 4%, 3%, 2%, 1.5%, 1.0%, 0.5% or 0.1% non-PEGylated protein. The PEGylated protein mixture may comprise less than about 2% non-PEGylated protein. The PEGylated protein mixture may comprise less than about 2% non-PEGylated EPO.

When the process of the invention comprises a HIC step in flow through mode the non-PEGylated protein content of the PEGylated protein mixture should be below the threshold specification for the final therapeutic product.

When the HIC step is performed in flow-through mode, the HIC flow-through provides the mono-PEGylated protein composition. That is the HIC flow-through is a mono-PEGylated protein composition as described herein. The HIC flow-through may comprise at least 90% mono-PEGylated protein.

When the HIC step is performed in flow through mode, oligo-PEGylated protein may be eluted from the HIC material. For example by a gradient or step elution at a conductivity of 0 mS/cm.

For equilibration before an HIC step in bind and elute mode is carried out, an equilibration buffer may comprise about 400-600 mM, 450-550 mM, salt, or about 500 mM salt. An equilibration buffer for use in bind and elute mode HIC may comprise about 25 mM bicine, about 500 mM $Na_2SO_4$, PH 8.0. An equilibration buffer for use in bind and elute mode HIC may have a conductivity of about 40-80 mS/cm, 50-70 mS/cm, or about 60 mS/cm or about 58 mS/cm.

When the process comprises a HIC step in bind and elute mode, the process may involve providing a conditioned PEGylated protein mixture (or "second medium") comprising salt (such as $Na_2SO_4$) and bicine, which may be in any combination of the previously-mentioned concentrations, and which may be present as about 500 mM $Na_2SO_4$ and about 25 mM bicine, and the elution step may comprise elution with a decreasing gradient of 500 mM to 0 mM $Na_2SO_4$. A conditioned PEGylated protein mixture may be referred to as a HIC load solution. A conditioned PEGylated protein mixture for use in HIC bind and elute mode may comprise about 250-750 mM, 400-600 mM, 450-550 mM salt, or about 500 mM salt. The salt may be $Na_2SO_4$. Other salts may be used, such as NaCl. Other salts may be used at concentrations that provide ionic strength equivalent to the $Na_2SO_4$ concentrations. A conditioned PEGylated protein mixture may comprise about 10-40 mM, 15-35 mM, 20-30 mM bicine or about 25 mM bicine. A conditioned PEGylated protein mixture may comprise about 500 mM $Na_2SO_4$ and about 25 mM bicine.

When the HIC step is performed in bind and elute mode, the mono-PEGylated protein is eluted from the HIC material. Elution is by decreasing salt gradient. Elution may comprise applying a linear elution gradient from 500 mM to 0 mM salt, such as $Na_2SO_4$. Elution may comprise applying a linear elution gradient from about 60 mS/cm to 0 mS/cm. In a decreasing salt gradient mono-PEGylated EPO elutes at approximately 300 mM $Na_2SO_4$ (see FIG. 6). Eluting the mono-PEGylated protein from the HIC material to provides a HIC eluate, wherein the HIC eluate provides the mono-PEGylated protein.

When the HIC step is performed in flow-through mode, the HIC flow-through provides the mono-PEGylated protein composition. That is the HIC flow-through is a mono-PEGylated protein composition as described herein. The HIC flow-through may comprise at least 90% mono-PEGylated protein.

The PEGylated protein mixture (or "second mixture") may be conditioned for the HIC step in one or more batches. The PEGylated protein mixture may be conditioned in-line. The step of providing a second mixture (step c) may comprise conditioning the mixture in-line, to provide a conditioned medium directly from the IEC apparatus (e.g. a AEC or CEC column) to the HIC apparatus (e.g. HIC column). For example, the step of providing a PEGylated protein mixture (step c) may comprise conditioning the mixture in-line, to provide a conditioned medium directly from the AEC apparatus (e.g. AEC column) to the HIC apparatus (e.g. HIC column).

Room temperature may be about 18-25° C., 20-22° C., about 20° C., about 21° C. or about 22° C. The processes disclosed herein may be performed at room temperature. HIC may be performed at room temperature. HIC may be performed at a temperature of 15-25° C. For reproducibility processes may perform HIC at a specific and stable temperature. A stable temperature may be a specific temperature±1.0° C. or ±1.0° C.

The process of the invention may comprise subjecting the second mixture to a HIC step in flow through mode to provide a HIC flow-through solution in which the fraction of mono-PEGylated protein is increased relative to the second mixture, the HIC step comprising applying the second mixture to a HIC material under conditions suitable for binding oligo-PEGylated protein, wherein the HIC flow-through provides the mono-PEGylated protein composition. In such processes, the HIC material may be Toyopearl Phenyl 650M, the HIC step is performed at a pH of about 7.0 to 9.0 and a conductivity of about 30-40 mS/cm; and the second mixture is applied to the HIC material as a HIC load solution comprising about 25 mM bicine and about 390 mM $Na_2SO_4$. The protein may be erythropoietin.

Processes Disclosed Herein are Advantageous form of the protein and a relatively high binding capacity for the non-PEGylated form of the protein. This is advantageous because it facilitates rapid separation of non-PEGylated protein from PEGylated protein. Much of the binding capacity of the column is used for binding to the non-PEGylated form of the protein which facilitates the processing of relatively large volumes of first mixture (the mixture comprising non-PEGylated mono-PEGylated and oligo-PEGylated protein) using a relatively small column. This is because the first mixture is generally relatively low in non-PEGylated protein (which the IEC binding material has a relatively high binding capacity for) and high in PEGylated protein (which the IEC binding material has a relatively low binding capacity for) —this means that in operation the processes disclosed herein can process relatively large volumes of first mixture in the IEC step. The relatively rapid separation of non-PEGylated protein from PEGylated protein facilitates rapid recycling of non-PEGylated protein and overall process efficiency.

The processes of the invention comprise recycling non-PEGylated protein without performing a diafiltration or ultrafiltration step. This provides a faster process enabling higher productivity compared with processes that involve recycling of non-PEGylated protein but which require removal or reduction of salt from non-PEGylated protein fraction.

The processes of the invention also have a relatively high yield compared with prior art process such as that disclosed in WO 2009/010270. Recycling of non-PEGylated (unreacted) protein increases overall yield. As discussed in the Examples below, the processes disclosed herein provide a yield of mono-PEGylated protein that is more than 40% higher than that of the process disclosed in WO 2009/010270. The productivity of the processes disclosed herein is expected to be at least double that of prior art processes of the type disclosed in WO 2009/010270, and may be many fold higher. The productivity of the processes disclosed herein is expected to be at least double that of prior art processes of the type disclosed in WO 2009/010270, when using equipment of equal size, and may be many fold higher.

Compared with the process disclosed in Pfister (Biotech and BioEng 2016; 113) the processes disclosed herein are calculated to be around twice as productive (around 1.7 fold more productive). The increased productivity is mostly the result of avoiding the need for time-consuming diafiltration of non-PEGylated (unreacted) EPO before it can be recycled by addition to a subsequent PEGylation reaction. Because the unreacted EPO is recovered faster in the presently-disclosed processes the overall productivity is greater. The processes disclosed herein also involve a faster PEGylation reaction. The PEGylation processes disclosed herein are calculated to produce 20-33% more mono-PEGylated EPO per reaction than the process disclosed in Pfister.

Compared with the process disclosed in WO 2009/010270, the processes disclosed herein are more productive and have higher yields of mono-PEGylated protein.

Binding Capacity

The binding capacity of a chromatography material refers to the amount of protein which can bind to the medium under defined experimental conditions. Binding capacity herein may refer to dynamic binding capacity. The dynamic binding capacity refers to the amount of protein which can bind to the medium under defined experimental conditions that include the flow rate of the mobile phase (or buffer solution). The binding capacity may refer to the static binding capacity, which refers defined experimental conditions that do not include the flow rate.

Dynamic binding capacity for a specific protein may be determined using conventional techniques. Dynamic binding capacity for a specific protein may be determined by loading a sample containing a known concentration of that specific protein and measuring protein concentration in the flow-through to solution to establish the amount of protein can protein be bound before a significant amount of protein starts to "break through". This may be achieved by generating a "break through curve" for the chromatography material under defined experimental conditions. The experimental conditions under which the dynamic binding capacity is measured may be the operating conditions. The experimental conditions may be the conditions used in the process used to provide the mono-PEGylated protein composition. In processes employing chromatography materials, loading conditions may thus be adjusted such that a protein of interest is applied in a range less than the "break through" capacity of the chromatography material, to avoid overloading of the chromatography material.

Reference to dynamic binding capacity herein refers to the dynamic binding capacity under the conditions chosen for the chromatography process or step. The dynamic binding capacity of a chromatography medium under particular chromatography conditions for a particular protein can be thought of as the maximum amount of that protein that can be loaded onto the chromatography medium without causing unnecessary protein loss. That is, the maximum amount of protein of interest that can be loaded without causing "breakthrough". Protein breakthrough may be monitored by spectrophotometry for example at 280 nm (A280). The breakthrough threshold may be 10%. The chromatography conditions may be the pH, conductivity and flow rate, and the concentrations of any salts or other additives to the mobile phase. The dynamic binding capacity chromatography material are determined under the operating conditions (the conditions chosen for) for the relevant chromatography step. For example the dynamic binding capacity of the AEC material is determined under the operating conditions for the AEC step of the processes of the invention In the present context the binding capacity may refer to the dynamic binding capacity under the chromatography conditions used to prepare the mono-PEGylated protein composition. For example, the binding capacity of AEC material may refer to the dynamic binding capacity of an AEC material in 25 mM bicine, about 7.5 mM $Na_2SO_4$, pH 8, at a flow rate of 200 cm/h, residence time 3.3 minutes.

The binding capacity of HIC material may be about 5 g/L PEGylated protein in flow through mode and 2 g/L PEGylated protein in bind and elute mode. The dynamic binding capacity of the HIC material used in flow-through mode for oligo-PEGylated protein may be at least about 2 g/L, 3 g/L, 4 g/L, or 5 g/L, or about 2-8 g/L, 3-7 g/L, 4-6 g/L, or about 5 g/L. The dynamic binding capacity of the HIC material used in bind and elute mode for PEGylated protein may be at least about 0.5 g/L, 1 g/L, 2 g/L, 3 g/L, 4 g/L, or 5 g/L, or about 0.5-4 g/L, 1-3 g/L, or about 5 g/L. The binding capacity may refer to the dynamic binding capacity for PEGylated protein of an HIC material in 25 mM bicine, about 300 mM $Na_2SO_4$, PH 8.0, at a flow rate of 150 cm/h, residence time 3.3 minutes, or in 25 mM bicine, about 390 mM $Na_2SO_4$, PH 8.0, at a flow rate of 150 cm/h, residence time 3.3 minutes.

In embodiments where the ion exchange chromatography step is anion exchange chromatography, the AEC step is performed under conditions suitable for non-PEGylated protein to bind to the AEC material. The suitability of the conditions can be considered in terms of dynamic binding capacities. The AEC step is performed in flow through mode. In flow through mode for AEC in the processes of the invention PEGylated protein is bound relatively weakly by the AEC material and non-PEGylated protein is bound relatively strongly (tightly). In such conditions the dynamic binding capacity of the AEC material for non-PEGylated protein is relatively high and the dynamic binding capacity of the AEC material for PEGylated protein is relatively low. The chromatography conditions can be selected to maximise dynamic binding capacity for non-PEGylated protein. The chromatography conditions can be selected to minimise dynamic binding capacity for PEGylated protein. The chromatography conditions can be selected to adjust, or optimise, the dynamic binding capacity of the AEC material for PEGylated protein and non-PEGylated protein in order that non-PEGylated protein is retained on the AEC material and PEGylated protein is recovered in the flow-through solution. The AEC material may have a dynamic binding capacity for the PEGylated protein of less than about 2.5 g/L, 1.5 g/L or 1.0 g/L, or about 1.0-2.5 g/L. For example, the AEC material may have a dynamic binding capacity for the PEGylated protein of less than about 1.5 g/L.

Thus in the processes of the invention subjecting the first mixture to an AEC step may comprise loading the first mixture onto the AEC material at a load that is about equal to, or at a load that is lower than, the dynamic binding capacity of the AEC material for non-PEGylated protein. It may comprise loading the first mixture onto the AEC material at a load at least 2, 5, 10, 20, 25 or 30 times lower than the dynamic binding capacity of the AEC material for non-PEGylated protein (such that non-PEGylated material is retained on the AEC material). The amount of non-PEGylated protein applied to the anion exchange material may be in the range of about 80-95% of the dynamic binding capacity of the anion exchange material. The first mixture may be loaded onto the AEC material at a load that is higher than, or at least 2, 5, 20, 25 or 30 times higher than the dynamic binding capacity of the AEC material for PEGylated protein (such that PEGylated protein is recovered in the flow-through solution or effluent from the AEC material).

Subsequent elution of non-PEGylated protein from the AEC material is carried out under conditions in which the dynamic binding capacity of the AEC material for the non-PEGylated protein is relatively low. This may be achieved by applying an elution buffer of relatively high conductivity compared with the load and/or wash buffers.

The HIC step may be performed in flow through mode. In flow through mode of an HIC step in a process of the invention the protein of interest (in this case mono-PEGylated protein) is bound relatively weakly by the HIC material and the unwanted protein (or contaminant, in this case oligo-PEGylated protein) is bound relatively strongly (tightly). In such conditions the dynamic binding capacity of the HIC material for oligo-PEGylated protein is higher than the dynamic binding capacity of the HIC material for mono-PEGylated protein. The chromatography conditions can be selected to maximise strength of binding for oligo-PEGylated protein and/or minimise strength of binding for mono-PEGylated protein.

The HIC step may be performed in bind and elute mode. In bind and elute mode in an HIC step in a process of the invention the protein of interest (in this case mono-PEGylated protein) is bound relatively weakly by the HIC material and the unwanted protein (or contaminant, in this case oligo-PEGylated protein) is bound relatively strongly (tightly) by the HIC material. The mono-PEGylated protein can be eluted from the HIC material before the oligo-PEGylated protein, using a decreasing salt gradient.

In embodiments where the ion exchange chromatography step is cation exchange chromatography, the CEC step is performed under conditions suitable for non-PEGylated protein to bind to the CEC material. The suitability of the conditions can be considered in terms of dynamic binding capacities. The CEC step is performed in flow through mode. In flow through mode for CEC in the processes of the invention PEGylated protein is bound relatively weakly by the CEC material and non-PEGylated protein is bound relatively strongly (tightly). In such conditions the dynamic binding capacity of the CEC material for non-PEGylated protein is relatively high and the dynamic binding capacity of the CEC material for PEGylated protein is relatively low. The chromatography conditions can be selected to maximise dynamic binding capacity for non-PEGylated protein and/or minimise dynamic binding capacity for PEGylated (or mono-PEGylated) protein. The chromatography conditions can be selected to adjust, or optimise, the dynamic binding capacity of the CEC material for PEGylated protein and non-PEGylated protein in order that non-PEGylated protein is retained on the CEC material and PEGylated protein is recovered in the flow-through solution. The CEC material may have a dynamic binding capacity for the PEGylated protein of less than about 2.5 g/L, 1.5 g/L or 1.0 g/L, or about 1.0-2.5 g/L. For example, the CEC material may have a dynamic binding capacity for the PEGylated protein of less than about 1.5 g/L.

Thus in the processes of the invention subjecting the first mixture to an CEC step may comprise loading the first mixture onto the CEC material at a load that is about equal to, or at a load that is lower than, the dynamic binding capacity of the CEC material for non-PEGylated protein. It may comprise loading the first mixture onto the CEC material at a load at least 2, 5, 10, 20, 25 or 30 times lower than the dynamic binding capacity of the CEC material for non-PEGylated protein (such that non-PEGylated material is retained on the CEC material). The amount of non-PEGylated protein applied to the anion exchange material may be in the range of about 80-95% of the dynamic binding capacity of the anion exchange material. The first mixture may be loaded onto the CEC material at a load that is higher than, or at least 2, 5, 20, 25 or 30 times higher than the dynamic binding capacity of the CEC material for PEGylated protein (such that PEGylated protein is recovered in the flow-through solution or effluent from the CEC material).

Subsequent elution of non-PEGylated protein from the CEC material is carried out under conditions in which the dynamic binding capacity of the CEC material for the non-PEGylated protein is relatively low. This may be achieved by applying an elution buffer of relatively high conductivity compared with the load and/or wash buffers.

Chromatography Conditions

The amount of protein loaded on to a chromatography material may depend on the binding capacity of the material. For example if an AEC material has a binding capacity for non-PEGylated EPO of about 35 g/L, and about 50% of the EPO in the mixture of reaction products is non-PEGylated then the maximum load of the mixture of reaction products (in terms of total protein) applied to the AEC material would be about 70 g/L.

Flow rates for chromatography steps may be selected and adjusted according to conventional techniques. Faster flow rates will decrease binding capacity, which means that a balance may be reached between achieving maximum dynamic binding capacity and a fast separation, particularly when applying large volumes of protein mixtures to be separated. Suitable flow rates may be 50-400 cm/h. Residence times may be 3-5 minutes, or possibly less, depending on the chromatography material used. Faster flow rates and shorter residence times may be desirable for improving overall process productivity.

Chromatography steps may be performed under conditions "suitable for binding" a particular protein (or PEGylation form of a protein). The skilled person is familiar with chromatography techniques and is able to find conditions suitable for binding a particular protein empirically, using his common general knowledge and guided by the present disclosure. Parameters such as chromatography material, type and/or concentration of salt, pH, buffers, temperature and flow rate can all be altered to provide conditions suitable for binding a particular protein (or PEGylation form of a protein) in chromatography.

As noted above, in AEC protein mixtures (load compositions) and wash buffers of a relatively high pH are generally used, in order that the protein of interest (or contaminant, e.g. unwanted protein) has a net negative charge and therefore binds to the positively charged anion exchange material. Conversely in CEC protein mixtures and wash buffers of a relatively low pH are generally used, in order that the protein of interest (or contaminant, e.g. unwanted protein) has a net positive charge and therefore binds to the negatively charged cation exchange material.

The processes of the present invention may be used for producing a mono-PEGylated protein composition wherein the protein has a pI of about 8.0 or lower, or 7.0 or lower, or 6.0 or lower. The processes of the invention are particularly suitable for proteins having a pI of 6.0 or lower. In this case, the ion exchange chromatography step may be an AEC step and the AEC conditions are at a pH greater than the pI of the protein, preferably at least 0.5, 1.0, 1.5, 2.0, 2.5, 3.0, 3.5, or 4.0 pH units greater than the pI of the protein. In this context the pI may refer to the pI of the most basic isoform of the protein, or the pI of the most abundant isoform of the protein, in the protein composition.

The processes of the present invention may be used for producing a mono-PEGylated protein composition wherein the protein has a pI of about 8.0 or higher. In this case, the ion exchange chromatography step may be a CEC step and the CEC conditions are at a pH lower than the pI of the protein, preferably at least 0.5, 1.0, 2.0 or 3.0 pH units lower than the pI of the protein. In this context the pI may refer to the pI of the most acidic isoform of the protein, or the pI of the most abundant isoform of the protein, in the protein composition. The protein may have a pI of about 2.0-6.0, 2.5-5.5, 3.0-5.5, 3.5-5.0, or about 3.5-4.5.

The processes of the present invention may be used for producing a mono-PEGylated protein composition wherein the protein has a pI of about 6.0-8.0. In this case, the ion exchange chromatography step may be an AEC or a CEC step the pH conditions selected to be pH lower than the pI of the protein for AEC, and higher than the pI of the protein for CEC. Preferably the pH of the ion exchange step is at least 0.5, 1.0, 2.0 or 3.0 pH units away from (different than) the pI of the protein. In this context the pI may refer to the pI of the most acidic or basic isoform of the protein, or the pI of the most abundant isoform of the protein, in the protein composition. Ion exchange chromatography is an established technique and therefore the skilled person would have no difficulty in selecting pH conditions suitable for practicing the processes of the present invention (i.e. selecting pH conditions that favour binding of the non-PEGylated protein to the ion exchange material and allow PEGylated protein to pass through/over the material to be recovered in the flow-through solution).

The pH of the PEGylation reaction may be the substantially same as the pH of the ion exchange step (the AEC step or CEC step). The pH of the PEGylation reaction may be selected to be substantially the same as the pH of the ion exchange step, such that the protein mixture resulting from the PEGylation reaction is loaded directly onto the ion exchange material. In this context substantially the same means within 1.0, 0.9, 0.8, 0.6, 0.7, 0.5, 0.4, 0.3, 0.2, or 0.1 pH units. In such processes the first mixture is the mixture of reaction products that results from the PEGylation reaction. Such processes are relatively efficient and fast. In this context "loaded directly" means that no pH adjustment of the mixture of reaction products is carried out before it is subjected to the ion exchange chromatography step. The buffer for the PEGylation reaction may be the same as the buffer for the ion exchange step.

A PEGylation reaction may be performed at a pH of about 6.5 to 9.5. The pH of the PEGylation reaction may be selected to be at least 0.5, 1.0, 2.0 or 3.0 pH units away from the pI of the protein, such that the mixture of reaction products can be loaded directly on to the ion exchange material at a pH that favours binding of the protein. In this context, a protein having a relatively neutral pH (e.g. pI about 7.5) could be PEGylated in a reaction at about pH 9.5 and the mixture of reaction products subjected to an AEC step. Alternatively, a protein having a pI of about 7.5 could be PEGylated in a reaction at about pH 6.5 and the mixture of reaction products subjected to a CEC step. The pH of the PEGylation reaction can be selected such that it is at least 0.5, 1.0, 2.0 or 3.0 pH units away from the pI of the protein, and the mode of ion exchange chromatography (AEC or CEC) selected accordingly. In this way the mixture of reaction products can be subjected to the ion exchange chromatography step.

In the present context, chromatography steps (such as AEC, CEC or HIC) may remove a "contaminant" from a mixture (such as a mixture of reaction products, also referred to herein as a "first mixture"; or PEGylated protein mixture, also referred to herein as a "second mixture"), wherein the contaminant is an undesired form of protein. A contaminant may also be referred to as an impurity. For example, since the desired form of protein in the present context is mono-PEGylated protein, the chromatography step may remove non-PEGylated protein or oligo-PEGylated protein. The chromatography step may also remove other contaminants, such as protein aggregates, or PEGylation reactants.

The present disclosure provides the use of an AEC medium, or a CEC medium, for removing non-PEGylated protein from a mixture comprising non-PEGylated protein and PEGylated protein. The protein may be EPO. The use of the AEC medium may be carried out in the processes for preparing a mono-PEGylated protein, as disclosed herein.

Chromatography conditions and chromatography materials for carrying out the present invention may be selected using a screening process. The screening process may allow screening for selectivity of binding. Selectivity of binding is advantageous. For example ion exchange materials and conditions can be screened for selectivity which favours binding of non-PEGylated protein to the AEC material and non-binding of PEGylated protein to the ion exchange material. For example HIC materials and flow-through conditions can be screed for selectivity which favours binding of oligo-PEGylated protein and non-binding of mono-PEGylated protein. A screening process for an ion exchange material, such as an AEC material or a CEC material, may involve applying a mixture of non-PEGylated, mono-PEGylated and oligo-PEGylated proteins to the ion exchange material at relatively low conductivity, then applying an increasing conductivity (e.g. salt) gradient to the material and monitoring the appearance of the non-PEGylated, mono-PEGylated and oligo-PEGylated in the eluate. This process could be conducted at several different pH values. A screening process for a HIC material may involve applying a mixture of non-PEGylated, mono-PEGylated and oligo-PEGylated proteins to the HIC material under relatively high salt conditions, then applying a decreasing salt gradient to the material and monitoring the appearance of the non-PEGylated, mono-PEGylated and oligo-PEGylated in the eluate. Chromatography materials and conditions may be assessed for selectivity of binding by analysing the eluate by UV chromatography and screening for materials and conditions that provide good separation of peaks in the chromatograms.

PEG

Poly(ethylene glycol) or PEG is a neutral hydrophilic polyether. The term "molecular weight" (in kDa) in the present context is to be understood as the mean molecular weight of the PEG because PEG as polymeric compound is not obtained with a defined molecular weight but in fact has a molecular weight distribution; the term "about" indicates that some PEG molecules, or residues, will weigh more and some less than the indicated molecular weight, i.e. the term "about" in this context may refer to a molecular weight distribution in which 95% of the PEG molecules have a molecular weight within +/−10% of the indicated molecular weight. For example, a molecular weight of 30 kDa may denote a range of from 27 kDa to 33 kDa.

A PEG residue can contain further chemical groups which are necessary for binding reactions, which results from the chemical synthesis of the PEGylated molecule, or which is a spacer for optimal distance of parts of the molecule. These further chemical groups are not used for the calculation of the molecular weight of the PEG residue. In addition, such a PEG residue can consist of one or more PEG chains which are covalently linked together. PEG residues with more than one PEG chain are called multiarmed or branched PEG residues. Branched PEG residues can be prepared, for example, by the addition of polyethylene oxide to various polyols, including glycerol, pentaerythriol, and sorbitol. Branched PEG residues are reported in, for example, EP 0 473 084, U.S. Pat. No. 5,932,462.

A PEG molecule used in a PEGylation reaction, and a PEG residue on a PEGylated protein, may each have a molecular weight of at least about 12 kDa, or at least about 20 kDa, about 20 kDa to 40 kDa, or about 30 kDa. A PEG residue may have a molecular weight of 20 kDa to 35 kDa and be a linear PEG residue. A PEG residue may have a molecular weight of 35 kDa to 40 kDa and be a branched PEG residue.

A mono-PEGylated EPO may comprise a single PEG residue having a molecular weight of at least about 12 KDa, or at least about 20 kDa, about 20 kDa to 40 kDa, about 20 kDa, or about 30 kDa. A PEG residue may have a molecular weight of at least about 20 kDa.

A mono-PEGylated protein is a protein comprising a single PEG residue. That is, the mono-PEGylated protein has one PEG residue only. An oligo-PEGylated protein comprises at least two PEG residues. For example an oligo-PEGylated protein may be a di-, tri or tetra-PEGylated protein. The term oligo-PEGylated protein (or poly-PEGylated protein) may refer to a group of oligo-PEGylated protein molecules having varying degrees of PEGylation (two, three, or more PEG residues). The term PEGylated protein refers to mono-PEGylated and oligo-PEGylated proteins. The term PEGylated protein may refer to protein consisting of mono-PEGylated and oligo-PEGylated protein. A non-PEGylated protein is a protein that does not comprise any PEG residues. A non-PEGylated protein may also be referred to in the context of a PEGylation reaction as an unreacted protein. A non-PEGylated protein may be referred to as a native protein, or an unPEGylated protein or a free protein.

The term "PEGylation" means a covalent linkage of a PEG residue with a protein. In particular it may refer to a covalent linkage at the N-terminus of the polypeptide and/or an internal lysine residue. PEGylation of proteins is widely known in the state of the art and reviewed by, for example, Veronese, F. M., Biomaterials 22 (2001) 405-417. PEG can be linked using different functional groups and polyethylene glycols with different molecular weight, linear and branched PEGs as well as different linking groups (see also Francis, G. E., et al., Int. J. Hematol. 68 (1998) 1-18; Delgado, C., et al., Crit. Rev. Ther. Drug Carrier 30 Systems 9 (1992) 249-304). PEGylation of erythropoietin can be performed in aqueous solution with PEGylation reagents as described, for example, in WO 00/44785, in one embodiment by using NHS-activated linear or branched PEG molecules of a molecular weight between 5 kDa and 40 kDa. PEGylation can also be performed at the solid phase according to Lu, Y., et al., Reactive Polymers 22 (1994) 221-229. Not randomly, N-terminally PEGylated polypeptide can also be produced according to WO 94/01451. PEGylation reactions are also reviewed in WO 2009/010270 and WO 2012/035037.

Suitable PEG derivatives are activated PEG molecules with an average molecular weight of from about 5 to about 40 kDa, or from about 20 to about 40 kDa. The PEG derivative is in one embodiment a linear or a branched PEG. A wide variety of PEG derivatives suitable for use in the preparation of PEG-protein and PEG-peptide conjugates can be obtained from Shearwater Polymers (Huntsville, AL, U.S.A.; www.nektar.com). Activated PEG derivatives are known in the art and are described in, for example, Morpurgo, M., et al., J. Bioconjug. Chem. 7 (1996) 363-368.

A PEGylation reaction may be performed at a pH of about 6.5 to 9.5, about 7.0 to 9.0, or about 7.5 to 8.5, or about 8.0. The pH at which the PEGylation reaction is performed may depend on the PEG reagent used. The PEG reagent may be mPEG-NHS, mPEG-SPA, mPEG-SVA or mPEG-Cl. The PEGylation reaction may be performed at a pH of about 7.0 to 9.0, or about 7.5 to 8.5, or about 8.0 using (NHS) activated PEG reagent. The PEGylation reaction may be performed at about 15-25° C., or about 18-22° C., or about 20° C. The PEGylation reaction may be carried out for at least about 20, 30, 40, 50 or 60 minutes, or about 30-90, or 30-60 minutes, or about 40, 50, or 60 minutes.

A PEGylation reaction may be performed in a solution comprising a salt and a buffer. The salt may be $Na_2SO_4$ and the buffer may be bicine. The salt may be present in an amount of 5-10 mM or about 7.5 mM. The buffer may be present in an amount of about 10-50 mM, 20-30 mM or about 25 mM. The PEGylation reaction may be performed in 7.5 mM $Na_2SO_4$ and 25 mM bicine.

EPO

The term "erythropoietin" and its abbreviation "EPO" refer to a protein having the amino acid sequence of SEQ ID NO: 1 or of SEQ ID NO: 2, or a protein or polypeptide substantially homologous thereto, whose biological properties relate to the stimulation of red blood cell production and the stimulation of the division and differentiation of committed erythroid progenitors in the bone marrow. Recombinant erythropoietin may be prepared via expression in eukaryotic cells, for example in CHO cells, or BHK cells, or Hela cells by recombinant DNA technology or by endogenous gene activation, i.e. the erythropoietin glycoprotein is expressed by endogenous gene activation, see for example U.S. Pat. Nos. 5,733,761, 5,641,670, 5,733,746, WO 93/09222, WO 94/12650, WO 95/31560, WO 90/11354, WO 91/06667, and WO 91/09955. The EPO may be human EPO. The EPO may be glycosylated EPO.

The human EPO may have the amino acid sequence set out in SEQ ID NO: 1 or SEQ ID NO: 2. The human EPO may have the amino acid sequence set out in SEQ ID NO: 1. The term "EPO" also denotes variants of the protein of SEQ ID NO: 1 or of SEQ ID NO: 2, in which one or more amino acid residues have been changed, deleted, or inserted, and which has comparable biological activity as the not modified protein, such as e.g. reported in EP 1 064 951 or U.S. Pat. No. 6,583,272. The number of amino acids changed, deleted or inserted may be 1, 2, 3, 4, 5, 6, 7, 8, 9, 10, 1-50, 1-40, 1-30, 1-20, or 1-10. The term EPO denotes proteins that comprise or consist of the amino acid sequence set out in SEQ ID NO:1 or SEQ ID NO:2 or variants thereof. A variant may have the amino acid sequence of human erythropoietin having from 1 to 6 additional sites for glycosylation. The specific activity of PEGylated erythropoietin can be determined by various assays known in the art. The biological activity of the purified PEGylated erythropoietin are such that administration of the protein by injection to human patients results in bone marrow cells increasing production of reticulocytes and red blood cells compared to noninjected or control groups of subjects. The biological activity of PEGylated erythropoietin obtained and purified in accordance with the method as reported herein can be tested by methods according to Bristow, A, *Pharmeuropa Spec. Issue Biologicals BRP Erythropoietin Bio* 97-2 (1997) 31-48.

Amino acid sequence variants of EPO can be prepared by introducing appropriate modifications into the nucleotide sequence encoding the EPO, or by peptide synthesis. Such modifications include, for example, deletions from, and/or insertions into, and/or substitutions of residues within the amino acid sequences of the erythropoietin. Any combination of deletion, insertion, and substitution can be made to arrive at the final construct, provided that the final construct possesses comparable biological activity to the human EPO.

Conservative amino acid substitutions are shown in the table below under the heading of "preferred substitutions". More substantial changes are provided under the heading of "exemplary substitutions", and as described below in reference to amino acid side chain classes. Amino acid substitutions may be introduced into human erythropoietin and the products screened for retention of the biological activity of human erythropoietin.

Non-conservative substitutions will entail exchanging a member of one of these classes for another class.

The EPO may be a variant EPO. The EPO may be comprised in a fusion protein with another protein, or may be conjugated to another moiety in addition to PEG.

The chemical PEGylation of erythropoietin generally results in a protein preparation comprising erythropoietin which is PEGylated at one or more ε-amino groups of lysine residues and/or at the N-terminal amino group. Selective PEGylation at the N-terminal amino acid can be performed according to Felix (1997). Selective N-terminal PEGylation can be achieved during solid-phase synthesis by coupling of a $N^\alpha$-PEGylated amino acid derivative to the N-1 terminal amino acid of the peptide chain. Side chain PEGylation can be performed during solid-phase synthesis by coupling of $N^\epsilon$-PEGylated lysine derivatives to the growing chain. Combined N-terminal and side chain PEGylation is feasible either as described above within solid-phase synthesis or by solution phase synthesis by applying activated PEG reagents to an amino deprotected peptide.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Val; Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Proteins

The processes of the invention are especially suitable for producing mono-PEGylated EPO compositions. Reference to a protein or protein of interest herein may refer to EPO.

The processes of the invention may be suitable for producing mono-PEGylated compositions of other proteins, particularly therapeutic proteins. For example interleukin-2 (IL-2), peginterferon alfa-2a, human growth hormone (hGH), bone morphogenetic protein 2 (BMP-2), bone morphogenetic protein 7 (BMP-7), bone morphogenetic protein 15 (BMP-15), neurotrophin-3 (NT-3), von Willebrand factor (VWF) protease, granulocyte colony stimulating factor (G-CSF), granulocyte-macrophage colonystimulating factor (GM-CSF), interferon alpha, interferon beta, interferon gamma, tissue-type plasminogen activator (IPA), leptin, hirudin, urokinase, human DNase, insulin, hepatitis B surface protein (HbsAg), chimeric diphtheria toxin-IL-2, human chorionic gonadotropin (hCG), thyroid peroxidase (TPO), alpha-galactosidase, alpha-L-iduronidase, beta-glucosidase, alpha-galactosidase A, acid a-glucosidase (acid maltase), anti-thrombin III (AT III), follicle stimulating hormone (FSH), glucagon-like peptide-I (GLP-1), glucagonlike peptide-2 (GLP-2), fibroblast growth factor 7 (FGF-7), fibroblast growthfactor21 (FGF-21), fibroblast growth factor 23 (FGF-23), Factor X, Factor XIII, prokinetisin, extendin-4, CD4, tumor necrosis factor receptor (TNF-R), a-$CD_{20}$. P-selectin glycoprotein ligand-I (PSGL-I), complement, transferrin, glycosylation-dependent cell adhesion molecule (GlyCAM), neural-cell adhesion molecule (N-CAM), INF receptor-IgG Fc region fusion protein. Such proteins also include antibodies such as monoclonal antibodies against any one of: respiratory syncytial virus, protein F of respiratory syncytial virus, INF-a, glycoprotein IIb/IIIa, CD20, VEGF-A, PSGL-1, CD4, a-CD3, EGF, carcinoembryonic antigen (CEA), TNFα and IL-2 receptor.

The processes of the invention may be suitable for producing mono-PEGylated compositions of proteins such as hormones, cytokines or enzymes. Such a protein may be erythropoietin. The protein may be interferon-α-2a or interferon-α-2b. The protein may be granulocyte colony-stimulating factor, human growth hormone, or urate oxidase.

The invention is particularly useful for therapeutic proteins having a relatively short half-life, because PEGylation increases in vivo circulation half-life. Generally hormones and cytokines have a relatively short half-life. Smaller biological molecules tend to have a relatively short half-life. The pharmacokinetic profile of relatively small biological molecules may be improved by PEGylation and so the present invention may also be particularly useful for relatively small therapeutic proteins. Generally proteins and peptides smaller than approximately 70 kDa are more likely to be eliminated by kidney filtration than are larger proteins. Smaller biological molecules, or proteins, may be defined as those having a molecular weight of less than about 70 kDa. Erythropoietin has a molecular weight of about 37 kDa. The invention is useful for therapeutic proteins having a molecular weight less than about 70 kDa (in their non-PEGylated form). The invention is useful for therapeutic proteins having a molecular weight less than about 70 kDa, 60 kDa, 50 kDa, or 40 kDa, or having a molecular weight of about 10-70 kDa, 20-60 kDa, 20-50 kDa, or 30-40 kDa. The invention is useful for hormones or cytokines having a molecular weight less than about 70 kDa, 60 kDa, 50 kDa, or 40 kDa, or having a molecular weight of about 10-70 kDa, 20-60 kDa, 20-50 kDa, or 30-40 kDa.

The protein may be an antibody. An antibody may be a polyclonal antibody or a monoclonal antibody. An antibody may be a biologically functional antibody fragment. Antibody fragments include Fab, Fab', F(ab') 2, scFv, (scFv) 2, single-domain antibodies (sdAb, or dAB), complementarity determining region fragments, linear antibodies, single-chain antibody molecules, minibodies, diabodies and multispecific antibodies formed from antibody fragments. Many antibody fragments have a relatively short half-life in vivo, which results from their relatively small size and their no longer having an Fc region. The invention is particularly useful for antibody fragments having a relatively small size, such as single-domain antibodies, Fabs, Fab's, and scFvs. The invention is useful for antibody fragments having a molecular weight less than about 70 kDa, 60 kDa, 50 kDa, or 40 kDa, or having a molecular weight of about 10-70 kDa, 20-60 kDa, 20-50 kDa, or 30-40 kDa.

The mono-PEGylated protein compositions may be formulated as pharmaceutical compositions. The mono-PEGylated protein compositions produced by the processes disclosed herein may be formulated with one or more pharmaceutically acceptable excipients, and/or may be formulated in a physiologically acceptable buffer such as physiological saline. The salts and/or buffers used in the equilibration, wash, or elution buffers of the HIC step may be removed before formulating the mono-PEGylated protein composition as a pharmaceutical composition. For example the mono-PEGylated protein compositions may be dialysed. The mono-PEGylated protein of the mono-PEGylated protein composition may be lyophilised. The mono-PEGylated protein of the mono-PEGylated protein composition may be isolated and reformulated in a pharmaceutical composition.

The processes disclosed herein may be industrial scale processes. An industrial scale process may be a process that produces at least about 5 g, 10 g, 25 g, 50 g, 100 g, 250 g or 500 g per batch or per cycle. A batch or cycle in this context may be a process comprising all of the steps a) to c) as disclosed herein. An industrial scale process may be a process in which the volume of the first mixture (comprising non-PEGylated, mono-PEGylated and oligo-PEGylated protein) that is subjected to the AEC step is at least 100 L, 500 L, 1000 L, 5000 L, 10000 L, 50000 L, or 100000 L.

The invention includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting.

Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

All references mentioned above are hereby incorporated by reference.

EXAMPLES

The following examples, including the experiments conducted and the results achieved, are provided for illustrative purposes only and should not be construed to include all possible embodiments along with the full scope of equivalents to which such claims are entitled.

Example 1

EPO was PEGylated using NHS-activated PEG reagent (molecular weight of about 30 kDa) at pH 8.0 in 25 mM bicine and 7.5 mM $Na_2SO_4$ to provide a mixture of reaction products ("first mixture") comprising non-PEGylated EPO, mono-PEGylated EPO and oligo-PEGylated EPO.

The first mixture was subjected to AEC at pH 8.0, 25 mM bicine, 7.5 mM $Na_2SO_4$. The AEC resin was Toyopearl SuperQ 650M. This has a dynamic binding capacity for EPO of about 34 g/L. Elution was carried out by a step elution to 25 mM bicine, 35 mM sodium sulphate at pH 8. Non-PEGylated EPO recovered by elution was recycled into a subsequent PEGylation reaction, the product of which (a subsequent "first mixture") was subjected to a second AEC step. This process was repeated again, such that the process included three cycles of PEGylation and AEC steps.

Figure 4:
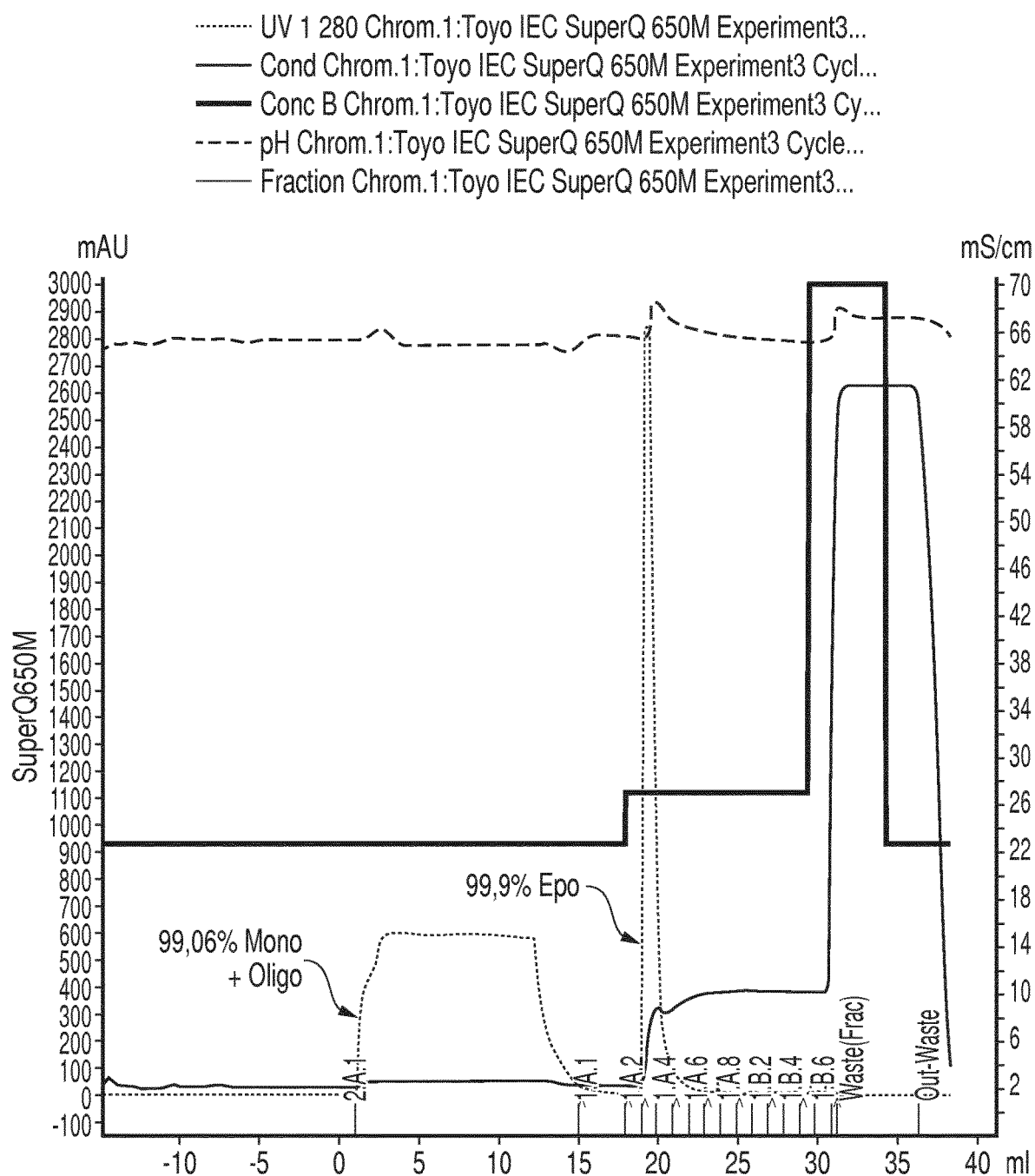
FIG. 4: Chromatogram of samples from AEC in flow through mode, showing recovery of EPO from the PEGylation reaction mixture in the flow-through and eluate fractions. Mono-PEGylated EPO and oligo-PEGylated EPO are present in the flow-through solution. EPO can be recovered by step elution almost quantitatively and in high purity for a further PEGylation reaction. The composition of fractions was determined by RP-HPLC.
Figure 5A:
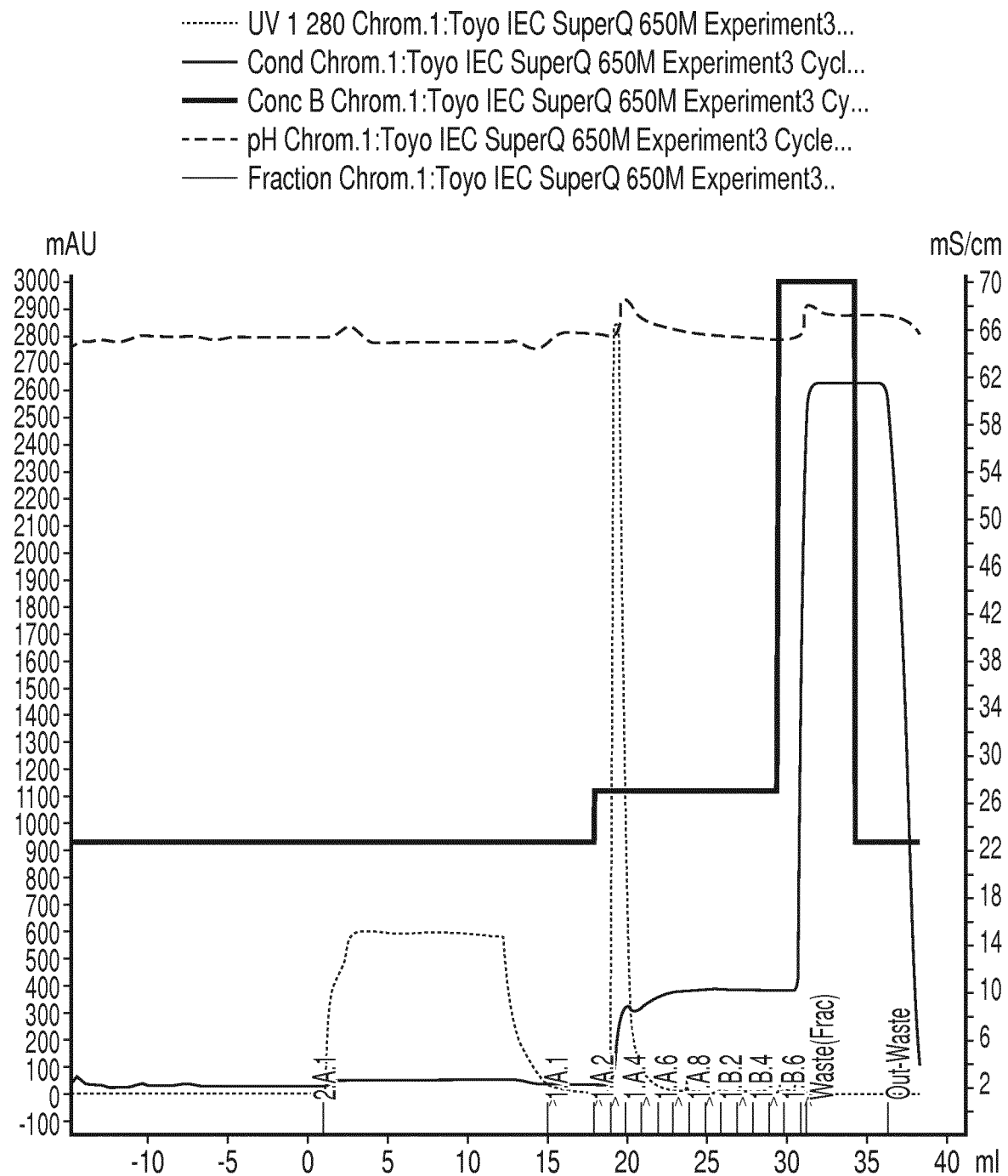
FIGS. 5A-5C: Example AEC chromatograms for the recovery of EPO from the PEGylation reaction mixture in three sequential cycles (FIGS. 5A, 5B and 5C). The total amount of EPO in cycles 2 and 3 is reduced, because only unreacted EPO recovered from the previous cycle was used for PEGylation in cycles 2 and 3. Mono-PEGylated and oligo-PEGylated EPO are present in the flow-through solution. Unreacted EPO can be recovered by step elution almost quantitatively and in high purity for further PEGylation reactions. The composition of fractions was determined by RP-HPLC.
Figure 5B:
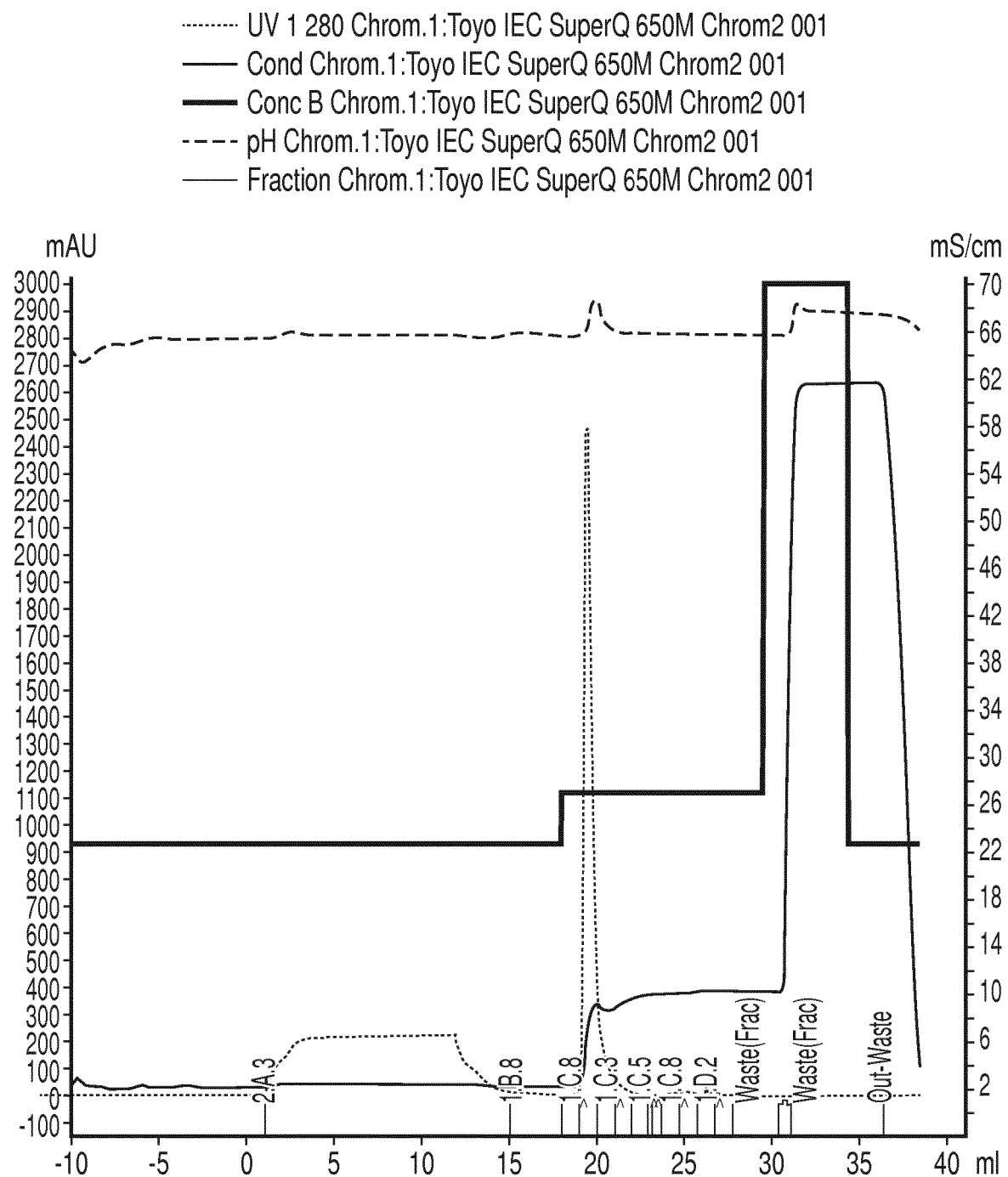
Figure 5C:
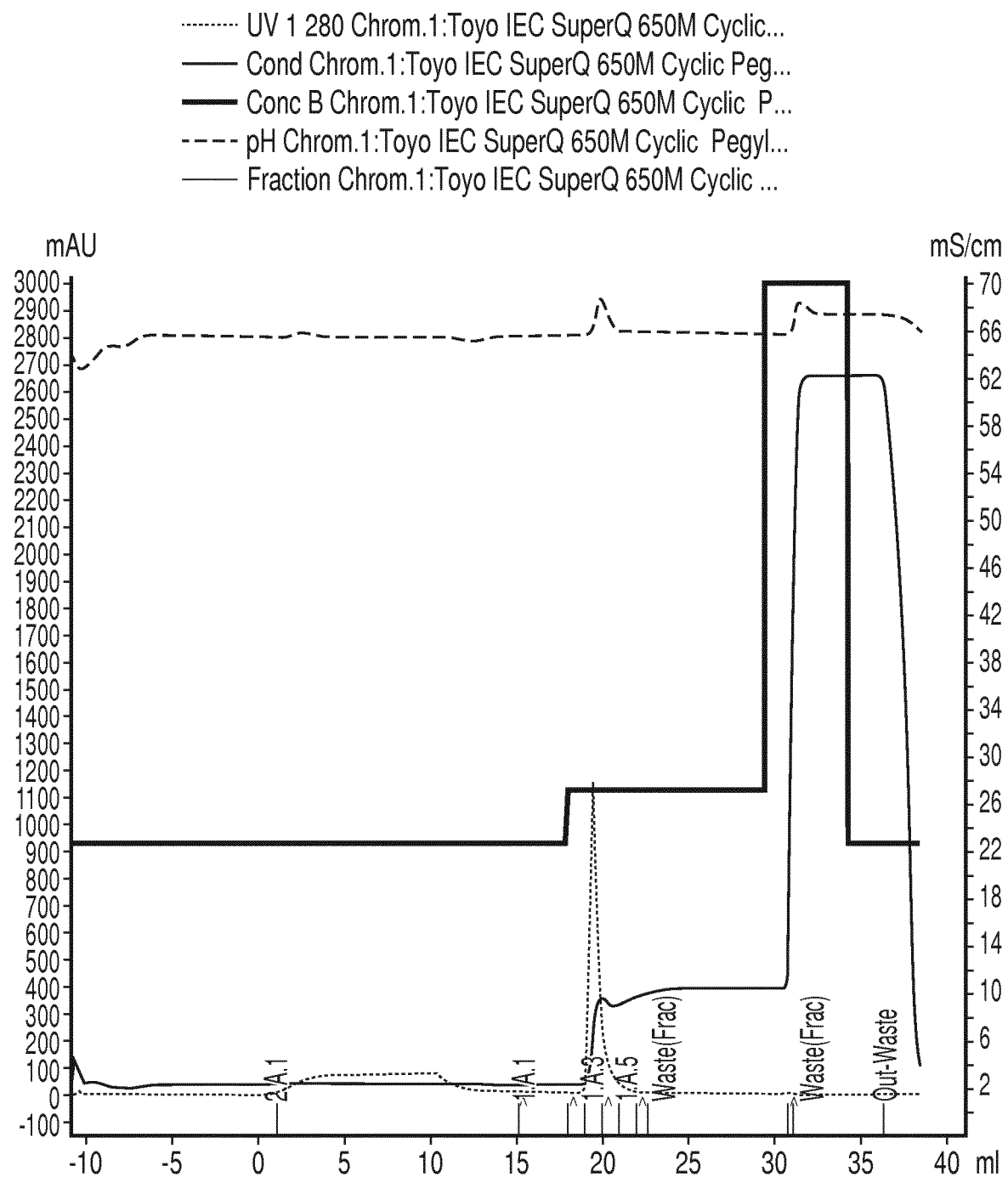

A chromatograph showing protein elution in an AEC step is shown in FIG. 4. Three chromatographs showing the three AEC steps are shown in FIGS. 5A-5C, which shows that the amount of EPO in the second cycle is less than in the first, and the amount of EPO in the third cycle is less than in the second.

Table 1 shows the contents of the various intermediate compositions. The PEGylation product is the "first mixture", the product pool is the AEC flow-through solution, and the epo pool is the AEC eluate.

TABLE 1

| | Conc [g/l] | Vol [ml] | Mass [mg] | Composition [%] | | | Mass [mg] | | |
|---|---|---|---|---|---|---|---|---|---|
| | | | | Epo | Mono | Oligo | Epo | Mono | Oligo |
| EPO start | 8.71 | 5.74 | 50.0 | 100.0 | 0 | 0 | 50.0 | 0 | 0 |
| *PEGylation 1* | | | | | | | | | |
| PEGylation product | 5 | 9.5 | 47.5 | 51.12 | 40.1 | 8.79 | 24.28 | 19.05 | 4.18 |
| *Chromatography 1* | | | | | | | | | |
| Product pool | 1.97 | 14 | 27.58 | 0.94 | 80.01 | 19.06 | 0.26 | 22.07 | 5.26 |
| EPO pool | 8.9 | 2 | 17.8 | 100 | 0 | 0 | 17.8 | 0 | 0 |
| *PEGylation 2* | | | | | | | | | |
| PEGylation product | 2.48 | 7.0 | 17.37 | 50.46 | 40.19 | 9.35 | 8.77 | 6.98 | 1.62 |
| *Chromatography 2* | | | | | | | | | |
| Product pool | 0.68 | 14 | 9.52 | 0.57 | 78.89 | 19.55 | 0.05 | 7.61 | 1.86 |
| EPO pool | 3.21 | 2 | 6.42 | 100 | 0 | 0 | 6.42 | 0 | 0 |
| *PEGylation 3* | | | | | | | | | |
| PEGylation product | 0.80 | 6.7 | 5.3 | 57.62 | 37.03 | 5.35 | 3.05 | 1.96 | 0.28 |
| *Chromatography 3* | | | | | | | | | |
| Product pool | 0.19 | 14 | 2.62 | 0 | 86.18 | 13.82 | 0 | 2.26 | 0.36 |
| EPO pool | 1.34 | 2 | 2.68 | 96.98 | 2.6 | 0 | 2.6 | 0.07 | 0 |
| Pooled Product (Chromatography 1-3) | 0.95 | 42.0 | 39.8 | 0.9 | 79.7 | 19.5 | 0.3 | 31.7 | 7.7 |
| Yield (EPO conversion to mono-PEG product) % after 3 cycles | | | | | | 63.4 | | | |

The ability of HIC to separate mono-PEGylated EPO from oligo-PEGylated EPO was then investigated in both bind and elute mode and flow-through mode.

Figure 6:
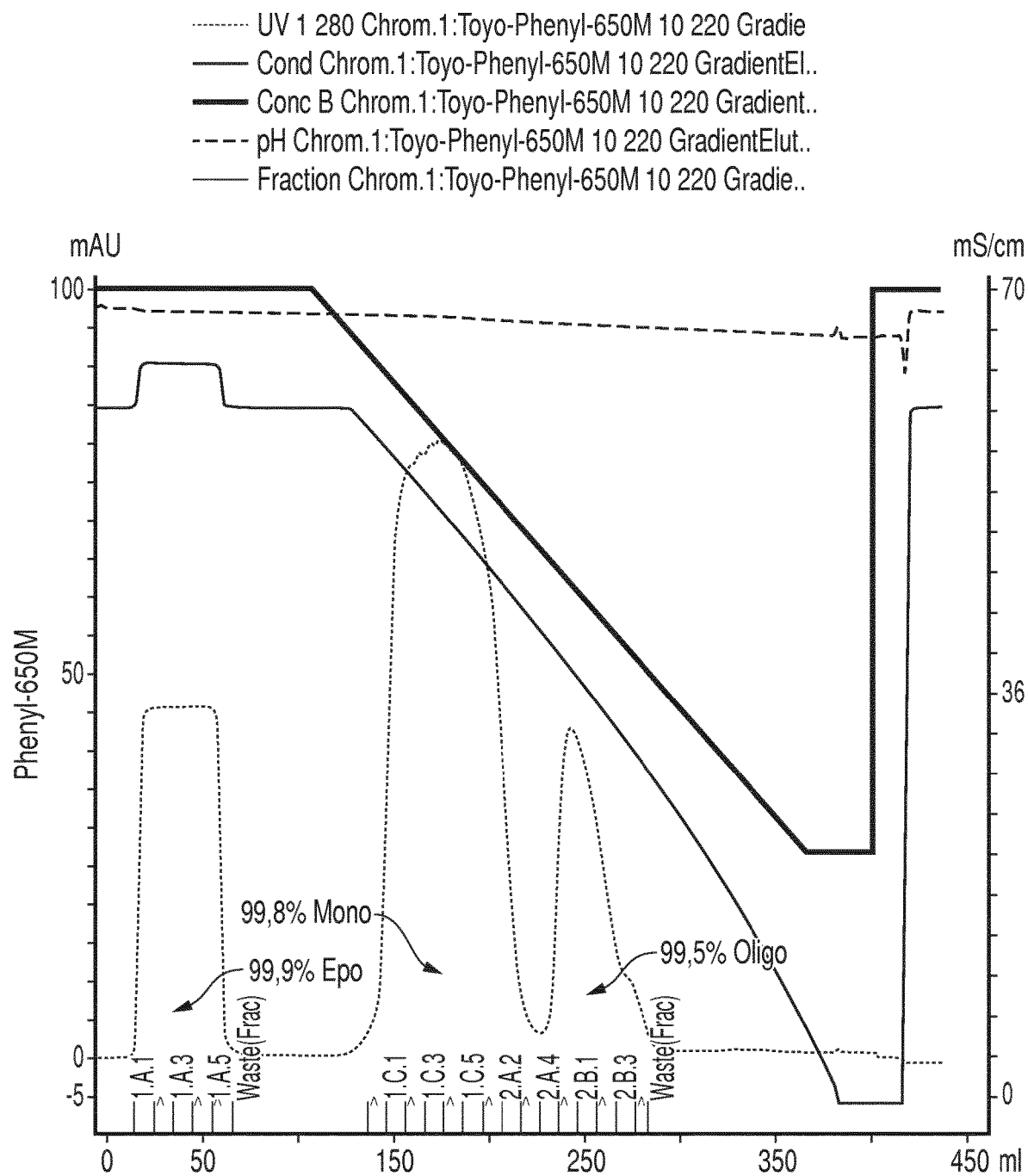
FIG. 6: Example HIC chromatogram for the performance of the purification on Toyopearl Phenyl 650 M in bind and elute mode. Non-PEGylated EPO was removed in the flow-through solution at 500 mM $Na_2SO_4$. In a falling $Na_2SO_4$ gradient, mono-PEGylated EPO elutes at approximately 300 mM $Na_2SO_4$ with good resolution from the oligo species. The composition of fractions was determined by RP-HPLC.

In bind and elute mode the HIC resin was Toyopearl Phenyl-650M. The resin was equilibrated with 25 mM bicine and 500 mM $Na_2SO_4$ at pH 8.0. The mixture applied to the resin comprised non-PEGylated EPO, mono-PEGylated EPO and oligo-PEGylated EPO for testing purposes. The mixture was conditioned with 25 mM bicine and 500 mM $Na_2SO_4$ at pH 8.0 and applied to the HIC resin. An elution gradient of decreasing salt concentration was applied, from 500 mM to 0 mM $Na_2SO_4$. FIG. 6 is a chromatogram showing that EPO is in the flow-through, and that mono-PEGylated EPO is eluted at relatively high salt whereas oligo-PEGylated EPO is eluted at relatively low salt.

Figure 7:
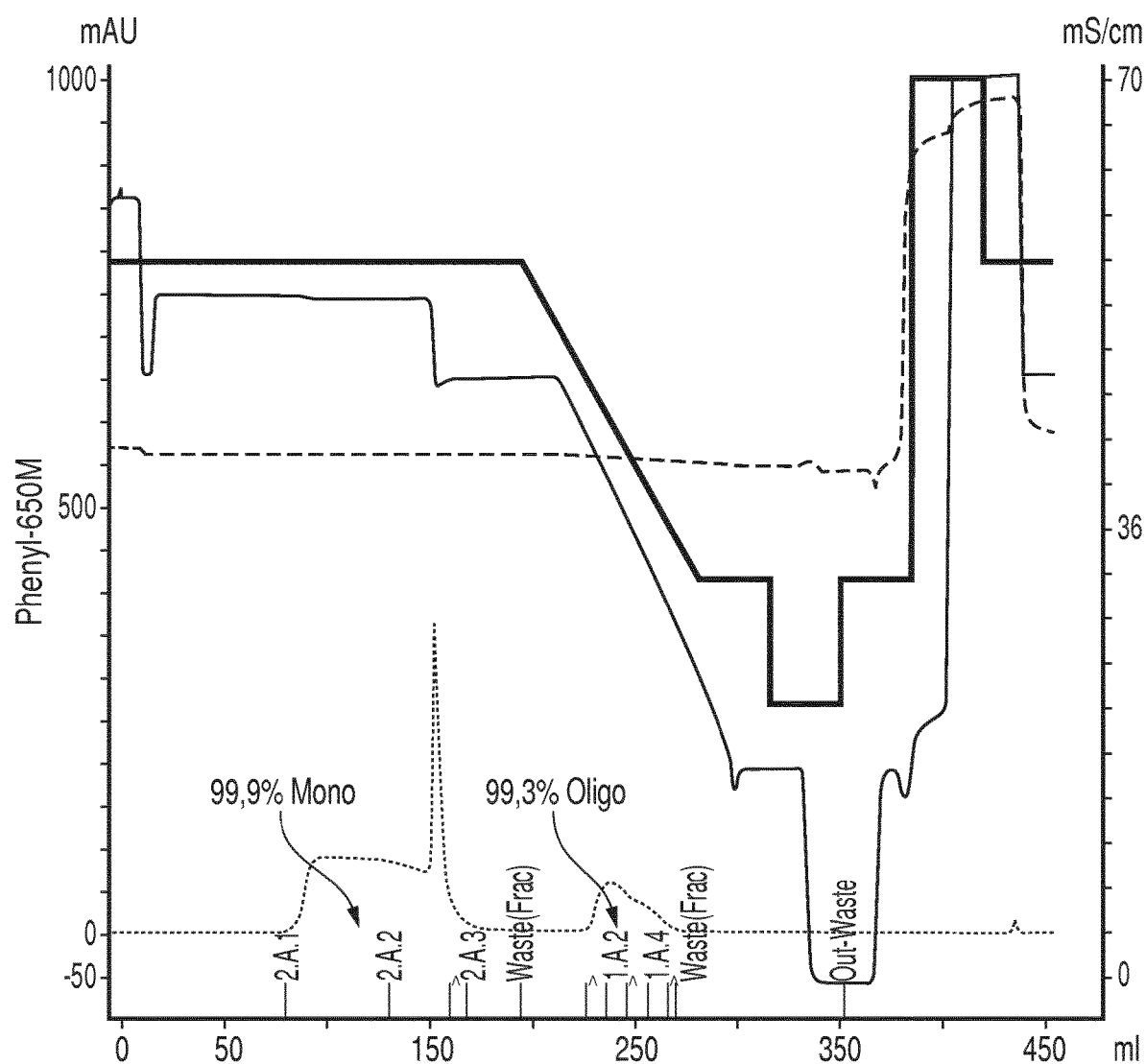
FIG. 7: Example HIC chromatogram for the performance capacity of the purification on Toyopearl Phenyl 650 M in flow through mode. Mono-PEGylated EPO is present in the flow-through solution at about 300 mM $Na_2SO_4$. The oligo-PEGylated EPO species remain on the column until regeneration. The composition of fractions was determined by RP-HPLC.

In flow-through mode the HIC resin was Toyopearl Phenyl-650M. The resin was equilibrated with 25 mM bicine and 390 mM $Na_2SO_4$ at pH 8.0. The mixture applied to the resin comprised mono-PEGylated EPO and oligo-PEGylated EPO, it did not contain significant amounts of non-PEGylated EPO and is therefore representative of a "second mixture" in accordance with the invention. The mixture was conditioned with bicine and $Na_2SO_4$ at pH 8.0 and applied to the HIC resin. The salt concentration was adjusted to 390 mM. FIG. 7 is a chromatogram showing that mono-PEGylated EPO is in the flow-through. Oligo-PEGylated EPO was eluted using a decreasing salt gradient.

Example 2

PEGylation of EPO

EPO stock solution was thawed, concentrated to 6.5 g/l using 3 kDa Centricon centrifugal filters, and buffered in 25 mM bicine, pH 8. 7.7 ml of this solution was then transferred into a 50 ml Falcon tube and mixed with 0.3 ml of 25 mM bicine, pH 8 buffer. 96 mg of PEG reagent was weighed and dissolved in 3 ml of 1 mM HCl to prepare the PEGylation solution.

The PEGylation reaction was started by addition of 2 ml of PEGylation solution (molecular weight of about 30 kDa) to the EPO solution. The reaction was carried out in a water bath at 20° C. for 50 minutes.

Cyclic PEGylation and Purification Using Ion Chromatography

As a first step, PEGylated EPO was produced as outlined above. 1 ml of the PEGylated EPO solution was transferred to an Eppendorf cup, and the remaining 9 ml was injected into a 150 ml Superloop using a 50 ml syringe and anion exchange chromatography started.

Figure 8A:
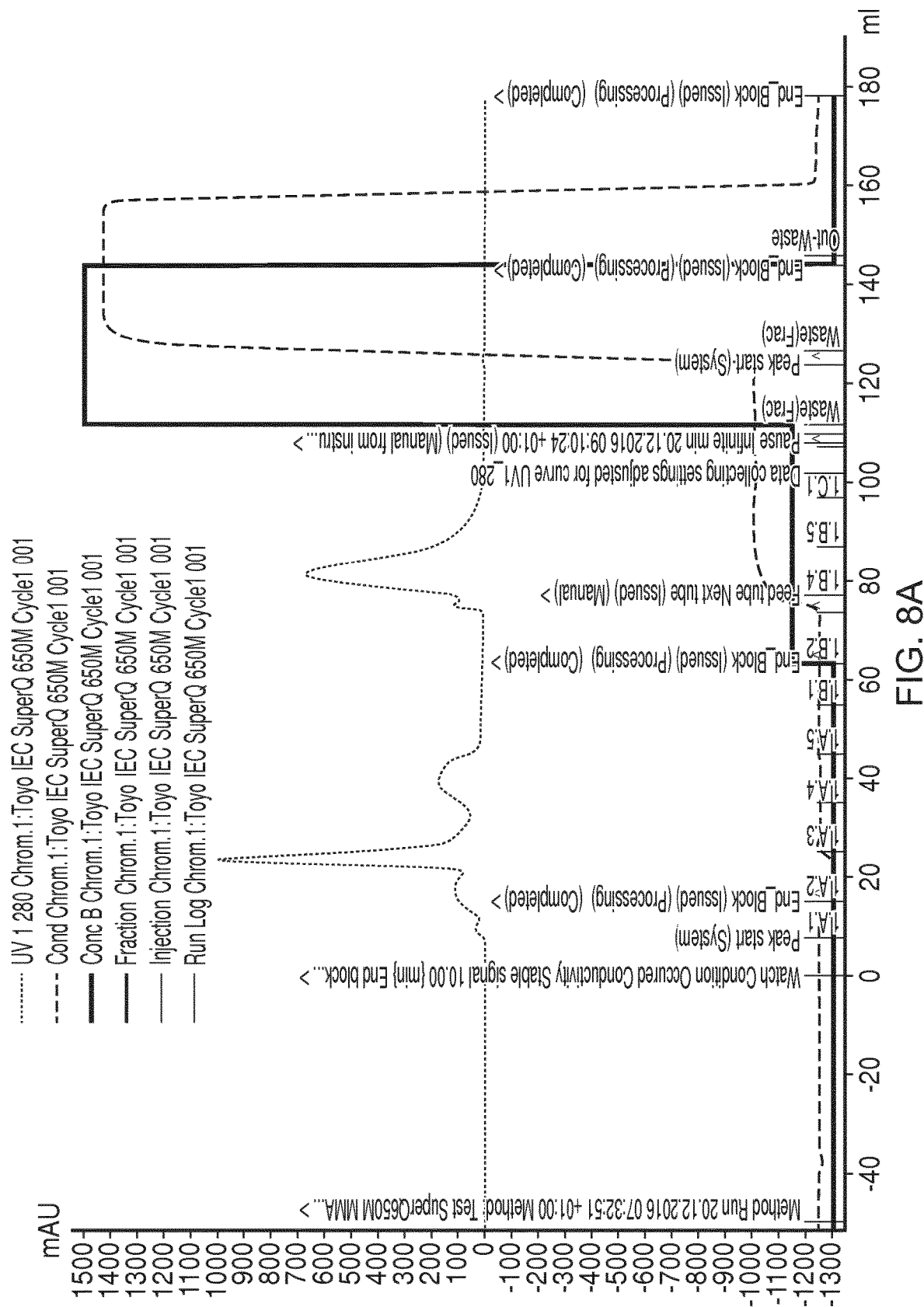
FIGS. 8A, 8B and 8C show AEC chromatograms for recovery of EPO from the PEGylation reaction mixture in three sequential cycles.

A 16 ml Toyopearl SuperQ-650M with a diameter of 1 cm was used as the anion exchange chromatography column. The column was equilibrated with a 25 mM bicine, 7.5 mM $Na_2SO_4$, pH 8 buffer. Elution was carried out by a step elution to 25 mM bicine, 35 mM sodium sulphate at pH 8. The corresponding chromatogram is shown in FIG. 8A.

1 ml of fraction 1B3 was removed and its composition measured by HPLC. Subsequently, fractions 1B3 to 1C1 were combined, and the composition of a 1 ml sample of this mixed fraction also measured by RP HPLC. The protein concentration was determined photometrically, and at an extinction coefficient of 1.25 was 0.097 g/l. This mixed fraction (AEC eluate) is from the elution step.

The remaining 21 ml of the mixed fraction was transferred into a 50 ml Falcon tube and placed in a 20° C. water bath for renewed PEGylation. 1 ml of a 26.89 g/l PEGylation reagent solution was added and the second PEGylation reaction started.

Figure 8B:
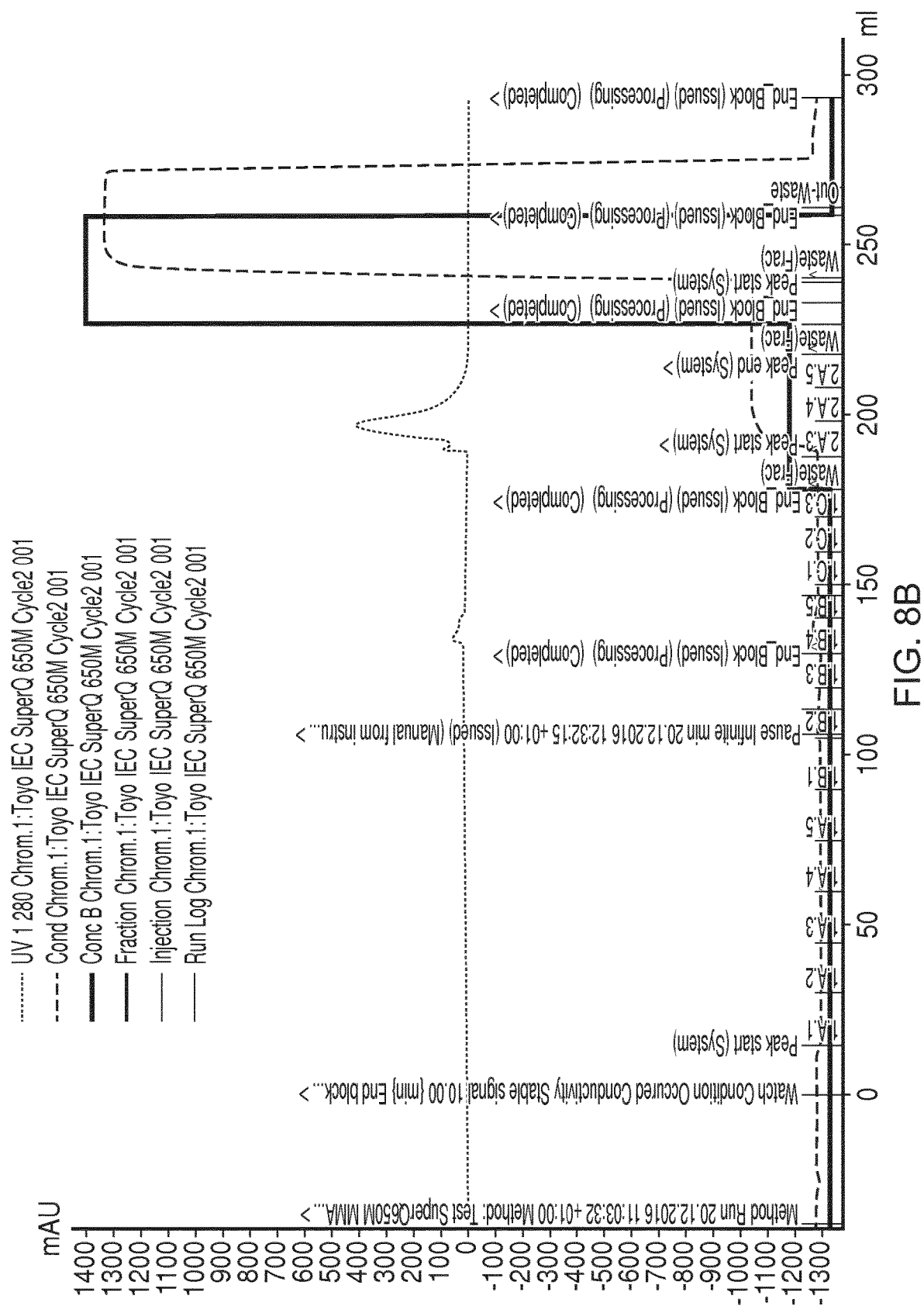

The AEC eluate (EPO-fraction) is at the same conditions (35 mM sodium sulphate) as the elution buffer of the first chromatography, outlined above. The reaction solution was diluted by a factor of 4.66 with 25 mM bicine buffer after 50 min and thus adjusted to the equilibration conditions. The resulting 97.9 ml sample was again injected into the 150 ml Superloop and the second chromatography was started. The chromatography method was changed only in terms of the larger sample volume. All other parameters and ingredients remained unchanged. The corresponding chromatogram is shown in FIG. 8B.

Fractions 2A3 to 2A5 were pooled again and the procedure above repeated as a third cycle.

Figure 8C:
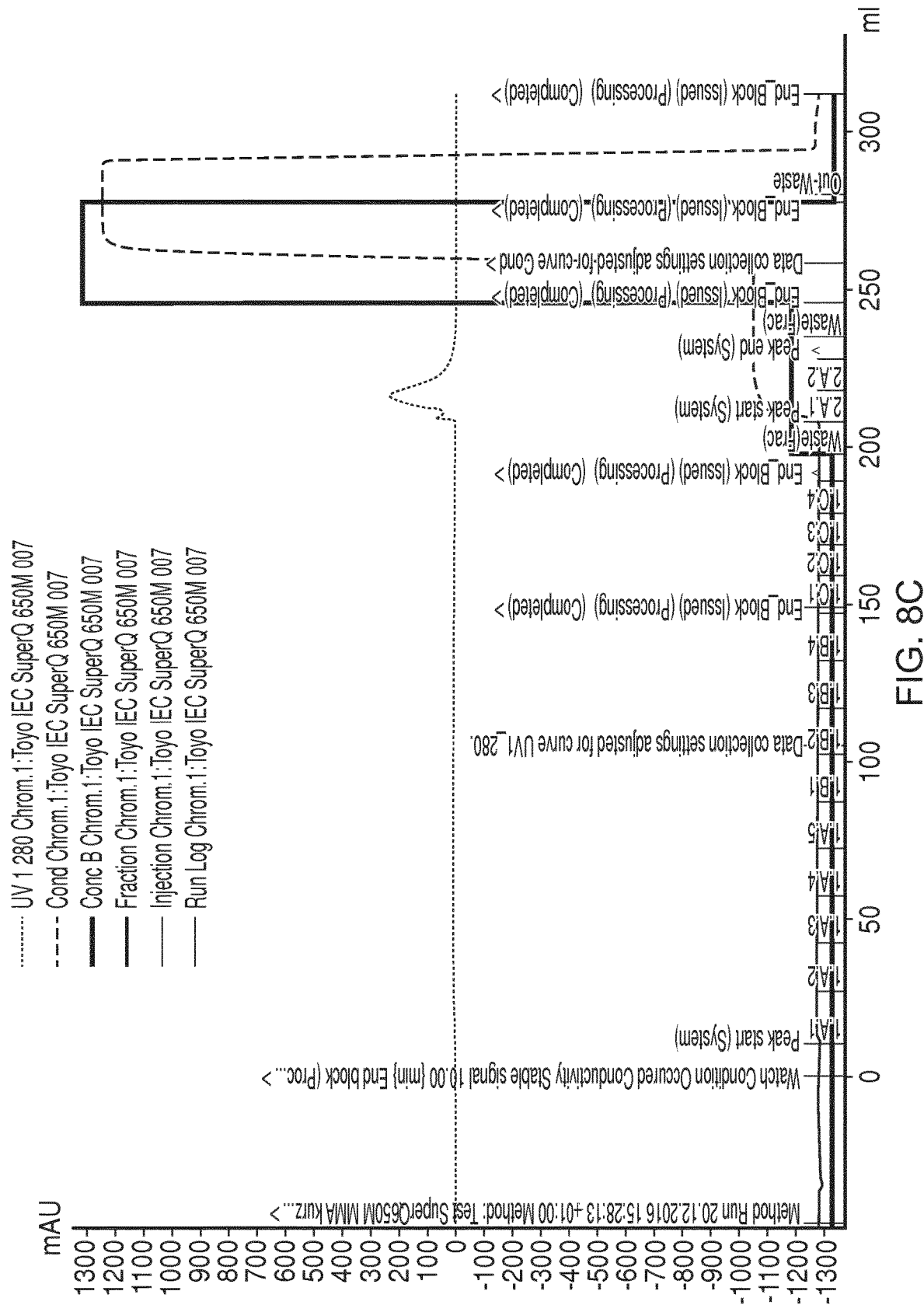

Fractions 1A1 to 1C5 of the third chromatography were combined and concentrated using 3 kDa Centricon centrifugal filters. The concentrate and the pools of the fractions 2A1 to 2A3 were measured by RP HPLC. The corresponding chromatogram is shown in FIG. 8C.

All pipetted volumes of the PEGylation reactions and the dilution steps are listed in Table 2.

TABLE 2

Volumes of starting ingredients and samples

| Cycle | Vsample [ml] | Cprotein [g/l] | Vdiluted [ml] | VPEG reagent [ml] | CPEG reagent [g/l] | stoichiometry [MPEG/MEPO] |
|---|---|---|---|---|---|---|
| 1 | 10 | 5.00 | — | 2 | 33.00 | 0.8 |
| 2 | 21 | 0.97 | 98.7 | 1 | 26.89 | 0.8 |
| 3 | 30 | 0.47 | 141.0 | 1 | 33.50 | 1.44 |

Results and Discussion

The measured results of the RP HPLC analysis are shown in Table 3. The percentage by mass of EPO in the cyclically PEGylated EPO pools is on average about 95%.

TABLE 3

Composition before and after PEGylation reaction and chromatographic separation

| Sample description | Fraction | Epo [%] | Mono-PEG Epo [%] | Oligo Forms [%] |
|---|---|---|---|---|
| Starting material | — | 100 | 0 | 0 |
| PEGylation product 1 | — | 49.06 | 41.38 | 9.55 |
| PEGylation product 2 | — | 62.36 | 32.88 | 4.77 |
| PEGylation product 3 | — | 51.95 | 39.82 | 8.24 |
| Cycle 1 Pool | 1A1 - 1C1 | 96.59 | 2.05 | 1.3 |
| Cycle 1 B3 | 1B3 | 35.22 | 64.23 | 0.55 |
| Cycle 2 Pool | 2A3 - 2A5 | 94.68 | 3.05 | 2.27 |
| Cycle 3 Pool | 2A1 - 2A3 | 94.24 | 3.35 | 2.18 |

The mass balance for each cycle is listed in Table 4, as well as for the entire process. It should be noted that the information on the product pools is not based on measured values, but has been calculated.

TABLE 4

Mass balances

| Description and process step | Mass [mg] | Composition [%] | | | Composition [mg] | | |
|---|---|---|---|---|---|---|---|
| | | Epo | Mono-PEG Epo | Oligo | Epo | Mono-PEG Epo | Oligo |
| PEGylation 1 | 50 | 49.06 | 41.38 | 9.55 | 24.53 | 20.69 | 4.78 |
| Chromatography 1 | | | | | | | |
| Product Pool 1 | 24.91 | 0.7 | 80.07 | 19.23 | 0.17 | 19.94 | 4.79 |
| 1B3 | 0.78 | 35.22 | 64.23 | 0.55 | 0.28 | 0.50 | 0.00 |
| Epo Pool 1 | 21.37 | 96.59 | 2.05 | 1.35 | 20.64 | 0.44 | 0.29 |
| PEGylation 2 | 21.37 | 62.36 | 32.88 | 4.77 | 13.33 | 7.03 | 1.02 |
| Chromatography 2 | | | | | | | |
| Product pool 2 | 7.72 | 5.21 | 85.60 | 9.19 | 0.40 | 6.61 | 0.71 |
| Epo Pool 2 | 13.65 | 94.68 | 3.05 | 2.27 | 12.92 | 0.42 | 0.31 |
| PEGylation 3 | 13.65 | 51.95 | 39.82 | 8.24 | 7.09 | 5.44 | 1.12 |
| Chromatography 3 | | | | | | | |
| Product pool 3 | 6.10 | 0.00 | 84.54 | 15.46 | 0.00 | 5.16 | 0.94 |
| Epo Pool 3 | 8.35 | 94.24 | 3.35 | 2.18 | 7.87 | 0.28 | 0.18 |
| Balance (1B3 + Sum Product Pools + EPO Pool 3) | 47.83 | 23.99 | 63.62 | 12.38 | 8.72 | 32.49 | 6.62 |
| Sum of Product pools | 38.7 | 1.4 | 82.0 | 16.6 | 0.57 | 31.71 | 6.44 |

There was a 95.5% recovery over all samples at the end of the process. A loss of 4.5% of total protein was observed due to sampling and analytics. EPO Pool 1 and EPO Pool 2 were consumed in PEGylation 2 and 3. 63.6% of initial EPO was converted to mono-PEG-EPO. 82.0% mono-PEG-EPO content in intermediate pool.

On the basis of the mass balance it can be seen that 32.5 mg of mono-PEGylated EPO could be prepared from the 50 mg unPEGylated EPO used, which exists as a mixture of 1.4% Epo, 82.0% mono-PEG Epo and 16.6% oligo-forms. Thus the AEC step produced a solution (AEC flow through solution) comprising 82% mono-PEGylated EPO (82% purity).

The reaction yield of mono-PEG-EPO is 63.6%. That is, of the amount of EPO protein at the start of the process (50 mg) 63.6% was converted to mono-PEGylated EPO (32.5 mg). Compared to the prior art process of WO 2009/010270, in which the PEGylation reaction is carried out only once with a yield of about 44%, this corresponds to a yield increase of about 44%.

For technical reasons in this experiment it was not possible to remove all EPO from the flow through on the AEC after the $2^{nd}$ PEGylation reaction. The resulting composition of the $2^{nd}$ reaction is therefore different from the expected values. PEGylation 1 and 3 delivered approximately 50% EPO, 40% mono-PEG-EPO and <10% Oligo-PEG-EPO. The $2^{nd}$ PEGylation reaction was less effective, producing only 33% of mono-PEG EPO and 5% of oligo-PEG-EPO.

These results demonstrate that AEC can isolate and recover unreacted EPO from the PEGylation reaction mixture without much of the PEGylated forms. The sum of the PEGylated forms in the recovered EPO fraction is about 5%—this might be due to the fact that the AEC column employed in this particular experiment was oversized. When sized to fit, the capacity for PEGylated species is expected to diminish due to displacement effects or competition for ligands.

These results also show that in cycle 1 and cycle 3 that it is possible to remove EPO almost quantitatively by applying anion exchange chromatography. The intermediate product passes through the column in the flow through, and is usually of a composition about 80% mono-PEG-EPO and 20% oligo-PEG-EPO.

Example 3

Cyclic PEGylation, Removal of Erythropoietin by AEC Chromatography, and Purification of Mono-PEG EPO by HIC The aim of this experiment is to PEGylate EPO in 3 cycles and to separate the reaction products (non-PEGylated EPO, single PEGylated EPO (mono-PEG EPO) and oligo-PEGylated forms of EPO) using anion exchange chromatography (AEC) and HIC.

To remove the EPO in the AEC stage, Toyopearl SuperQ-650M from Tosoh Bioscience was used as the adsorbent. This is a strong anion exchanger. To separate mono-PEG EPO from the oligo forms in the HIC stage, Toyopearl Phenyl-650M from Tosoh Bioscience was used.

Design of the AEC Column

A column with an inside diameter of 7 mm and a bed height of 100 mm was packed with Toyopearl SuperQ-650M adsorber material and operated at a flow rate of 200 cm/h (1.28 ml/min), resulting in a process step time of about 30 min at a column volume of 3.847 ml.

Cyclic PEGylation and AEC

An EPO stock solution with a concentration of 12.5 g/l in 25 mM bicine, 7.5 mM $Na_2SO_4$ was used. A starting volume of 18 ml of this stock solution, corresponding to 225 mg EPO, was used.

For the first PEGylation reaction, 18 ml of EPO stock solution was mixed with 22.5 ml of 25 mM bicine, 7.5 mM $Na_2SO_4$ and placed in a 50 ml Falcon tube.

328 mg of PEG reagent (molecular weight of about 30 kDa) was weighed into a 15 ml Falcon tube and dissolved in 4.97 ml of 1 mM HCl.

To start the reaction, 4.5 ml of the PEG reagent solution was pipetted into the 40.5 ml EPO solution.

The reaction mixture was mixed at 300 rpm, and the temperature adjusted to 20° C. by means of a cryostat.

The reaction was run for 60 min. The concentration was then measured photometrically at 280 nm and a 250 µl sample was taken. The concentration was 5.56 g/l. The conductivity was measured from the remaining solution. It was 2.19 mS/cm, so no conditioning to equilibration conditions of the AEX Chromatography (2.21 mS/cm) was performed. The remaining 44.8 ml solution was purified by means of AEC. It was equilibrated with 25 mM bicine, 7.5 mM $Na_2SO_4$, pH 8.

Elution was carried out stepwise with 25 mM bicine, 35 mM $Na_2SO_4$. Fractions 1B1-1B4 were combined with each other to make 16.5 ml and hereinafter will be referred to as EPO pool 1. The concentration of EPO pool 1 was photometrically determined at 5.263 g/l. A 200 µl sample was taken.

Fractions 1A1-1A5 were combined to make 62.17 ml and hereinafter are referred to as product pool 1. The concentration of this was 2.27 g/l. A 500 µl sample was taken.

The remaining volume of the EPO pool 1 was transferred to a 50 ml Falcon tube for second PEGylation. 164.73 mg of PEG reagent was weighed and dissolved with 2.4 ml of 1 mM HCl. 1.62 ml of this solution was added to the EPO Pool 1 and the second PEGylation reaction started. The reaction was again carried out at 20° C. for 60 min. Then the concentration was measured, a 250 µl sample was taken. The concentration was 4.73 g/l.

The conductivity of the remaining solution was adjusted to a conductivity of 2.1 mS/cm using 22 ml of 25 mM bicine, pH 8 buffer and purified by chromatography.

Fractions 1B2-1B4 of the second chromatography were combined to make EPO pool 2. The volume was 15 ml. A 500 µl sample was taken. The concentration measurement gave a concentration of 2.5 g/l.

Fractions 1A1-1A5 were combined with 62.7 ml of product pool 2. A 2 ml sample was taken. The concentration was 0.75 g/l.

The remaining volume of EPO pool 2 was transferred to a 50 ml Falcon tube. 119.4 mg of PEG reagent was weighed and dissolved with 1.9 ml of 1 mM HCl. 1.72 ml of this solution was added to EPO pool 2 and the third PEGylation reaction was started. It was again carried out at 20° C. After a reaction time of 60 min, the concentration was determined and a 500 µl sample was taken. The concentration was 2.8 g/l.

The reaction product was again adjusted to equilibration conditions by means of 25 mM bicine buffer and purified by chromatography.

Fractions 1C2-1C5 were combined to make 15 ml EPO pool 3. A 4 ml sample was taken from this. The concentration was 0.429 g/l.

Fractions 1A1-1C1 were combined to 160.5 ml of Product pool 3. The concentration was 0.15 g/l. A 10 ml sample was taken.

Purification of Mono-PEG EPO Using HIC

A 220 mm high column having an inner diameter of 10 mm was used. The adsorbent used was Toyopearl Phenyl-650M from Tosoh. The volume of the column was 17.27 ml. It was operated with a flow of 150 cm/h. This column was used to extract the target product mono-PEG EPO from a mixture of mono-PEG EPO and oligo.

For this purpose, two experiments were carried out. In the first, mono-PEG EPO and oligo were bound to the column material and then selectively eluted via a gradient. In the second, the oligo forms were bound to the column material while the mono-PEG EPO was not.

Separation in HIC Bind & Elute Mode

From Product pool 1 described above (a "second mixture" in accordance with the processes disclosed herein; protein concentration of 2.27 g/l) 15 ml was taken and adjusted to a conductivity of 56 mS/cm with 20 ml, 25 mM bicine, 1 M $Na_2SO_4$ PH 8 solution. This sample was completely dispensed through a 150 ml Superloop.

Figure 9:
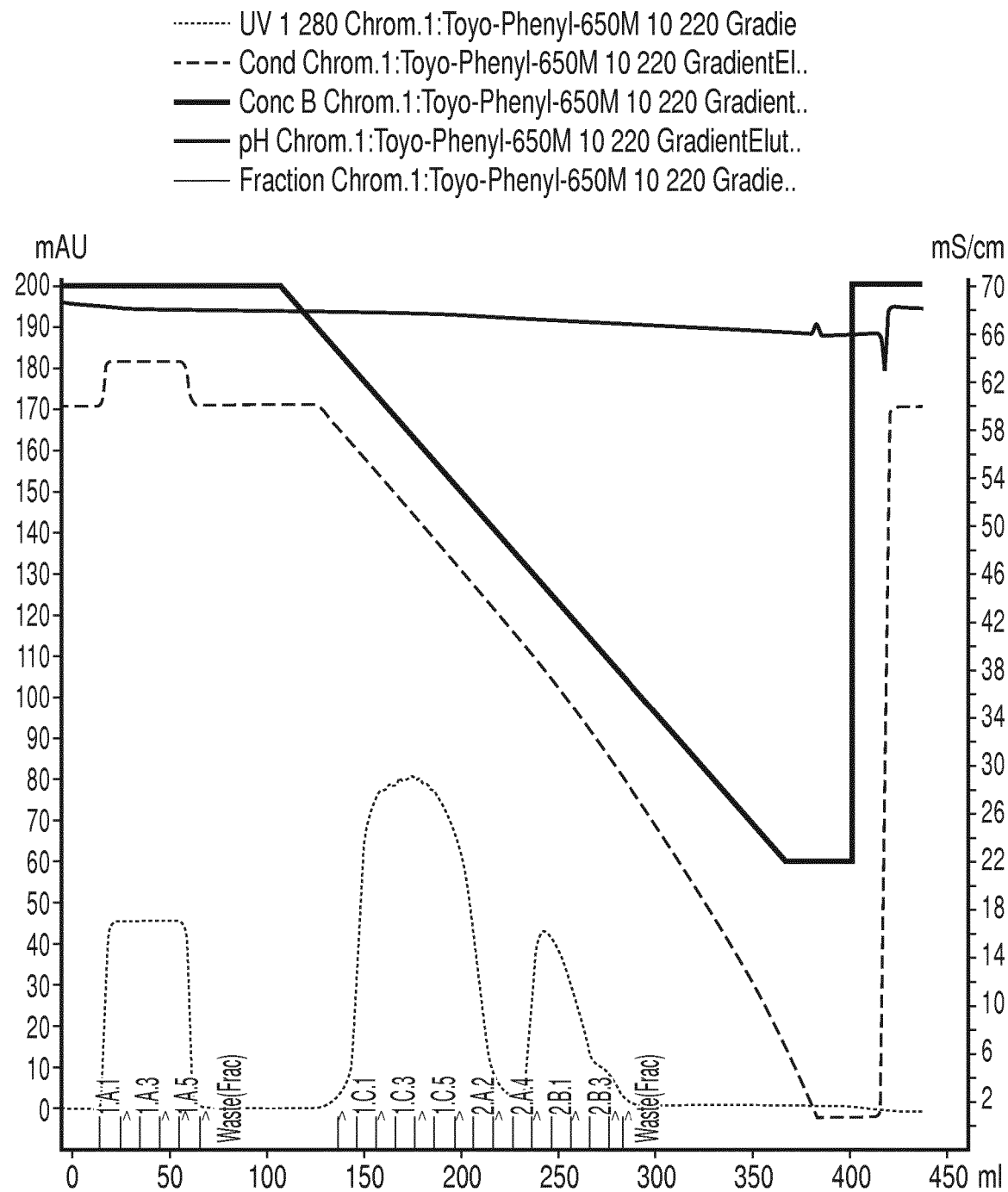
FIG. 9: HIC chromatogram for the performance capacity of the purification on Toyopearl Phenyl 650 M in bind and elute mode.

To equilibrate the Phenyl-650M column, 25 mM bicine, 500 mM $Na_2SO_4$, pH 8 buffer was used. Elution was carried out using a gradient of 500 mM $Na_2SO_4$ to 0 mM $Na_2SO_4$ over 15 CV. The corresponding chromatogram is shown in FIG. 9.

Fractions 1A1-1B1, 1B5-2A3 and 2A4 to 2B4 were each pooled and analysed for their composition by RP-HPLC.

Separation in HIC Flow-Through Mode

The complete 62.7 ml of Product pool 2 (a "second mixture" in accordance with the processes disclosed herein) was used as a sample for separation, corresponding to a protein level of 47.03 mg, composed of 0.58% EPO, 79.9% mono-PEG EPO and 19.52% oligo forms. The conductivity of the sample was adjusted by means of 25 mM bicine, 1 M $Na_2SO_4$, pH 8 buffer, to a target to a conductivity of 50 mS/cm, and injected via a 150 ml Superloop.

Figure 10:
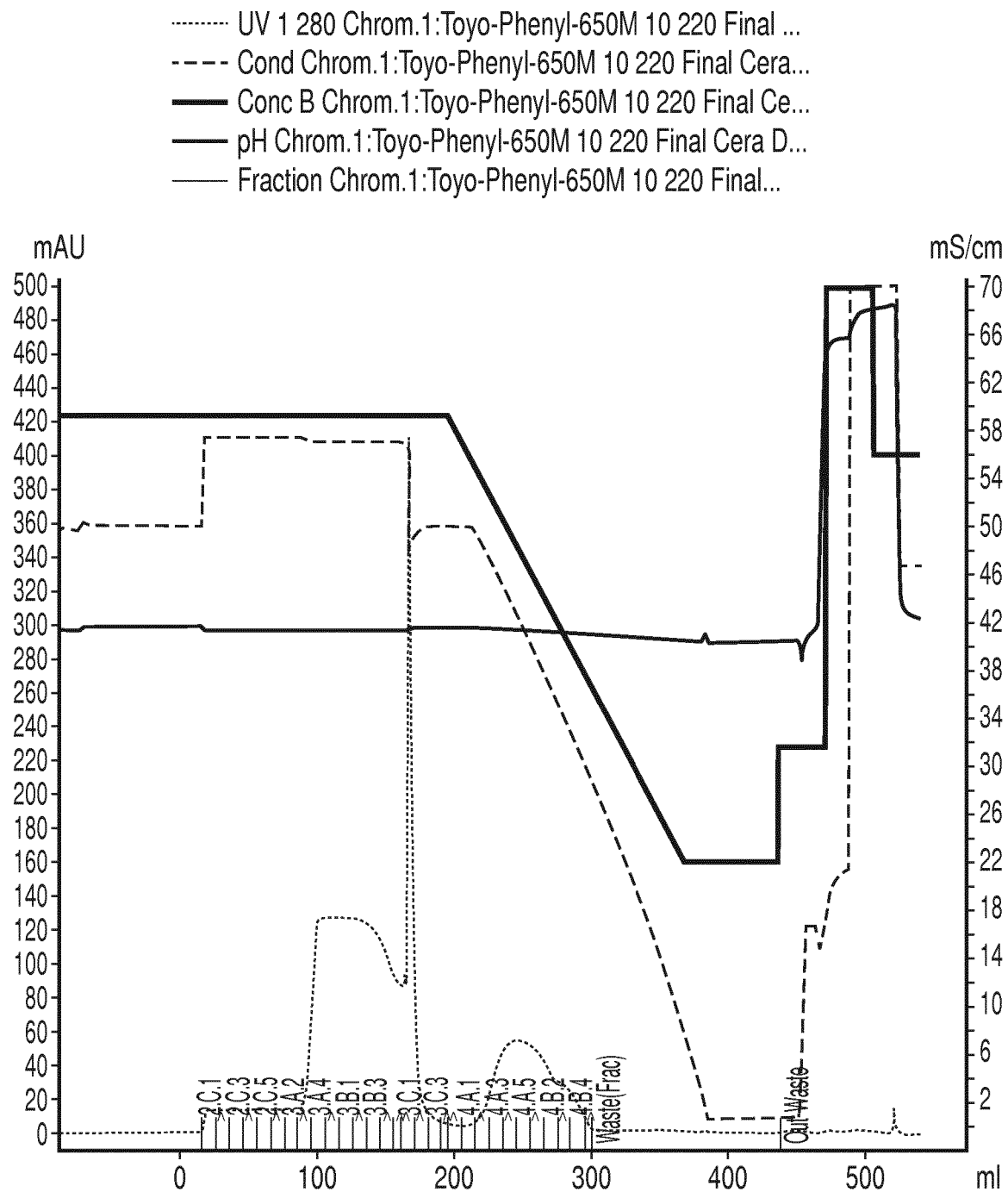
FIG. 10: HIC chromatogram for the performance capacity of the purification on Toyopearl Phenyl 650 M in flow through mode.

The HIC resin was equilibrated with 25 mM bicine, 390 mM $Na_2SO_4$. Elution was carried out as a gradient of 390 mM $Na_2SO_4$ to 0 mM $Na_2SO_4$. The corresponding chromatogram is shown in FIG. 10.

In practice the sample was unintentionally adjusted to 56 mS/cm (rather than the target 50 mS/cm). Therefore a stepwise breakthrough curve can be seen in FIG. 10. In the beginning only EPO is in the flow through. After about 80 ml the UV signal rises to approximately 120 mAU due to a breakthrough of the mono-PEG-EPO. When the conductivity decreases at the transition from load to post load equilibration a peak of earlier bound mono-PEG-EPO is eluted. The oligo-PEG-EPO forms are eluted in the following gradient. Nevertheless separation of mono-PEG-EPO from oligo-PEG-EPO has been shown. Flow through mode is not suitable if unreacted EPO levels are higher than the target value for the product specifications.

Results and Discussion

Cyclic PEGylation and AEC

Table 5 shows the composition of the individual samples, as well as a balancing of the protein quantities.

TABLE 5

Composition, masses and volumes of the individual samples during the process

| | Conc [g/l] | Vol [ml] | Mass [mg] | Fraction | Composition [%] Epo | Mono | Oligo | Mass [mg] Epo | Mono | Oligo |
|---|---|---|---|---|---|---|---|---|---|---|
| PEGylation 1 | | | | | | | | | | |
| Sample 1 | 12.5 | 1 | 12.5 | — | 100 | 0 | 0 | 12.5 | 0 | 0 |
| Epo stock soln | 12.5 | 18 | 225 | — | 100 | 0 | 0 | 225 | 0 | 0 |
| PEG Solution | 66 | 4.5 | 297 | — | — | — | — | — | — | — |
| 25 mM bicine, 7.5 mM Na2SO4 | — | 22.5 | — | — | — | — | — | — | — | — |
| Sample 2 | 5.56 | 0.25 | 1.39 | — | 49.8 | 40.59 | 9.61 | 0.692 | 0.564 | 0.134 |
| Chromatography 1 | | | | | | | | | | |
| Sample 1 | 5.56 | 40.5 | 225 | — | 49.8 | 40.59 | 9.61 | 112 | 91.3 | 21.6 |
| Epo Pool | 5.263 | 16.5 | 86.84 | 1B1-1B4 | 100 | 0 | 0 | 86.840 | 0.000 | 0.000 |
| Sample 3 | 5.263 | 0.2 | 1.0526 | — | 100 | 0 | 0 | 1.053 | 0.000 | 0.000 |
| Product pool | 2.27 | 62.17 | 141.13 | 1A1-1A5 | 10.16 | 72.45 | 16.23 | 14.338 | 102.246 | 22.905 |
| Sample 4 | 2.27 | 0.5 | 1.135 | — | 10.16 | 72.45 | 16.23 | 0.115. | 0.822. | 0.184. |
| PEGylation 2 | | | | | | | | | | |
| Epo Solution | 5.263 | 16.3 | 85.79 | — | 100 | 0 | 0 | 85.787 | 0 | 0 |
| PEG Solution | 68.6 | 1.62 | 111.13 | — | — | — | — | — | — | — |
| Sample 5 | 4.73 | 0.25 | 1.18 | — | 50.88 | 39.91 | 8.61 | 0.602 | 0.472 | 0.102 |
| Chromatography 2 | | | | | | | | | | |
| Sample 2 | 2.22 | 38.05 | 84.60 | — | 50.88 | 39.91 | 8.61 | 43.047 | 33.766 | 7.284 |
| Epo pool | 2.5 | 15 | 37.5 | 1B2-1B4 | 98.82 | 1.18 | 0 | 37.058 | 0.443 | 0.000 |
| Sample 6 | 2.5 | 0.5 | 1.25 | — | 98.82 | 1.18 | 0 | 1.235 | 0.015 | 0.000 |
| Product pool | 0.75 | 62.7 | 47.03 | 1A1-1A5 | 0.58 | 79.9 | 19.52 | 0.273 | 37.573 | 9.179 |
| Sample 7 | 0.75 | 2 | 1.5 | — | 0.58 | 79.9 | 19.52 | 0.009 | 1.199 | 0.293 |
| PEGylation 3 | | | | | | | | | | |
| Epo Solution | 2.5 | 14.5 | 36.25 | — | 98.82 | 1.18 | 0 | 35.822 | 0.428 | 0.000 |
| PEG Solution | 62.84 | 1.72 | 108.0848 | — | — | — | — | — | — | — |
| Sample 8 | 2. | 0.5 | 1.4 | — | 19.22 | 46.1 | 34.69 | 0.269 | 0.645 | 0.486 |
| Chromatography 3 | | | | | | | | | | |
| Sample 2 | — | 150 | — | — | 19.22 | 46.1 | 34.69 | — | — | — |
| Epo pool | 0.42 | 15 | 6.3 | 1C2-1C5 | 98.99 | 1.01 | 0 | 6.236 | 0.064 | 0 |
| Sample 9 | 0.42 | 4 | 1.68 | — | 98.99 | 1.01 | 0 | 1.663 | 0.017 | 0 |
| Product pool | 0.15 | 160.5 | 24.08 | 1A1-1C1 | 0.29 | 58.45 | 41.25 | 0.070 | 14.072 | 9.931 |
| Sampling 10 | 0.15 | 5 | 0.75 | — | 0.29 | 58.45 | 41.25 | 0.002 | 0.438 | 0.309 |
| Total balance Product pools vs Load Sample 1 | | | | | 2.77 | 68.40 | 18.67 | 6.24 | 153.89 | 42.01 |

The first cycle on the AEC was inadvertently overloaded. Due to this, the recovery of unreacted EPO in this experiment is only about 78%. Because the column has been overloaded with EPO there is no PEGylated form in the elution pool. That corroborates that proper sizing of the AEC column reduces the content of PEGylated forms in the AEC Elution Pool and thereby maximizes the yield of PEGylated forms in the intermediate pool. The AEC runs after PEGylation 2 and 3 are not fully loaded with EPO and therefore there is a small amount of PEGylated-EPO in the elution pool, in both cases <2%.

The results of PEGylation 1 and 2 show the consistency of the reaction outcome. Under the chosen conditions the results are about 50% EPO, 40% mono-PEG-EPO and <10% oligo-PEG-EPO.

PEGylation 3 as the final PEGylation uses different conditions to favour the formation of the maximum mono-PEG-EPO content that is possible. This worked well with 46% mono-PEG-EPO content.

The composition each of the intermediate product pools are different. The Pool of the first flow through operation consists of about 10% EPO (due to the breakthrough mentioned above), 72% of mono-PEG-EPO and 16% of oligo-PEG EPO. Without the breakthrough of EPO the composition would have been identical to Run 2 (80% mono-PEG-EPO and 20% oligo-PEG-EPO). The 3rd run employed different PEGylation conditions, which resulted in a higher content of oligo-PEG-EPO in the reaction mixture. This translates into a pool composition of 59% mono-PEG-EPO and 41% oligo Peg EPO.

The total yield of mono-PEG-EPO in the intermediate pool after 3 cycles of "PEGylation reaction plus EPO recovery by AEC" is 68.4%. This is already >50% better than the original process but could be even better if there hasn't been a significant amount of EPO lost during the flow through loading of the first AEC run.

Purification of Mono-PEG EPO by HIC-Separation in Bind & Elute Mode

Table 5 shows the results of the RP HPLC analysis.

TABLE 5

RP-HPLC analysis data for pools of HIC in Bind & Elute mode

| Description | Fraction | Epo [%] | Mono-PEG Epo [%] | Oligo forms [%] |
|---|---|---|---|---|
| Starting sample | — | 10.16 | 72.45 | 16.23 |
| Epo pool | 1A1-1B1 | 100 | 0 | 0 |
| Mono-PEG Epo Pool | 1B5-2A3 | 0 | 100 | 0 |
| Oligo pool | 2A4-2B4 | 0 | 2.33 | 97.67 |

The use of the intermediate pool from AEC Run 1 which contained EPO was used to show the performance of the final purification step by hydrophobic interaction chromatography. The EPO and the mono-PEG-EPO Pool are 100% pure. A small amount of mono-PEG-EPO can still be found in the Oligo-PEG-EPO Pool.

Purification of Mono-PEG EPO by HIC-Separation in Flow-Through Mode

Due to the low protein concentrations of the individual fractions, no meaningful results could be generated by means of RP HPLC. However the chromatogram shows that separation of mono-PEGylated EPO from non-PEGylated and oligo-PEGylated forms was achieved.

REFERENCES

A number of publications are cited above in order to more fully describe and disclose the invention and the state of the art to which the invention pertains. Full citations for these references are provided below. The entirety of each of these references is incorporated herein by reference for all purposes.

Bristow, A, *Pharmeuropa Spec. Issue Biologicals BRP Erythropoietin Bio* 97-2 (1997) 31-48
Delgado, C., et al., Crit. Rev. Ther. Drug Carrier 30 Systems 9 (1992) 249-304)
Fee & Van Alstine, *Chemical Engineering Science*, 2016, 61, 924-939
Francis, G. E., et al., *Int. J. Hematol.* 68 (1998) 1-18
Ingold et al, *React. Chem. Eng.*, 2016, 1,218.
Lu, Y., et al., *Reactive Polymers* 22 (1994) 221-229
Morpurgo, M., et al., *J. Bioconjug. Chem.* 7 (1996) 363-368.
Pfister et al, *Reac React. Chem. Eng.*, 2016, 1,204
Pfister et al. *Biotechnology and Bioengineering*, 2016, 113, 1711-1718.
Veronese, F. M., *Biomaterials* 22 (2001) 405-417.
WO 2009/010270
WO 2012/035037

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press.

The following numbered statements relate to aspects of the present disclosure and form part of the description.

1. A process for producing a mono-PEGylated protein composition comprising at least about 90% mono-PEGylated protein, the process comprising:
    a) providing a first mixture comprising non-PEGylated protein and PEGylated protein, wherein the PEGylated protein comprises mono-PEGylated protein and oligo-PEGylated protein
    b) subjecting the first mixture to an ion exchange chromatography (IEC) step to provide an IEC flow-through solution in which the fraction of PEGylated protein is increased relative to the first mixture; the IEC step comprising
        applying the first mixture to an IEC material under conditions suitable for binding non-PEGylated protein;
    c) collecting the IEC flow-through solution from step b) to provide a second mixture comprising mono-PEGylated protein and oligo-PEGylated protein; and
    d) subjecting the second mixture to a hydrophobic interaction chromatography (HIC) step to provide a mono-PEGylated protein composition in which the fraction of mono-PEGylated protein is increased relative to the second mixture, wherein the mono-PEGylated protein composition comprises at least about 90% mono-PEGylated protein.
2. The process according to statement 1, wherein the protein is a hormone, a cytokine, an enzyme or an antibody.
3. The process according to statement 1 or statement 2, wherein the protein is erythropoietin.
4. The process according to any one of the preceding statements, wherein the IEC step is an AEC step.
5. A process for producing a mono-PEGylated protein composition comprising at least about 90% mono-PEGylated protein, wherein the protein is erythropoietin, the process comprising:
    e) providing a first mixture comprising non-PEGylated protein and PEGylated protein, wherein the PEGylated protein comprises mono-PEGylated protein and oligo-PEGylated protein
    f) subjecting the first mixture to an anion exchange chromatography (AEC) step to provide an AEC flow-through solution in which the fraction of PEGylated protein is increased relative to the first mixture; the AEC step comprising
        applying the first mixture to an AEC material under conditions suitable for binding non-PEGylated protein;
    g) collecting the AEC flow-through solution from step b) to provide a second mixture comprising mono-PEGylated protein and oligo-PEGylated protein; and
    h) subjecting the second mixture to a hydrophobic interaction chromatography (HIC) step to provide a mono-PEGylated protein composition in which the fraction of mono-PEGylated protein is increased relative to the second mixture, wherein the mono-PEGylated protein composition comprises at least about 90% mono-PEGylated protein.
6. The process according to any one of the preceding statements, wherein the IEC material has a binding capacity for the PEGylated protein of less than about 1.5 g/L.
7. The process of according to any one of statements 4 to 6, wherein the AEC material has a binding capacity for the PEGylated protein of less than about 1.5 g/L.
8. The process according to any one of the preceding statements wherein:
    i. the first mixture comprises less than 25% oligo-PEGylated protein; and/or
    ii. the IEC flow-through solution comprises at least 90% PEGylated protein; and/or
    iii. the mono-PEGylated protein composition comprises at least about 95%, 98%, 99%, or 99.9% mono-PEGylated protein.
9. The process according to any one of the preceding statements wherein:
    i. the first mixture comprises less than 25% oligo-PEGylated protein; and/or ii. the AEC flow-through solution comprises at least 90% PEGylated protein; and/or iii. the mono-PEGylated protein composition comprises at least about 95%, 98%, 99%, or 99.9% mono-PEGylated protein.

10. The process according to any one of the preceding statements, wherein step a) further comprises performing a PEGylation reaction comprising reacting the non-PEGylated protein with a PEGylation reagent.

11. The process according to statement 10, wherein the PEGylation reaction is performed at a pH of about 7.0 to 9.0, and wherein the PEG/protein molar ratio is about 0.6-1.0.

12. The process according to statement 10 or 11, comprising
performing a first cycle comprising steps a), b) and c), wherein step b) further comprises eluting non-PEGylated protein from the IEC material to provide an IEC eluate, and
performing a second cycle of steps a), b) and c), in which the non-PEGylated protein eluted in step b) of the first cycle is added to the PEGylation reaction of step a).

13. The process according to statement 10 or 11, wherein the IEC step is an AEC step, comprising
performing a first cycle comprising steps a), b) and c), wherein step b) further comprises eluting non-PEGylated protein from the AEC material to provide an AEC eluate, and
performing a second cycle of steps a), b) and c), in which the non-PEGylated protein eluted in step b) of the first cycle is added to the PEGylation reaction of step a).

14. The process according to statement 12, wherein eluting non-PEGylated protein from the IEC material uses an elution buffer comprising less than or equal to about 45 mM salt 15. The process according to statement 13, wherein eluting non-PEGylated protein from the AEC material uses an elution buffer comprising less than or equal to about 45 mM salt.

16. The process according to any one of statements 12 to 15, wherein the process comprises three, four or five cycles, and wherein step b) of each cycle comprises eluting non-PEGylated protein from the IEC material to provide an IEC eluate, and wherein the non-PEGylated protein eluted in step b) is added to the PEGylation reaction of step a) in the next cycle.

17. The process according to any one of statements 12 to 15, wherein the IEC step is an AEC step, and wherein the process comprises three, four or five cycles, and wherein step b) of each cycle comprises eluting non-PEGylated protein from the AEC material to provide an AEC eluate, and wherein the non-PEGylated protein eluted in step b) is added to the PEGylation reaction of step a) in the next cycle 18. The process according to any one of statements 12 to 17, wherein the IEC eluate from step b) of a cycle is added directly to the PEGylation reaction of step a) of the next cycle.

19. The process according to any one of statements 12 to 17, wherein the IEC step is an AEC step, and wherein the AEC eluate from step b) of a cycle is added directly to the PEGylation reaction of step a) of the next cycle.

20. The process according to any one of statements 12 to 17, in which the non-PEGylated protein eluted in step b) of a cycle is added to the PEGylation reaction of step a) of the next cycle, and wherein fresh non-PEGylated protein is also added to step a) in order to maintain substantially constant PEGylation reaction conditions in step a) of each cycle.

21. The process according to any one of the preceding statements, comprising performing two or more cycles of steps a), b) and c), wherein
step c) further comprises pooling the flow-through solution collected from of each IEC step to provide a second mixture which is a pooled second mixture, and wherein
step d) comprises subjecting the second mixture to an HIC step.

22. The process according to any one of the preceding statements, comprising performing two or more cycles of steps a), b) and c), wherein
step c) further comprises pooling the flow-through solution collected from of each AEC step to provide a second mixture which is a pooled second mixture, and wherein
step d) comprises subjecting the second mixture to an HIC step.

23. The process according to any one of the preceding statements, wherein the IEC step is an AEC step, and wherein
i. the AEC material is Toyopearl Super Q 650 M; and/or
ii. the AEC step is performed at pH of about 7.0 to 9.0; and/or
iii. the AEC step is performed at a conductivity of about 1.0 to 3.0 mS/cm; and/or
iv. the first mixture is applied to the AEC material as a AEC load solution comprising about 10-30 mM bicine and about 1-10 mM $Na_2SO_4$.

24. The process according to any one of the preceding statements, wherein step d) comprises subjecting the second mixture to a HIC step in flow-through mode to provide a HIC flow-through solution in which the fraction of mono-PEGylated protein is increased relative to the second mixture,
the HIC step comprising applying the second mixture to a HIC material under conditions suitable for binding oligo-PEGylated protein, wherein the HIC flow-through provides the mono-PEGylated protein composition.

25. The process according to any one of statements 1 to 23, wherein step d) comprises subjecting the second mixture to a HIC step in bind and elute mode to provide a HIC eluate in which the fraction of mono-PEGylated protein is increased relative to the second mixture, the HIC step comprising
applying the second mixture to a HIC material under conditions suitable for binding mono-PEGylated protein and oligo-PEGylated protein,
eluting the mono-PEGylated protein from the HIC material to provide a HIC eluate, wherein the HIC eluate provides the mono-PEGylated protein.

26. The process according to statement 24, wherein
i. the HIC material is Toyopearl Phenyl 650M; and/or
ii. the HIC step is performed at a pH of about 7.0 to 9.0; and/or
iii. the HIC step is performed at a conductivity of about 30-40 mS/cm; and/or
iv. the second mixture is applied to the HIC material as a HIC load solution comprising about 25 mM bicine and about 390 mM $Na_2SO_4$.

27. The process according to statement 25, wherein
   i. the HIC material is Toyopearl Phenyl 650M; and/or
   ii. the HIC step is performed at a pH of about 7.0 to 9.0; and/or
   iii. the step of eluting the mono-PEGylated protein from the HIC material comprises applying a gradient of from about 50 mS/cm to 0 mS/cm; and/or
   iv. the second mixture is applied to the HIC material as a HIC load solution comprising about 25 mM bicine and about 500 mM $Na_2SO_4$.

28. The process according to any one of the preceding statements, wherein
   i. the IEC step and HIC step are performed at substantially the same pH; or
   ii. the PEGylation reaction, IEC step and HIC step are performed at substantially the same pH.

29. The process according to any one of the preceding statements, wherein
   i. the AEC step and HIC step are performed at substantially the same pH; or
   ii. the PEGylation reaction, AEC step and HIC step are performed at substantially the same pH.

30. The process according to any one of the preceding statements, wherein mono-PEGylated protein comprises a PEG residue having a molecular weight of at least about 20 kDa.

31. The process according to any one of the preceding statements, further comprising formulating the protein composition with a pharmaceutically acceptable carrier to provide a pharmaceutical composition.

32. A process for producing a PEGylated protein mixture, the process comprising:
   a) reacting a non-PEGylated protein with a PEGylation reagent to produce a mixture of reaction products comprising non-PEGylated protein and PEGylated protein, wherein the PEGylated protein comprises mono-PEGylated protein and oligo-PEGylated protein;
   b) subjecting the mixture of reaction products to an ion exchange chromatography (IEC) step to provide an IEC flow-through solution in which the fraction of PEGylated protein is increased relative to the mixture of reaction products;
      the IEC step comprising applying the mixture of reaction products to an IEC material under conditions suitable for binding non-PEGylated protein; and
   c) collecting the IEC flow-through solution from step b) to provide a PEGylated protein mixture comprising mono-PEGylated protein and oligo-PEGylated protein,
   wherein two or more cycles of steps a), b) and c) are performed, in which non-PEGylated protein is recovered in step b) by eluting an IEC eluate from the IEC material and the eluted non-PEGylated protein is used in the PEGylation reaction of step a) of the next cycle.

33. The process according to statement 32, wherein the protein is a hormone, a cytokine, an enzyme or an antibody.

34. The process according to statement 32 or 33, wherein the protein is erythropoietin.

35. The process according to any one of statements 32 to 34, wherein the IEC step is an anion exchange chromatography (AEC) step.

36. A process for producing a PEGylated protein mixture, wherein the protein is erythropoietin, the process comprising:
   a) reacting a non-PEGylated protein with a PEGylation reagent to produce a mixture of reaction products comprising non-PEGylated protein and PEGylated protein, wherein the PEGylated protein comprises mono-PEGylated protein and oligo-PEGylated protein;
   b) subjecting the mixture of reaction products to an anion exchange chromatography (AEC) step to provide an AEC flow-through solution in which the fraction of PEGylated protein is increased relative to the mixture of reaction products;
      the AEC step comprising applying the mixture of reaction products to an AEC material under conditions suitable for binding non-PEGylated protein; and
   c) collecting the AEC flow-through solution from step b) to provide a PEGylated protein mixture comprising mono-PEGylated protein and oligo-PEGylated protein,
   wherein two or more cycles of steps a), b) and c) are performed, in which non-PEGylated protein is recovered in step b) by eluting an AEC eluate from the AEC material and the eluted non-PEGylated protein is used in the PEGylation reaction of step a) of the next cycle.

37. The process according to any one of statements 32 to 36, wherein the mixture of reaction products comprises at least about 20% non-PEGylated protein.

38. The process according to any one of statements 32 to 37 wherein the process comprises three, four or five cycles, in which in step b) of each cycle non-PEGylated protein is recovered and used in the PEGylation reaction of step a) in the next cycle.

39. The process according to any one of statements 32 to 38, wherein step c) further comprises pooling the flow through solution collected from each IEC step to provide a PEGylated protein mixture which is a pooled PEGylated protein mixture.

40. The process according to any one of statements 35 to 39, wherein step c) further comprises pooling the flow through solution collected from each AEC step to provide a PEGylated protein mixture which is a pooled PEGylated protein mixture.

41. The process according to any one of statements 32 to 40, wherein eluting non-PEGylated protein from the IEC material uses an elution buffer comprising less than or equal to about 45 mM salt.

42. The process according to any one of statements 35 to 40, wherein eluting non-PEGylated protein from the AEC material uses an elution buffer comprising less than or equal to about 45 mM salt.

43. The process according to any one of statements 32 to 42, wherein the IEC eluate of a cycle is added directly to the PEGylation reaction of step a) of the next cycle.

44. The process according to any one of statements 35 to 42, wherein the AEC eluate of a cycle is added directly to the PEGylation reaction of step a) of the next cycle.

45. The process according to any one of statements 32 to 44, in which the non-PEGylated protein is recovered and used in the PEGylation reaction of step a) in the next cycle, and wherein fresh non-PEGylated protein is also added to step a) in order to maintain substantially constant PEGylation reaction conditions in step a) of each cycle.

46. The process according to any one of statements 32 to 45 wherein the IEC material has a binding capacity for the PEGylated protein of less than about 1.5 g/L.
47. The process according to any one of statements 35 to 45 wherein the AEC material has a binding capacity for the PEGylated protein of less than about 1.5 g/L.
48. The process according to any one of statements 32 to 47, wherein:
   i. the mixture of reaction products comprises less than 25% oligo-PEGylated protein; and/or
   ii. the IEC flow-through solution comprises at least 90% PEGylated protein.
49. The process according to any one of statements 35 to 47, wherein:
   i. the mixture of reaction products comprises less than 25% oligo-PEGylated protein; and/or
   ii. the AEC flow-through solution comprises at least 90% PEGylated protein.
50. The process according to any one of statements 35 to 49, wherein
   i. the AEC material is Toyopearl Super Q 650 M; and/or
   ii. the AEC step is performed at pH of about 7.0 to 9.0; and/or
   iii. the AEC step is performed at a conductivity of about 1.0 to 3.0 mS/cm; and/or
   iv. the mixture of reaction products is applied to the AEC material as a AEC load solution comprising about 10-30 mM bicine and about 1-10 mM $Na_2SO_4$.
51. The process according to statement 50 wherein the protein is erythropoietin.
52. The process according to any one of statements 32 to 51, wherein the PEGylation reaction is performed at a pH of about 7.0 to 9.0, and wherein the PEG/protein molar ratio is about 0.6-1.0.
53. A process for producing a mono-PEGylated protein composition comprising at least about 90% mono-PEGylated protein, the process comprising:
   subjecting the PEGylated protein mixture comprising mono-PEGylated protein and oligo-PEGylated protein produced by any one of statements 32 to 51 to a purification process separating mono-PEGylated protein and oligo-PEGylated protein; and
   recovering a mono-PEGylated protein composition in which the fraction of mono-PEGylated protein is increased relative to the PEGylated protein mixture, wherein the mono-PEGylated protein composition comprises at least about 90% mono-PEGylated protein.
54. The process of statement 53, wherein the purification process comprises subjecting the PEGylated protein mixture to a hydrophobic interaction chromatography (HIC) step in flow-through mode to provide a HIC flow-through solution in which the fraction of mono-PEGylated protein is increased relative to the PEGylated protein mixture,
   the HIC step comprising applying the PEGylated protein mixture to a HIC material under conditions suitable for binding oligo-PEGylated protein, wherein the HIC flow-through provides the mono-PEGylated protein composition.
55. The process of statement 53, wherein the purification process comprises subjecting the PEGylated protein mixture to a hydrophobic interaction chromatography (HIC) step in bind and elute mode to provide a HIC eluate in which the fraction of mono-PEGylated protein is increased relative to the PEGylated protein mixture, the HIC step comprising
   applying the second mixture to a HIC material under conditions suitable for binding mono-PEGylated protein and oligo-PEGylated protein,
   eluting the mono-PEGylated protein from the HIC material to provide a HIC eluate, wherein the HIC eluate provides the mono-PEGylated protein.
56. The process according to any one of statements 32 to 55 wherein the mono-PEGylated protein composition comprises at least about 95%, 98%, 99%, or 99.9% mono-PEGylated protein.

The invention claimed is:

1. A process for producing a PEGylated protein mixture, comprising the steps of:
   a) reacting a non-PEGylated protein with a PEGylation reagent to produce a mixture of reaction products comprising non-PEGylated protein and PEGylated protein, wherein the PEGylated protein comprises mono-PEGylated protein and oligo-PEGylated protein;
   b) subjecting the mixture of reaction products to an ion exchange chromatography (IEC) step to provide an IEC flow-through solution in which the fraction of PEGylated protein is increased relative to the mixture of reaction products; the IEC step comprising applying the mixture of reaction products to an IEC material under conditions suitable for binding non-PEGylated protein, wherein the IEC step is an anion exchange (AEC) step; and
   c) collecting the IEC flow-through solution from step b) to provide a PEGylated protein mixture comprising mono-PEGylated protein and oligo-PEGylated protein, wherein non-PEGylated protein is recovered in step b) by eluting an IEC eluate from the IEC material and the eluted non-PEGylated protein is used in a subsequent PEGylation reaction, wherein the protein is erythropoietin,
wherein the IEC material has a binding capacity for the non-PEGylated protein of at least about 20 g/L, and
wherein the PEG/protein molar ratio in the PEGylation reaction is about 0.6-1.0.

2. The process according to claim 1, wherein two or more cycles of steps a), b) and c) are performed, in which non-PEGylated protein is recovered in step b) by eluting an IEC eluate from the IEC material and the eluted non-PEGylated protein is used in a subsequent PEGylation reaction.

3. The process according to claim 2, wherein the process comprises three, four or five cycles, in which in step b) of each cycle non-PEGylated protein is recovered and used in a subsequent PEGylation reaction.

4. The process according to claim 2, wherein step c) further comprises pooling the flow-through solution collected from each IEC step to provide a PEGylated protein mixture which is a pooled PEGylated protein mixture.

5. The process according to claim 1, wherein eluting non-PEGylated protein from the IEC material uses an elution buffer comprising less than or equal to about 45 mM salt.

6. The process according to claim 1, wherein the step b) IEC eluate is added directly to the subsequent PEGylation reaction.

7. The process according to claim 1, in which the non-PEGylated protein is recovered and used in a subsequent PEGylation reaction, and wherein fresh non-PEGylated protein is also added to the subsequent PEGylation reaction in order to maintain substantially constant PEGylation reaction conditions in each PEGylation reaction.

8. The process according to claim 1, wherein the IEC material has a binding capacity for the PEGylated protein of less than about 1.5 g/L.

9. The process according to claim 1, wherein:
   i. the mixture of reaction products comprises less than 25% oligo-PEGylated protein; and/or
   ii. the IEC flow-through solution comprises at least 90% PEGylated protein.

10. The process according to claim 1, wherein,
    i. the AEC material is Toyopearl Super Q 650 M; and/or
    ii. the AEC step is performed at pH of about 7.0 to 9.0; and/or
    iii. the AEC step is performed at a conductivity of about 1.0 to 3.0 mS/cm; and/or
    iv. the mixture of reaction products is applied to the AEC material as a AEC load solution comprising about 10-30 mM bicine and about 1-10 mM $Na_2SO_4$.

11. The process according to claim 1, wherein the PEGylation reaction is performed at a pH of about 7.0 to 9.0.

12. The process according to claim 1, further comprising the steps of:
    (d) subjecting the PEGylated protein mixture produced in step (c) of claim 1 and comprising mono-PEGylated protein and oligo-PEGylated protein to a purification process separating mono-PEGylated protein and oligo-PEGylated protein; and
    (e) recovering a mono-PEGylated protein composition in which the fraction of mono-PEGylated protein is increased relative to the PEGylated protein mixture, wherein the mono-PEGylated protein composition comprises at least about 90% mono-PEGylated protein.

13. The process of claim 12, wherein the purification process comprises subjecting the PEGylated protein mixture to a hydrophobic interaction chromatography (HIC) step in flow-through mode to provide a HIC flow-through solution in which the fraction of mono-PEGylated protein is increased relative to the PEGylated protein mixture, and the HIC step comprising applying the PEGylated protein mixture to a HIC material under conditions suitable for binding oligo-PEGylated protein, wherein the HIC flow-through provides the mono-PEGylated protein composition.

14. The process according to claim 13, wherein
    i. the IEC step or HIC step is performed at substantially the same pH; or
    ii. the PEGylation reaction, IEC step or HIC step is performed at substantially the same pH.

15. The process of claim 12, wherein the purification process comprises subjecting the PEGylated protein mixture to a hydrophobic interaction chromatography (HIC) step in bind and elute mode to provide a HIC eluate in which the fraction of mono-PEGylated protein is increased relative to the PEGylated protein mixture, the HIC step comprising
    applying the second mixture to a HIC material under conditions suitable for binding mono-PEGylated protein and oligo-PEGylated protein, and
    eluting the mono-PEGylated protein from the HIC material to provide a HIC eluate, wherein the HIC eluate provides the mono-PEGylated protein.

16. The process according to claim 12, wherein the mono-PEGylated protein composition comprises at least about 95%, 98%, 99%, or 99.9% mono-PEGylated protein.

17. The process according to claim 1 or claim 12, wherein mono-PEGylated protein comprises a PEG residue having a molecular weight of at least about 20 kDa.

18. The process according to claim 1 or claim 12, further comprising formulating the protein composition with a pharmaceutically acceptable carrier to provide a pharmaceutical composition.

* * * * *

SEQUENCE LISTING

```
<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110
```

-continued

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```